US012668619B2

(12) United States Patent　　(10) Patent No.: US 12,668,619 B2
Nishimiya et al.　　　　　　　(45) Date of Patent: Jun. 30, 2026

(54) METHOD OF IMPROVING BLOOD KINETICS OF PEPTIDE

(71) Applicant: Daiichi Sankyo Company, Limited, Tokyo (JP)

(72) Inventors: Daisuke Nishimiya, Nagareyama (JP); Hidenori Yano, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 1075 days.

(21) Appl. No.: 17/291,956

(22) PCT Filed: Nov. 6, 2019

(86) PCT No.: PCT/JP2019/043386
§ 371 (c)(1),
(2) Date: May 6, 2021

(87) PCT Pub. No.: WO2020/095922
PCT Pub. Date: May 14, 2020

(65) Prior Publication Data
US 2022/0002385 A1　　Jan. 6, 2022

(30) Foreign Application Priority Data
Nov. 7, 2018　　(JP) ................................. 2018-209730

(51) Int. Cl.
*A61K 39/395* (2006.01)
*C07K 14/81* (2006.01)
(52) U.S. Cl.
CPC ...... *C07K 14/8135* (2013.01); *C07K 2319/30* (2013.01)
(58) Field of Classification Search
None
See application file for complete search history.

(56) References Cited

U.S. PATENT DOCUMENTS

| | | | |
|---|---|---|---|
| 9,587,235 | B2 | 3/2017 | Buechler et al. |
| 9,944,911 | B2 | 4/2018 | Ring et al. |
| 9,987,328 | B2 | 6/2018 | Zeitler et al. |
| 11,208,467 | B2 * | 12/2021 | Nishimiya ......... C07K 14/8135 |
| 11,292,828 | B2 | 4/2022 | Nishimiya et al. |
| 11,319,345 | B2 * | 5/2022 | Nishimiya ......... C12N 15/1037 |
| 11,845,786 | B2 * | 12/2023 | Nishimiya .............. A61P 11/00 |
| 11,926,655 | B2 * | 3/2024 | Yano .......................... A61P 1/04 |
| 12,024,547 | B2 | 7/2024 | Nishimiya et al. |
| 2005/0202538 | A1 | 9/2005 | Gillies et al. |
| 2011/0183924 | A1 | 7/2011 | Mintz et al. |
| 2015/0197546 | A1 | 7/2015 | Nishimiya et al. |
| 2018/0142038 | A1 | 5/2018 | Brown et al. |
| 2019/0078160 | A1 | 3/2019 | Dressen et al. |
| 2021/0032313 | A1 | 2/2021 | Nishimiya et al. |

FOREIGN PATENT DOCUMENTS

| | | | |
|---|---|---|---|
| CA | 3 047 893 | A1 | 6/2018 |
| CN | 104136037 | A | 11/2014 |
| CN | 105378075 | A | 3/2016 |
| EP | 3 878 469 | A1 | 9/2021 |
| JP | 2015-504899 | A | 2/2015 |
| JP | 2016-519569 | A | 7/2016 |
| JP | 2018-511300 | A | 4/2018 |
| RU | 2 580 038 | C2 | 4/2016 |
| WO | 2005/121344 | A1 | 12/2005 |
| WO | 2006/063055 | A2 | 6/2006 |
| WO | 2013/109752 | A1 | 7/2013 |
| WO | 2014/024914 | A1 | 2/2014 |
| WO | 2014/145050 | A1 | 9/2014 |
| WO | 2017123401 | A1 | 7/2017 |
| WO | 2018117244 | A1 | 6/2018 |
| WO | 2019/049933 | A1 | 3/2019 |
| WO | 2020/095922 | A1 | 5/2020 |

OTHER PUBLICATIONS

Office Action mailed Jul. 8, 2023, issued in Chinese Application No. 201980073436.4, filed Nov. 6, 2019, 18 pages.
Third Office Action mailed Feb. 13, 2024, issued in Japanese Application No. 2020-556105, filed Nov. 6, 2019, 4 pages.
Office Action mailed Aug. 2, 2023, issued in Japanese Application No. 2020-556105, filed Nov. 6, 2019, 8 pages.
International Search report mailed Feb. 4, 2020, issued in corresponding Application No. PCT/JP2019/043386, filed Nov. 6, 2019, 3 pages.
Kwon, Y.T., et al., "Alternative Splicing Results in Differential Expression, Activity, and Localization of the Two Forms of Arginyl-tRNA-Protein Transferase, a Component of the N-End Rule Pathway," Molecular and Cellular Biology, 19(1):182-193, Jan. 1999.
Gonda, D.K. et al., "Universality and Structure of the N-end Rule", the Journal of Biological Chemistry, 264(28):16700-16712, 1989.
Tasaki, T. and Y.T. Kwon, "The mammamilin N-end rule pathway: new insights into its components and physiological roles," Trends in Biochemical Sciences, 32(11):520-528, 2007.
European Search Report mailed Jun. 30, 2022, issued in European Application No. 19882326.2, filed Nov. 6, 2019, 12 pages.
Written Opinion mailed Apr. 2, 2020, issued in corresponding International Application No. PCT/JP2019/043386, filed Nov. 6, 2019, 6 pages.
Second Office Action mailed Dec. 13, 2023, issued in Japanese Application No. 2020-556105, filed Nov. 6, 2019, 4 pages.
Office Action mailed Dec. 29, 2023, issued in Taiwanese Application No. 108140296 filed Nov. 6, 2019, 9 pages.

(Continued)

*Primary Examiner* — Yunsoo Kim
(74) *Attorney, Agent, or Firm* — Christensen O'Connor Johnson Kindness PLLC

(57) ABSTRACT

A method for improving blood kinetics of a peptide is provided. The method for improving blood kinetics of a peptide includes a step of preparing a peptide having a modified amino acid sequence.

13 Claims, 26 Drawing Sheets
Specification includes a Sequence Listing.

(56) References Cited

OTHER PUBLICATIONS

Chen, T. et al., "Identification of Trypsin-Inhibitory Site and Structure Determination of Human SPINK2 Serine Proteinase Inhibitor," Proteins 77:209-219, 2009.

International Search Report mailed Feb. 4, 2020, issued in corresponding Application No. PCT/JP2019/043384, filed Nov. 6, 2019, 4 pages.

Japanese Office Action mailed Jan. 7, 2021, issued in corresponding Application No. JP 2018-209729, filed Nov. 7, 2018, 12 pages.

Kantyka, T., et al., "Inhibition of kallikrein-related peptidases by the serine protease inhibitor of Kazal-type 6," Peptides: Elsevier 32:1187-1192, 2011.

Kherraf, Z., et al., "SPINK2 deficiency causes infertility by inducing sperm defects in heterozygotes and azoospermia in homozygotes," EMBO Molecular Medicine 9(8):1132-1149, May 2017.

Nishimiya, D., et al., "A Protein Scaffold, Engineered SPINK2, for Generation of Inhibitors With High Affinity and Specificity Against Target Proteases," Scientific Reports, 9:11436, 11 pages, 2019.

Pending Claims from corresponding Application No. JP 2018-209729, filed Nov. 7, 2018, 12 pages (for information purposes).

Notice of Allowance mailed Mar. 16, 2021, from prior U.S. Appl. No. 17/064,543, filed Oct. 6, 2020, 10 pages.

Written Opinion mailed Feb. 4, 2020, issued in corresponding Application No. PCT/JP2019/043384, filed Nov. 6, 2019, 8 pages.

Notice of Allowance mailed Feb. 23, 2022, from prior U.S. Appl. No. 17/326,280, filed May 20, 2021, 5 pages.

Extended European Search Report mailed Jul. 14, 2022, issued in Application No. 2022-101377.3, filed Nov. 6, 2019, 8 pages.

Office Action mailed Aug. 5, 2022, issued in corresponding Canadian Application No. 3,118,707, filed Nov. 6, 2019, 8 pages.

Office Action mailed Jun. 14, 2023, issued in corresponding Japanese Application No. 2022-101377, filed Jun. 23, 2022, 7 pages.

Office Action and Search Report mailed Aug. 11, 2023, issued in corresponding Russian Application No. 2021115961, filed Nov. 6, 2019, 23 pages.

Baylot, V., et al., "TCTP Has a Crucial Role in the Different Stages of Prostate Cancer Malignant Progression," Results Probl Cell Differ, 2017, vol. 64 , pp. 255-261.

Badri, H., et al., "Optimization of radiation dosing schedules for proneural glioblastoma," J Math Bio, 2016, vol. 72, N. 5, pp. 1301-1336.

Kuznetsova, E.A., "Brackets in Text of Legal Document as a Linguo-Cognitive Phenomenon [in Russian]," Vestnik Series: Russian Philology, 2015, N3, pp. 37-43.

Singer, M., et al., Genes and Genomes, Moscow, "Mir", 1998, vol. 1, p. 63-64.

Mariuzza, R.A., "The structural basis of antigen-antibody recognition," Ann. Rev. Biophys. Chem., 1987, vol. 16, pp. 139-159.

Colman, P.M., "Effects of amino acid sequence changes on antibody-antigen interactions," Research in Immunology, 1994, vol. 145, Issue 1, pp. 33-36.

Roitt, I., et al., Immunology, Moscow, "Mir", 2000, p. 110-111.

Rudikoff, S., et al., "Single amino acid substation altering antigen-binding specificity," Immunology, 1982, vol. 78, pp. 1979-1983.

Office Action mailed Dec. 28, 2023 as issued in corresponding Colombian Application No. NC2021/0007354, filed Nov. 6, 2019, 33 pages.

Office Action mailed Nov. 16, 2023 as issued in Taiwanese Application No. 11221144070, 16 pages.

Office Action mailed Jul. 9, 2024, issued in Brazilian Patent Application No. 1120210089896, filed Nov. 6, 2019, 11 pages.

Chung, H-Y., et al., "The N-terminal Alanine-Extended GLP-1/IgG-Fc Fusion Protein Confers Resistance to DPP-IV and Reduces Serum Glucose Level in db/db Mice," Regulatory Peptides 170(1-3): 1-3, Oct. 2011.

Examination Report mailed Jan. 5, 2026, issued in related IN Application No. 202117020589, filed Nov. 6, 2019, 15 pages.

* cited by examiner

Amino acid sequence of human SPINK2

DPQFGLFSKYRTPNCSQYRLPGCPRHFNPVCGSDMSTYANECTLCMKIREGGHNIKI

IRNGPC (SEQ ID NO: 1)

[Figure 8]

General formula of SPINK2 variant peptide

GPQFGLFSKYRTPNCX$_1$X$_2$X$_3$X$_4$X$_5$X$_6$X$_7$CX$_8$X$_9$X$_{10}$X$_{11}$X$_{12}$PVCGSDMSTYANECTLCMK

IREGGHNIKIIRNGPC (SEQ ID NO: 2)

[Figure 9]

Amino acid sequence of human KLK5

IINGSDCDMHTQPWQAALLLRPNQLYCGAVLVHPQWLLTAAHCRKKVFRVRLGHYSL

SPVYESGQQMFQGVKSIPHPGYSHPGHSNDLMLIKLNRRIRPTKDVRPINVSSHCPS

AGTKCLVSGWGTTKSPQVHFPKVLQCLNISVLSQKRCEDAYPRQIDDTMFCAGDKAG

RDSCQGDSGGPVVCNGSLQGLVSWGDYPCARPNRPGVYTNLCKFTKWIQETIQANS (SEQ ID NO: 3)

[Figure 10]

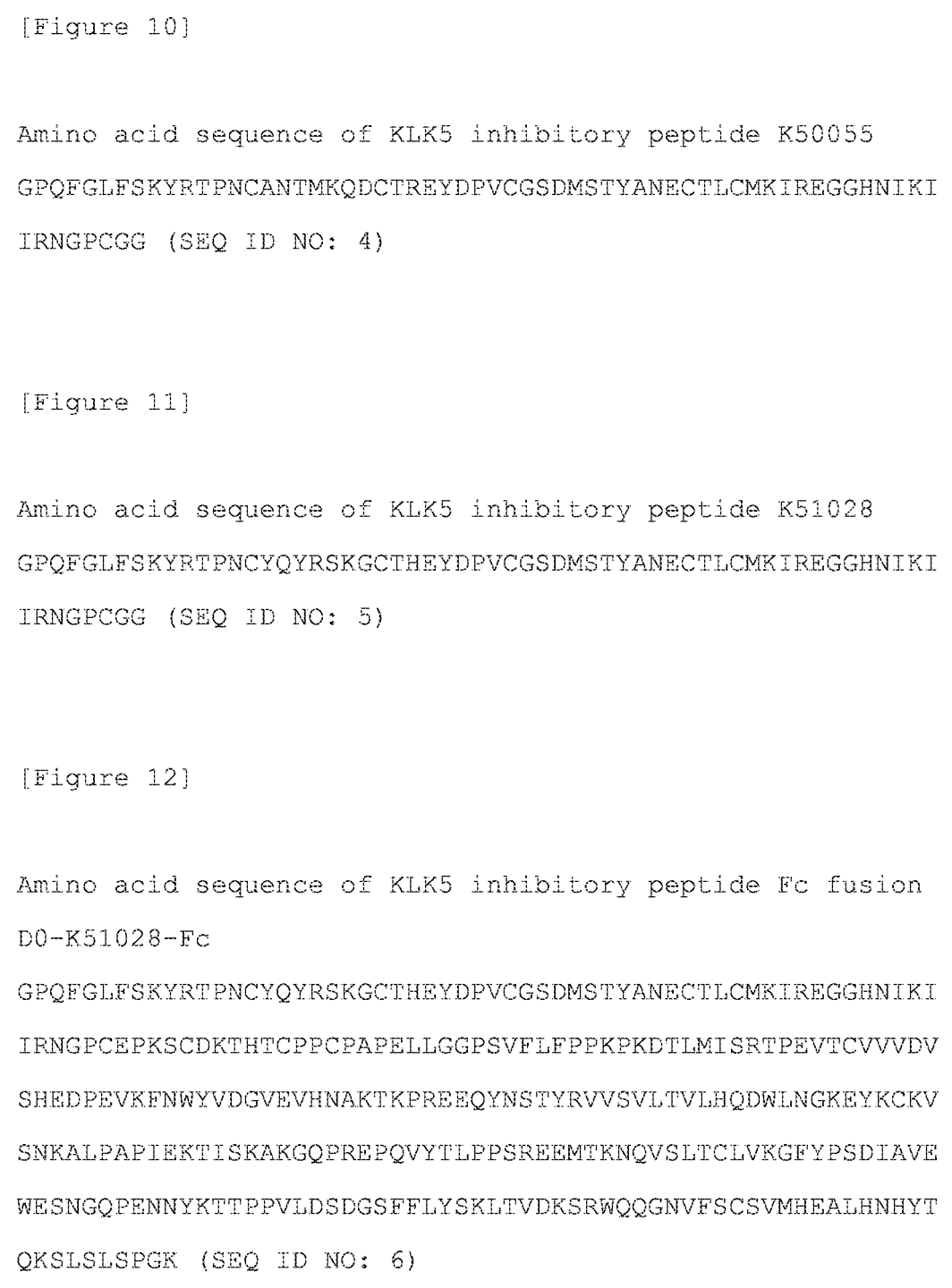

Amino acid sequence of KLK5 inhibitory peptide K50055

GPQFGLFSKYRTPNCANTMKQDCTREYDPVCGSDMSTYANECTLCMKIREGGHNIKI

IRNGPCGG (SEQ ID NO: 4)

[Figure 11]

Amino acid sequence of KLK5 inhibitory peptide K51028

GPQFGLFSKYRTPNCYQYRSKGCTHEYDPVCGSDMSTYANECTLCMKIREGGHNIKI

IRNGPCGG (SEQ ID NO: 5)

[Figure 12]

Amino acid sequence of KLK5 inhibitory peptide Fc fusion

D0-K51028-Fc

GPQFGLFSKYRTPNCYQYRSKGCTHEYDPVCGSDMSTYANECTLCMKIREGGHNIKI

IRNGPCEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKV

SNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYT

QKSLSLSPGK (SEQ ID NO: 6)

[Figure 13]

Amino acid sequence of KLK5 inhibitory peptide Fc fusion

D1-K51028-Fc

DGPQFGLFSKYRTPNCYQYRSKGCTHEYDPVCGSDMSTYANECTLCMKIREGGHNIK

IIRNGPCEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNHY

TQKSLSLSPGK (SEQ ID NO: 7)

[Figure 14]

Amino acid sequence of KLK5 inhibitory peptide Fc fusion

D2-K51028-Fc

DDGPQFGLFSKYRTPNCYQYRSKGCTHEYDPVCGSDMSTYANECTLCMKIREGGHNI

KIIRNGPCEPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVMHEALHNH

YTQKSLSLSPGK (SEQ ID NO: 8)

[Figure 15]

Amino acid sequence of KLK5 inhibitory peptide Fc fusion

D3-K51028-Fc

DDDGPQFGLFSKYRTPNCYQYRSKGCTHEYDPVCGSDMSTYANECTLCMKIREGGHN

IKIIRNGPCEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSVMHEALHN

HYTQKSLSLSPGK (SEQ ID NO: 9)

[Figure 16]

Amino acid sequence of KLK5 inhibitory peptide Fc fusion

D4-K51028-Fc

DDDDGPQFGLFSKYRTPNCYQYRSKGCTHEYDPVCGSDMSTYANECTLCMKIREGGH

NIKIIRNGPCEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCSVMHEALH

NHYTQKSLSLSPGK (SEQ ID NO: 10)

[Figure 17]

Amino acid sequence of KLK5 inhibitory peptide Fc fusion

D5-K51028-Fc

DDDDDGPQFGLFSKYRTPNCYQYRSKGCTHEYDPVCGSDMSTYANECTLCMKIREGG

HNIKIIRNGPCEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSCSVMHEAL

HNHYTQKSLSLSPGK (SEQ ID NO: 11)

[Figure 18]

Amino acid sequence of KLK5 inhibitory peptide Fc fusion

K51028-D5-Fc

GPQFGLFSKYRTPNCYQYRSKGCTHEYDPVCGSDMSTYANECTLCMKIREGGHNIKI

IRNGPCDDDDDEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSCSVMHEAL

HNHYTQKSLSLSPGK (SEQ ID NO: 12)

[Figure 19]

Amino acid sequence of KLK5 inhibitory peptide Fc fusion

E1-K51028-Fc

EGPQFGLFSKYRTPNCYQYRSKGCTHEYDPVCGSDMSTYANECTLCMKIREGGHNIK

IIRNGPCEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNHY

TQKSLSLSPGK (SEQ ID NO: 13)

[Figure 20]

Amino acid sequence of KLK5 inhibitory peptide Fc fusion

D1-K50055-Fc

DGPQFGLFSKYRTPNCANTMKQDCTREYDPVCGSDMSTYANECTLCMKIREGGHNIK

IIRNGPCEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNHY

TQKSLSLSPGK (SEQ ID NO: 14)

[Figure 21]

Nucleotide sequence of primer 1

AGATGGGTGTTGTCTGGCCCTCAGTTCGGCCTGTTC (SEQ ID NO: 15)

[Figure 22]

Nucleotide sequence of primer 2

GCAGGGGCCATTCCGGAT (SEQ ID NO: 16)

[Figure 23]

Nucleotide sequence of primer 3

AGATGGGTGTTGTCTGACGGCCCTCAGTTCGGCCTGTTC (SEQ ID NO: 17)

[Figure 24]

Nucleotide sequence of primer 4

AGATGGGTGTTGTCTGAAGGCCCTCAGTTCGGCCTGTTC (SEQ ID NO: 18)

[Figure 25]

Nucleotide sequence of primer 5

AGATGGGTGTTGTCTGACGACGGCCCTCAGTTCGGCCTGTTC (SEQ ID NO:

Nucleotide sequence of primer 6

AGATGGGTGTTGTCTGATGACGACGGCCCTCAGTTCGGCCTGTTC (SEQ ID NO:

Nucleotide sequence of primer 7

AGATGGGTGTTGTCTGATGATGACGACGGCCCTCAGTTCGGCCTGTTC (SEQ ID

Nucleotide sequence of primer 8

AGATGGGTGTTGTCTGACGATGATGACGACGGCCCTCAGTTCGGCCTGTTC (SEQ

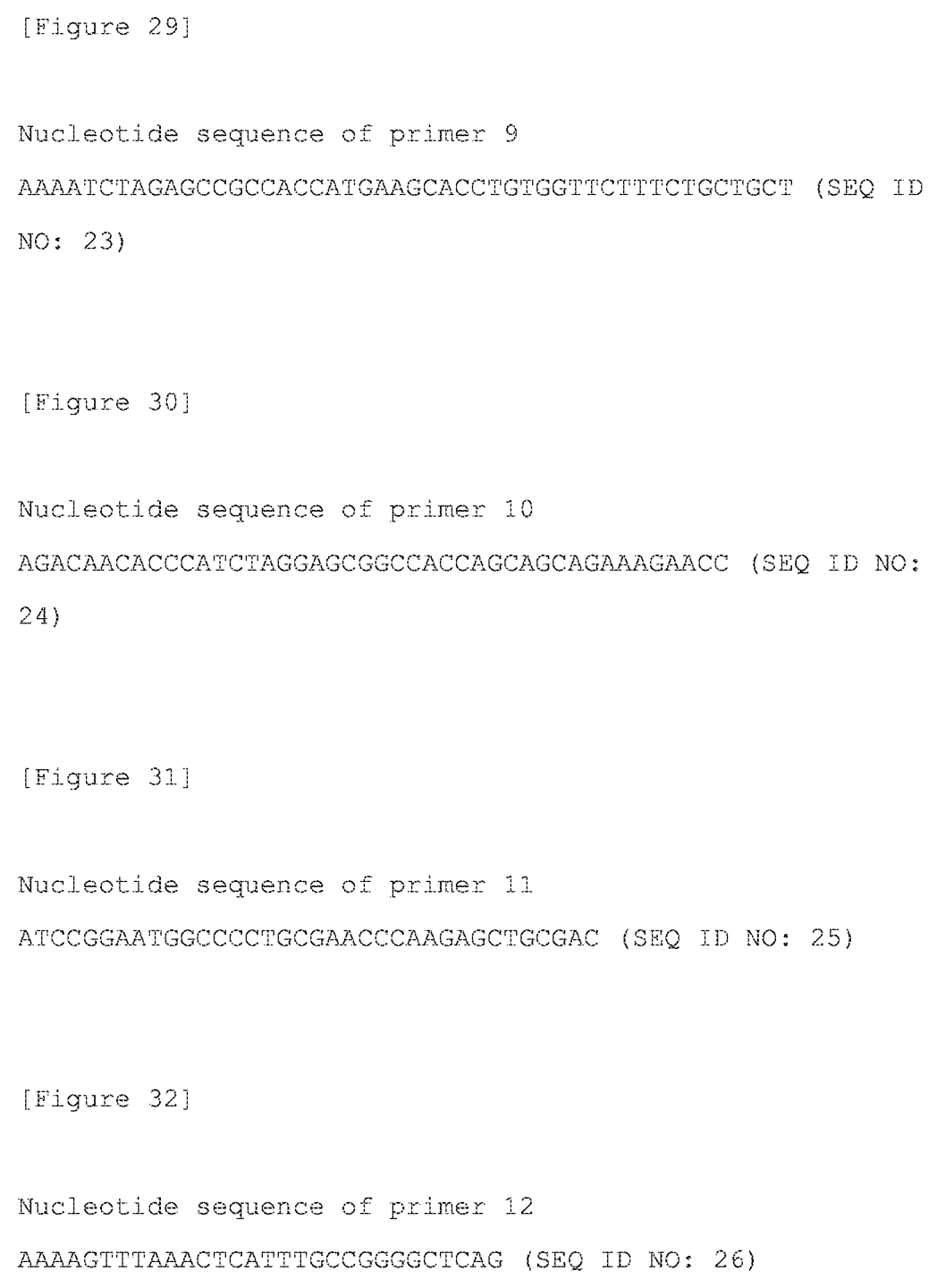

Nucleotide sequence of primer 9

AAAATCTAGAGCCGCCACCATGAAGCACCTGTGGTTCTTTCTGCTGCT (SEQ ID

Nucleotide sequence of primer 10

AGACAACACCCATCTAGGAGCGGCCACCAGCAGCAGAAAGAACC (SEQ ID NO:

Nucleotide sequence of primer 11

ATCCGGAATGGCCCCTGCGAACCCAAGAGCTGCGAC (SEQ ID NO: 25)

[Figure 32]

Nucleotide sequence of primer 12

AAAAGTTTAAACTCATTTGCCGGGGCTCAG (SEQ ID NO: 26)

[Figure 33]

Nucleotide sequence of primer 13

GATGACGACGAACCCAAGAGCTGC (SEQ ID NO: 27)

[Figure 34]

Nucleotide sequence of primer 14

ATCGTCGCAGGGGCCATTCCG (SEQ ID NO: 28)

[Figure 35]

Nucleotide sequence of primer 15

GGCGATTATAAAGATGACGATGATAAACACCATCACCACCATC (SEQ ID NO:

Nucleotide sequence of primer 16

GTTTAAACTCAATGATGGTGGTGATGGTGTTTATCATCGTCAT (SEQ ID NO:

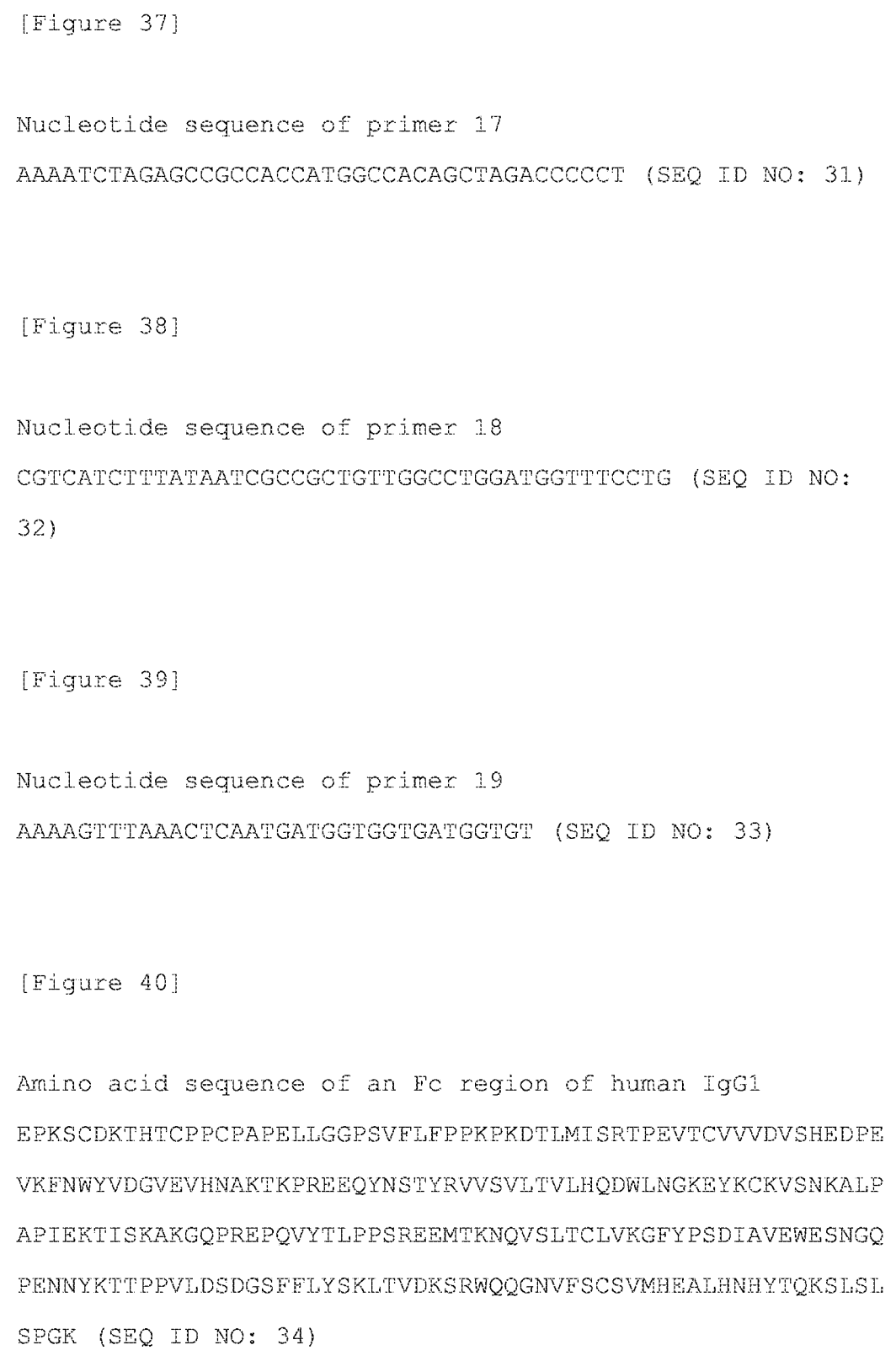

Nucleotide sequence of primer 17

AAAATCTAGAGCCGCCACCATGGCCACAGCTAGACCCCCT (SEQ ID NO: 31)

[Figure 38]

Nucleotide sequence of primer 18

CGTCATCTTTATAATCGCCGCTGTTGGCCTGGATGGTTTCCTG (SEQ ID NO: 32)

[Figure 39]

Nucleotide sequence of primer 19

AAAAGTTTAAACTCAATGATGGTGGTGATGGTGT (SEQ ID NO: 33)

[Figure 40]

Amino acid sequence of an Fc region of human IgG1

EPKSCDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQ

PENNYKTTPPVLDSDGSFFLYSKLTVDKSRWQQGNVFSCSVMHEALHNHYTQKSLSL

SPGK (SEQ ID NO: 34)

[Figure 41]

Nucleotide sequence of primer 20

TGAGTTTAAACTTTTAAACGGGGG (SEQ ID NO: 35)

[Figure 42]

Nucleotide sequence of primer 21

GCAGGGGCCATTCCGGATGATCTT (SEQ ID NO: 36)

[Figure 43]

Amino acid sequence of an Fc region of human IgG2

ERKCCVECPPCPAPPVAGPSVFLFPPKPKDTLMISRTPEVTCVVVDVSHEDPEVQFN

WYVDGVEVHNAKTKPREEQFNSTFRVVSVLTVVHQDWLNGKEYKCKVSNKGLPAPIE

KTISKTKGQPREPQVYTLPPSREEMTKNQVSLTCLVKGFYPSDIAVEWESNGQPENN

YKTTPPMLDSDGSFFLYSKLTVDKSRWQQGNVFSCSVMHEALHNHYTQKSLSLSPGK (SEQ ID NO: 37)

[Figure 44]

Nucleotide sequence of primer 22

CGGAATGGCCCCTGCGAGCGTAAGTGTTGTGTGGAGTGT (SEQ ID NO: 38)

[Figure 45]

Nucleotide sequence of primer 23

CCCCGTTTAAACTCACTTTCCAGGGCTCAGGGAAAGGCT (SEQ ID NO: 39)

[Figure 46]

Amino acid sequence of an Fc region of human IgG4P

ESKYGPPCPPCPAPEFLGGPSVFLFPPKPKDTLMISRTPEVTCVVVDVSQEDPEVQF

NWYVDGVEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWESNGQPEN

NYKTTPPVLDSDGSFFLYSRLTVDKSRWQEGNVFSCSVMHEALHNHYTQKSLSLSLG

K (SEQ ID NO: 40)

[Figure 47]

Nucleotide sequence of primer 24

CGGAATGGCCCCTGCGAATCTAAGTACGGCCCTCCCTGC (SEQ ID NO: 41)

[Figure 48]

Nucleotide sequence of primer 25

CCCCGTTTAAACTCATTTGCCCAGGCTCAGAGACAGGGA (SEQ ID NO: 42)

[Figure 49]

Amino acid sequence of KLK5 inhibitory peptide Fc fusion

D0-K51028-Fc (IgG2)

GPQFGLFSKYRTPNCYQYRSKGCTHEYDPVCGSDMSTYANECTLCMKIREGGHNIKI

IRNGPCERKCCVECPPCPAPPVAGPSVFLFPPKPKDTLMISRTPEVTCVVVDVSHED

PEVQFNWYVDGVEVHNAKTKPREEQFNSTFRVVSVLTVVHQDWLNGKEYKCKVSNKG

LPAPIEKTISKTKGQPREPQVYTLPPSREEMTKNQVSLTCLVKGFYPSDIAVEWESN

GQPENNYKTTPPMLDSDGSFFLYSKLTVDKSRWQQGNVFSCSVMHEALHNHYTQKSL

SLSPGK (SEQ ID NO: 43)

[Figure 50]

Amino acid sequence of KLK5 inhibitory peptide Fc fusion

D1-K51028-Fc (IgG2)

DGPQFGLFSKYRTPNCYQYRSKGCTHEYDPVCGSDMSTYANECTLCMKIREGGHNIK

IIRNGPCERKCCVECPPCPAPPVAGPSVFLFPPKPKDTLMISRTPEVTCVVVDVSHE

DPEVQFNWYVDGVEVHNAKTKPREEQFNSTFRVVSVLTVVHQDWLNGKEYKCKVSNK

GLPAPIEKTISKTKGQPREPQVYTLPPSREEMTKNQVSLTCLVKGFYPSDIAVEWES

NGQPENNYKTTPPMLDSDGSFFLYSKLTVDKSRWQQGNVFSCSVMHEALHNHYTQKS

LSLSPGK (SEQ ID NO: 44)

[Figure 51]

Amino acid sequence of KLK5 inhibitory peptide Fc fusion

D3-K51028-Fc (IgG2)

DDDGPQFGLFSKYRTPNCYQYRSKGCTHEYDPVCGSDMSTYANECTLCMKIREGGHN

IKIIRNGPCERKCCVECPPCPAPPVAGPSVFLFPPKPKDTLMISRTPEVTCVVVDVS

HEDPEVQFNWYVDGVEVHNAKTKPREEQFNSTFRVVSVLTVVHQDWLNGKEYKCKVS

NKGLPAPIEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEALHNHYTQ

KSLSLSPGK (SEQ ID NO: 45)

[Figure 52]

Amino acid sequence of KLK5 inhibitory peptide Fc fusion

D0-K51028-Fc (IgG4P)

GPQFGLFSKYRTPNCYQYRSKGCTHEYDPVCGSDMSTYANECTLCMKIREGGHNIKI

IRNGPCESKYGPPCPPCPAPEFLGGPSVFLFPPKPKDTLMISRTPEVTCVVVDVSQE

DPEVQFNWYVDGVEVHNAKTKPREEQFNSTYRVVSVLTVLHQDWLNGKEYKCKVSNK

GLPSSIEKTISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEALHNHYTQKS

LSLSLGK (SEQ ID NO: 46)

[Figure 53]

Amino acid sequence of KLK5 inhibitory peptide Fc fusion

D1-K51028-Fc (IgG4P)

DGPQFGLFSKYRTPNCYQYRSKGCTHEYDPVCGSDMSTYANECTLCMKIREGGHNIK

IIRNGPCESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKEYKCKVSN

KGLPSSIEKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEALHNHYTQK

SLSLSLGK (SEQ ID NO: 47)

[Figure 54]

Amino acid sequence of KLK5 inhibitory peptide Fc fusion

D3-K51028-Fc (IgG4P)

DDDGPQFGLFSKYRTPNCYQYRSKGCTHEYDPVCGSDMSTYANECTLCMKIREGGHN

IKIIRNGPCESKYGPPCPPCPAPEFLGGPSVFLFPPKPKDTLMISRTPEVTCVVVDV

SQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVE

WESNGQPENNYKTTPPVLDSDGSFFLYSRLTVDKSRWQEGNVFSCSVMHEALHNHYT

QKSLSLSLGK (SEQ ID NO: 48)

METHOD OF IMPROVING BLOOD KINETICS OF PEPTIDE

TECHNICAL FIELD

The present invention relates to a method for improving blood kinetics of a peptide or a conjugate containing the peptide, a peptide or a conjugate containing the peptide which have improved blood kinetics, a pharmaceutical composition containing a peptide or a conjugate containing the peptide which have improved blood kinetics, and the like.

BACKGROUND ART

Biological agents such as antibody pharmaceuticals and recombinant proteins have been researched and developed to a remarkable degree, and there are more than 200 biological agents approved by the Food and Drug Administration (FDA) (Non-Patent Literature 1). The indications of these have extended to various diseases such as cancer, autoimmune diseases, e.g., rheumatoid arthritis and multiple sclerosis, skin diseases, and neuropathic pain. In recent years, due to the progress of protein engineering, the development of recombinant proteins such as antibody fragments and non-antibody scaffolds have been widely attempted. Since these molecules, just like antibody pharmaceuticals, have a high binding activity against a protein X to be targeted, it is expected that their use as therapeutic agents will lead to high drug efficacy and reduced side effects. The molecular weight of antibody pharmaceuticals is about 150 kDa, while the molecular weight of recombinant proteins is as small as about 5 to 50 kDa. Recombinant proteins and hormone peptides exhibit high biological activity, but their half-life in blood is short due to their small molecular weights. In order to maintain the activity of low molecular weight proteins and peptides for a longer period, an approach that extends their blood half-life is needed.

In general, except via specific elimination pathways by target cells, higher molecular weight proteins are eliminated from the body after undergoing intracellular degradation following pinocytosis and receptor-mediated endocytosis, while lower molecular weight proteins and peptides are eliminated from the body after undergoing glomerular filtration in the kidney or degradation during reabsorption. It is known that molecular weights, shapes, charges or the like of low molecular weight proteins and peptides have a significant effect on clearance. Thus, in order to improve the blood half-life of low molecular weight proteins and peptides, an approach of increasing their molecular weight or making them bind to serum proteins are considered (Non-Patent Literature 2). Examples of the approach of increasing the molecular weight of low molecular weight proteins and peptides include the approach of binding them to Polyethylene glycol (PEG), a glycochain, a biodegradable polymer, or the like. Examples of the approach of making a low molecular weight protein or peptide bind to serum proteins include the approach of fusing them with albumin or an albumin-binding molecule. Furthermore, binding to the immunoglobulin Fc region is also effective to extend their blood half-life. In addition to the magnitude of the molecular weight, antibodies exhibit a longer blood half-life than other proteins because, even when they are incorporated into vascular endothelial cells or the like, they exhibit a recycling effect in which their immunoglobulin Fc moieties are pumped out into the blood via binding to a fetal Fc receptor (FcRn) in the endosome (Non-Patent Literature 3). By focusing on this characteristic nature of the Fc region, Fc fusions have been developed as blood half-life extension tools for low molecular weight proteins and peptides. Applications thereof to proteins and peptides have been reported in each of the modification methods, and multiple items have come to market.

Fusions of low molecular weight proteins or peptides with the Fc region are expected to have an extended blood half-life, but in many cases, the blood half-life is shorter than that of IgG, and challenges remain in improving blood exposure amount (Non-Patent Literature 4). In order to maintain drug efficacy of a therapeutic agent, it is required to improve the blood exposure amount of the Fc fusions. Methods for altering blood half-life or blood exposure amount of monoclonal antibodies and Fc fusions have been previously reported. Examples of such methods include a method of altering blood half-life by altering the affinity of an antibody with FcRn (Non-Patent Literatures 3 and 5). In antibodies and receptor Fc fusions, addition of a glycochain to a moiety (a variable region in antibodies, a receptor moiety in receptor Fc fusions) other than the Fc region achieves higher exposure (Non-Patent Literature 3), but this method is not sufficiently effective when applied to smaller proteins of 50-60 kDa or less. Examples of methods to determine the charge on a protein include ascertaining its isoelectric point (pI). When an antibody has high pI, the antibody is positively charged because pH in the body is near neutral. As a result, the antibody is more likely to interact with cell membranes which are negatively charged, leading to increased uptake into tissues and clearance, and reduced or decreased blood half-life and blood exposure amount. Conversely, it is known that lowering pI of antibodies leads to extension of their blood half-life (Non-Patent Literature 3), but it is not known if these methods can be applied to proteins other than antibodies. As another example, it has been reported that stability in blood is improved by adding 4 to 15 acidic amino acids to the N-terminus end of N-acetylgalactosamine-6-sulfate sulfatase (Patent Literature 1).

However, no known method has been shown to be versatile for any protein regardless of its molecular weight. Thus, conventionally, a method to improve blood half-life or blood exposure is sought in individual cases.

Serine Protease Inhibitor Kazal-type 2 (SPINK2) is a Kazal-like domain having three disulfide bonds, and functions as a trypsin/acrosin inhibitor (Non-Patent Literature 6). Its molecular weight is small at 7 kDa, and when SPINK2 or a SPINK2 variant is administered to an individual, it is presumed that its elimination from the body is fast.

CITATION LIST

Patent Literature

Patent Literature 1: Japanese Patent No. 4750718 B2

Non-Patent Literature

Non-Patent Literature 1: Usmani S S, et al. (2017) PLoS One, 12(7): e0181748

Non-Patent Literature 2: Strohl W R et al. (2015), BioDrugs, 29(4): pp. 215-239

Non-Patent Literature 3: Liu L et al. (2018), Protein Cell 9(1): pp. 15-32

Non-Patent Literature 4: Unverdorben F, et al. (2016) MAbs 8(1): pp. 120-128

Non-Patent Literature 5: Saxena A, et al. (2016) Front Immunol. 7: 580

Non-Patent Literature 6: Chen T, et al. (2009) Proteins 77(1): pp. 209-219

SUMMARY OF INVENTION

Technical Problem

An object of the present invention is to provide a method for improving blood kinetics of a peptide.

Solution to Problem

The present invention relates to the following:

(1) a conjugate of a peptide, the conjugate being the following (i) or (ii):

(i) a conjugate of the peptide comprising, from the amino terminus to the carboxyl terminus, one to three aspartic acids and/or glutamic acids, an amino acid sequence contained in the peptide, and an amino acid sequence contained in an Fc region or a fragment thereof of an immunoglobulin, in this order;

(ii) a conjugate of the peptide comprising, from the amino terminus to the carboxyl terminus, one to three aspartic acids and/or glutamic acids, an amino acid sequence contained in an Fc region or a fragment thereof of an immunoglobulin, and the amino acid sequence contained in the peptide, in this order, (2) the conjugate according to (1), wherein the peptide is a SPINK2 variant peptide, (3) the conjugate according to (1), wherein the peptide is an antibody or an antigen-binding fragment thereof, (4) the conjugate according to any one of (1) to (3), wherein the amino acid sequence contained in the peptide is attached via a linker sequence to the amino acid sequence contained in the Fc region or a fragment thereof, (5) the conjugate according to any one of (1) to (3), wherein the amino acid sequence contained in the peptide is directly attached to the amino acid sequence contained in the Fc region or a fragment thereof, (6) the conjugate according to any one of (1) to (5), wherein the one to three aspartic acids and/or glutamic acids are attached via a linker sequence to the amino acid sequence contained in the peptide or the amino acid sequence contained in the Fc region or a fragment thereof, (7) the conjugate according to any one of (1) to (5), wherein the one to three aspartic acids and/or glutamic acids are directly attached to the amino acid sequence contained in the peptide or the amino acid sequence contained in the Fc region or a fragment thereof, (8) the conjugate according to any one of (1) to (7), wherein the immunoglobulin or a fragment thereof is a Fc region or a fragment thereof of IgG1, IgG2, IgG3, IgG4, IgM, IgAQ1, IgA2, IgD, and/or IgE, (9) the conjugate according to any one of (1) to (8), wherein the immunoglobulin is a human immunoglobulin,

(10) the conjugate according to any one of (1) to (9), wherein the immunoglobulin is human IgG1,

(11) the conjugate according to any one of (1) to (10), wherein the immunoglobulin is a wild-type or a variant,

(12) the conjugate according to any one of (1) to (11), wherein the conjugate has a suppressed blood concentration decrease over time or an increased blood exposure amount compared to a conjugate lacking the one to three aspartic acids and/or glutamic acids at the amino terminus,

(13) the conjugate according to any one of (1) to (12), wherein the conjugate binds to a human disease-related target molecule,

(14) the conjugate according to (13), wherein the peptide is a SPINK2 variant and the amino acid sequence contained in the peptide is represented by SEQ ID NO: 2 (FIG. 8),

(15) a composition comprising the conjugate according to any one of (1) to (14),

(16) the conjugate according to (1) to (13), wherein the peptide suppresses, inhibits, agonizes or activates an activity of a human disease-related target molecule,

(17) the conjugate according to (16), wherein the peptide is a SPINK2 variant and the amino acid sequence contained in the peptide is represented by SEQ ID NO: 2 (FIG. 8),

(18) a pharmaceutical composition comprising the conjugate according to (16) or (17),

(19) a method for producing the conjugate according to (1), comprising the following step (i) or (ii):

(i) adding the one to three aspartic acids and/or glutamic acids to the amino terminus end of a fusion containing the peptide and the Fc region or a fragment thereof of an immunoglobulin;

(ii) introducing, into a cell, a polynucleotide comprising an amino acid sequence (c) containing an amino acid sequence (a) contained in the fusion and an amino acid sequence (b) consisting of the one to three aspartic acids and/or glutamic acids, wherein the amino acid sequence (b) is located at the amino terminus end of the amino acid sequence (a), culturing the cell, and recovering a conjugate containing the fusion from the culture,

(20) the method according to (19), wherein the peptide is a SPINK2 variant peptide,

(21) the method according to (19), wherein the peptide is an antibody or an antigen-binding fragment thereof,

(22) the method according to any one of (19) to (21), wherein the Fc region or a fragment thereof is located at the carboxyl terminus end of the peptide,

(23) the method according to any one of (19) to (21), wherein the Fc region or a fragment thereof is located at the amino terminus end of the SPINK2 variant peptide,

(24) the method according to any one of (19) to (23), wherein the Fc region or a fragment thereof is fused via a linker to the peptide, or an amino acid sequence contained in the peptide is attached via a linker sequence to an amino acid sequence contained in the Fc region or a fragment thereof of an immunoglobulin,

(25) the method according to any one of (19) to (23), wherein the Fc region or a fragment thereof is directly fused to the peptide, or an amino acid sequence contained in the peptide is directly attached to an amino acid sequence contained in the Fc region or a fragment thereof of an immunoglobulin,

(26) the method according to any one of (19) to (25), wherein the immunoglobulin is an Fc region or a fragment thereof of IgG1, IgG2, IgG3, IgG4, IgM, IgA1, IgA2, IgD, and/or IgE,

(27) the method according to any one of (19) to (26), wherein the immunoglobulin is a human immunoglobulin,

(28) the method according to any one of (19) to (27), wherein the immunoglobulin is human IgG1,

(29) the method according to any one of (19) to (28), wherein the immunoglobulin is a wild-type or a variant,

(30) the method according to any one of (19) to (29), wherein the conjugate has a suppressed blood concentration decrease over time or an increased blood exposure amount compared to a conjugate lacking the one to three aspartic acids and/or glutamic acids at the amino terminus,

(31) the method according to any one of (19) to (30), wherein the one to three aspartic acids and/or glutamic acids are attached via a linker to the amino terminus end of the fusion, or an amino acid sequence consisting of the one to three aspartic acids and/or glutamic acids is attached via a linker sequence to the amino terminus end of the amino acid sequence contained in the fusion,

(32) the method according to any one of (19) to (30), wherein the one to three aspartic acids and/or glutamic acids are directly attached to the amino terminus end of the fusion, or an amino acid sequence consisting of the one to three aspartic acids and/or glutamic acids is directly attached to the amino terminus end of the amino acid sequence contained in the fusion,

(33) the method according to any one of (19) to (32), wherein the peptide binds to a human disease-related target molecule,

(34) the method according to any one of (19) to (33), wherein the peptide suppresses, inhibits, agonizes or activates an activity of a human disease-related target molecule,

(35) the method according to (34), wherein the peptide is a SPINK2 variant peptide and the amino acid sequence contained in the peptide is represented by SEQ ID NO: 2 (FIG. 8), (1A) a method for suppressing a decrease in blood concentration over time and/or increasing blood exposure amount of a SPINK2 variant peptide-containing conjugate, the method comprising the following step (i) or (ii):

(i) adding an oligopeptide consisting of one to several aspartic acids and/or glutamic acids to the amino terminus end of a conjugate in which the SPINK2 variant peptide is fused to an Fc region or a fragment thereof of an immunoglobulin;

(ii) preparing a conjugate containing an amino acid sequence in which one to several aspartic acids and/or glutamic acids are added to the amino terminus end of an amino acid sequence containing an amino acid sequence contained in the SPINK2 variant peptide and an amino acid sequence contained in an Fc region or a fragment thereof of an immunoglobulin, (2A) The method according to (1A), wherein the Fc region or a fragment thereof is located at the carboxyl terminus end of the SPINK2 variant peptide, (3A) the method according to (1A), wherein the Fc region or a fragment thereof is located at the amino terminus end of the SPINK2 variant peptide, (4A) the method according to any one of (1A) to (3A), wherein the Fc region or a fragment thereof is fused via a linker to the SPINK2 variant peptide, or an amino acid sequence contained in the SPINK2 variant peptide is attached via a linker sequence to an amino acid sequence contained in the Fc region of an immunoglobulin, (5A) the method according to any one of (1A) to (3A), wherein the Fc region or a fragment thereof is directly fused to the SPINK2 variant peptide, or an amino acid sequence contained in the SPINK2 variant peptide is directly added to an amino acid sequence contained in the Fc region of an immunoglobulin, (6A) the method according to any one of (1A) to (5A), wherein the immunoglobulin is an Fc region or a fragment thereof of IgG1, IgG2, IgG3, IgG4, IgM, IgA1, IgA2, IgD, and/or IgE, (7A) the method according to any one of (1A) to (6A), wherein the immunoglobulin is a human immunoglobulin, (8A) the method according to any one of (1A) to (7A), wherein the immunoglobulin is human IgG1, (9A) the method according to any one of (1A) to (8A), wherein the immunoglobulin is a wild-type or a variant, (10A) the method according to any one of (1A) to (9A), wherein the oligopeptide is added via a linker to the amino terminus end of the conjugate described in (i), or the one to several aspartic acids and/or glutamic acids are added via a linker sequence to the amino terminus end of the amino acid sequence containing an amino acid sequence contained in the SPINK2 variant peptide and an amino acid sequence contained in the Fc region or a fragment thereof of an immunoglobulin described in (ii), (11A) the method according to any one of (1A) to (9A), wherein the oligopeptide is directly added to the amino terminus end of the conjugate described in (i), or the one to several aspartic acids and/or glutamic acids are directly added to the amino terminus end of the amino acid sequence containing an amino acid sequence contained in the SPINK2 variant peptide and an amino acid sequence contained in the Fc region or a fragment thereof of an immunoglobulin described in (ii), (12A) the method according to any one of (1A) to (11A), wherein the SPINK2 variant peptide binds to a human disease-related target molecule, (13A) the method according to any one of (1A) to (12A), wherein the SPINK2 variant peptide suppresses or inhibits an activity of a human disease-related target molecule, (14A) the method according to any one of (1A) to (13A), wherein the amino acid sequence contained in the SPINK2 variant peptide is in accordance with (i) or (ii):

(i) an amino acid sequence represented by SEQ ID NO: 2 (FIG. 8), and contained in a peptide that binds to a human disease-related target molecule or suppresses or inhibits an activity of the molecule;

(ii) an amino acid sequence containing an amino acid sequence that is 90% or more identical to the amino acid sequence described in (i), and contained in a peptide that binds to the molecule or suppresses or inhibits an activity of the molecule, (15A) a conjugate of a SPINK2 variant, the conjugate being the following (i) or (ii):

(i) a conjugate of the SPINK2 variant comprising, from the amino terminus to the carboxyl terminus, one to several aspartic acids and/or glutamic acids, an amino acid sequence contained in a SPINK2 variant peptide, and an amino acid sequence contained in an Fc region or a fragment thereof of an immunoglobulin, in this order;

(ii) a conjugate of the SPINK2 variant comprising, from the amino terminus to the carboxyl terminus, one to several aspartic acids and/or glutamic acids, an amino acid sequence contained in an Fc region or a fragment thereof of an immunoglobulin, and an amino acid sequence contained in a SPINK2 variant peptide, in this order, (16A) the conjugate according to (15A), wherein the amino acid sequence contained in the SPINK2 variant peptide is attached via a linker sequence to the amino acid sequence contained in the Fc region, (17A) the conjugate according to (15A), wherein the amino acid sequence contained in the SPINK2 variant peptide is directly attached to the amino acid sequence contained in the Fc region, (18A) the conjugate according to any one of (15A) to (17A), wherein the one to several aspartic acids and/or glutamic acids are attached via a linker sequence to the amino acid sequence contained in the SPINK2 variant peptide or the amino acid sequence contained in the Fc region, (19A) the conjugate according to any one of (15A) to (17A), wherein the one to several aspartic acids and/or glutamic acids are directly attached to the amino acid sequence contained in the SPINK2 variant peptide or the amino acid sequence contained in the Fc region, (20A) the conjugate according to any one of (15A) to (19A), wherein the immunoglobulin is an Fc region or a fragment thereof of IgG1, IgG2, IgG3, IgG4, IgM, IgA1, IgA2, IgD, and/or IgE, (21A) the conjugate according to any one of (15A) to (20A), wherein the immunoglobulin is a human immunoglobulin, (22A) the conjugate according to any one of (15A) to (21A), wherein the immunoglobulin is human IgG1, (23A) the method according to any one of (15A) to (22A), wherein the immunoglobulin is a wild-type or a variant, (24A) the conjugate according to any one of (15A) to (23A), wherein the conjugate has a suppressed blood concentration decrease over time or an increased blood exposure amount compared to a conjugate lacking the one to several aspartic acids and/or glutamic acids at the amino terminus, (25A) the conjugate according to any one of (15A) to (24A), wherein the SPINK2 variant peptide binds to a human disease-related target molecule, (26A) the conjugate according to any one of (15A) to (25A), wherein the SPINK2 variant peptide suppresses or inhibits an activity of a human disease-related target molecule, (27A) the conjugate according to any one of (15A) to (26A), wherein the amino acid sequence contained in the SPINK2 variant peptide is in accordance with (i) or (ii):

(i) an amino acid sequence represented by SEQ ID NO: 2 (FIG. 8), and contained in a peptide that binds to a human disease-related target molecule or suppresses or inhibits an activity of the molecule;

(ii) an amino acid sequence containing an amino acid sequence that is 90% or more identical to the amino acid sequence described in (i), and contained in a peptide that binds to the molecule or suppresses or inhibits an activity of the molecule, (28A) a composition comprising the conjugate according to any one of (15A) to (27A), and

(29A) a pharmaceutical composition comprising the conjugate according to any one of (25A) to (27A), and the like.

Advantageous Effects of Invention

The blood kinetics improvement method provided by the present invention brings suppression of blood concentration decrease over time, increase of blood exposure amount, and the like of a peptide or a conjugate containing the peptide. Pharmaceuticals containing the peptide or the conjugate can suitably be used for treating or preventing various diseases.

BRIEF DESCRIPTION OF DRAWINGS

FIG. 1 shows SPINK2-Fc fusions subjected to a PK test.

FIG. 7 shows an amino acid sequence of human SPINK2 (SEQ ID NO: 1).

FIG. 8 shows a general formula of SPINK2 variant peptide (SEQ ID NO: 2).

FIG. 9 shows an amino acid sequence of human KLK5 (SEQ ID NO: 3).

FIG. 10 shows an amino acid sequence of KLK5 inhibitory peptide K50055 (SEQ ID NO: 4).

FIG. 11 shows an amino acid sequence of KLK5 inhibitory peptide K51028 (SEQ ID NO: 5).

FIG. 12 shows an amino acid sequence of KLK5 inhibitory peptide Fc fusion D0-K51028-Fc (SEQ ID NO: 6).

FIG. 13 shows an amino acid sequence of KLK5 inhibitory peptide Fc fusion D1-K51028-Fc (SEQ ID NO: 7).

FIG. 14 shows an amino acid sequence of KLK5 inhibitory peptide Fc fusion D2-K51028-Fc (SEQ ID NO: 8).

FIG. 15 shows an amino acid sequence of KLK5 inhibitory peptide Fc fusion D3-K51028-Fc (SEQ ID NO: 9).

FIG. 16 shows an amino acid sequence of KLK5 inhibitory peptide Fc fusion D4-K51028-Fc (SEQ ID NO: 10).

FIG. 17 shows an amino acid sequence of KLK5 inhibitory peptide Fc fusion D5-K51028-Fc (SEQ ID NO: 11).

FIG. 18 shows an amino acid sequence of KLK5 inhibitory peptide Fc fusion K51028-D5-Fc (SEQ ID NO: 12).

FIG. 19 shows an amino acid sequence of KLK5 inhibitory peptide Fc fusion E1-K51028-Fc (SEQ ID NO: 13).

FIG. 20 shows an amino acid sequence of KLK5 inhibitory peptide Fc fusion D1-K50055-Fc (SEQ ID NO: 14).

FIG. 21 shows a nucleotide sequence of primer 1 (SEQ ID NO: 15).

FIG. 22 shows a nucleotide sequence of primer 2 (SEQ ID NO: 16).

FIG. 23 shows a nucleotide sequence of primer 3 (SEQ ID NO: 17).

FIG. 24 shows a nucleotide sequence of primer 4 (SEQ ID NO: 18).

FIG. 25 shows a nucleotide sequence of primer 5 (SEQ ID NO: 19).

FIG. 26 shows a nucleotide sequence of primer 6 (SEQ ID NO: 20).

FIG. 27 shows a nucleotide sequence of primer 7 (SEQ ID NO: 21).

FIG. 28 shows a nucleotide sequence of primer 8 (SEQ ID NO: 22).

FIG. 29 shows a nucleotide sequence of primer 9 (SEQ ID NO: 23).

FIG. 30 shows a nucleotide sequence of primer 10 (SEQ ID NO: 24).

FIG. 31 shows a nucleotide sequence of primer 11 (SEQ ID NO: 25).

FIG. 32 shows a nucleotide sequence of primer 12 (SEQ ID NO: 26).

FIG. 33 shows a nucleotide sequence of primer 13 (SEQ ID NO: 27).

FIG. 34 shows a nucleotide sequence of primer 14 (SEQ ID NO: 28).

FIG. 35 shows a nucleotide sequence of primer 15 (SEQ ID NO: 29).

FIG. 36 shows a nucleotide sequence of primer 16 (SEQ ID NO: 30).

FIG. 37 shows a nucleotide sequence of primer 17 (SEQ ID NO: 31).

FIG. 38 shows a nucleotide sequence of primer 18 (SEQ ID NO: 32).

FIG. 39 shows a nucleotide sequence of primer 19 (SEQ ID NO: 33).

FIG. 40 shows an amino acid sequence of an Fc region of human IgG1 (SEQ ID NO: 34).

FIG. 41 shows a nucleotide sequence of primer 20 (SEQ ID NO: 35).

FIG. 42 shows a nucleotide sequence of primer 21 (SEQ ID NO: 36).

FIG. 43 shows an amino acid sequence of an Fc region of human IgG2 (SEQ ID NO: 37).

FIG. 44 shows a nucleotide sequence of primer 22 (SEQ ID NO: 38).

FIG. 45 shows a nucleotide sequence of primer 23 (SEQ ID NO: 39).

FIG. 46 shows an amino acid sequence of an Fc region of human IgG4P (SEQ ID NO: 40).

FIG. 47 shows a nucleotide sequence of primer 24 (SEQ ID NO: 41).

FIG. 48 shows a nucleotide sequence of primer 25 (SEQ ID NO: 42).

FIG. 49 shows an amino acid sequence of KLK5 inhibitory peptide Fc fusion D0-K51028-Fc (IgG2) (SEQ ID NO: 43).

FIG. 50 shows an amino acid sequence of KLK5 inhibitory peptide Fc fusion D1-K51028-Fc (IgG2) (SEQ ID NO: 44).

FIG. 51 shows an amino acid sequence of KLK5 inhibitory peptide Fc fusion D3-K51028-Fc (IgG2) (SEQ ID NO: 45).

FIG. 52 shows an amino acid sequence of KLK5 inhibitory peptide Fc fusion D0-K51028-Fc (IgG4P) (SEQ ID NO: 46).

FIG. 53 shows an amino acid sequence of KLK5 inhibitory peptide Fc fusion D1-K51028-Fc (IgG4P) (SEQ ID NO: 47).

FIG. 54 shows an amino acid sequence of KLK5 inhibitory peptide Fc fusion D3-K51028-Fc (IgG4P) (SEQ ID NO: 48).

DESCRIPTION OF EMBODIMENTS

1. Definitions

Figure 2:
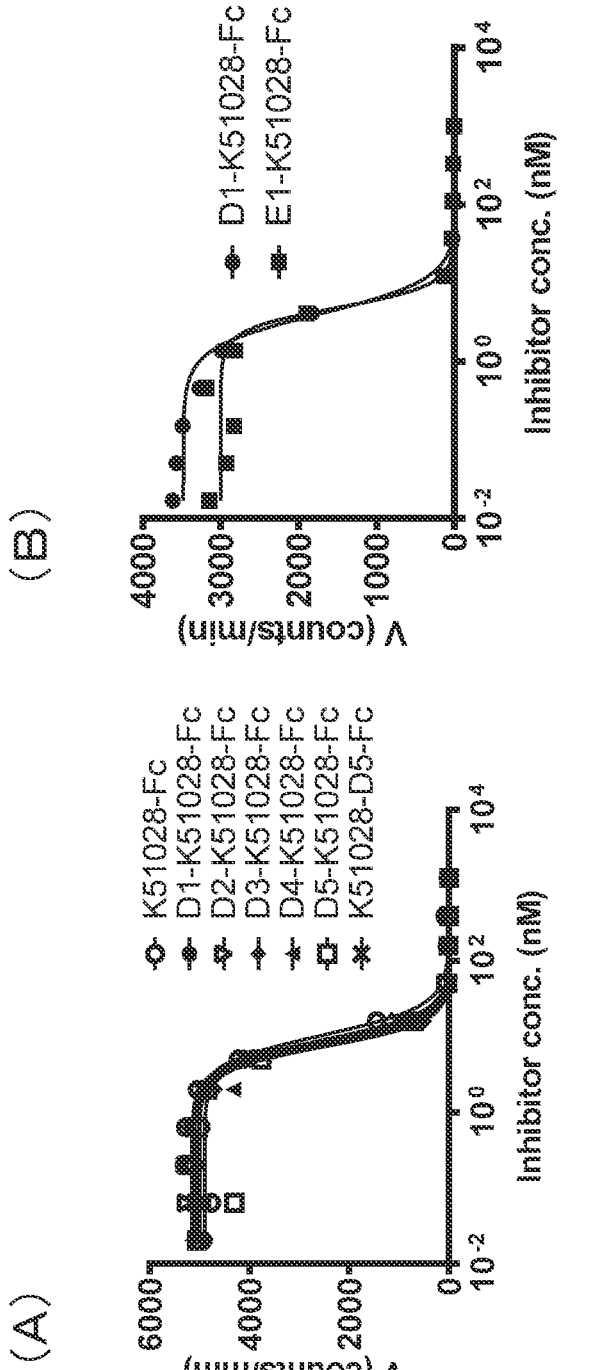
FIG. 2 is a graph showing KLK5 inhibitory activity (50% inhibitory concentration: IC50) of KLK5 inhibitory peptide Fc fusions using the degradation rate of a peptide substrate as an index. For evaluating KLK5 inhibitory activity, KLK5 at a final concentration of 20 nM and Boc-Val-Pro-Arg-AMC (R&D Systems; ES011) at a final concentration of 100 μM were used. There was no change in KLK5 inhibitory activity even when (A) one to five Asp were added or (B) Asp or Glu was added, based on K51028-Fc.

In the present invention, the term "gene" means a nucleic acid molecule containing a nucleotide sequence encoding an amino acid sequence contained in a protein, or a complementary strand thereof, and is composed of one strand, two strands, or three or more strands. The "gene" also means a complex of a DNA strand and an RNA strand, a mixture of ribonucleotides and deoxyribonucleotides in one strand, and a nucleic acid molecule of two or three or more strands including such a strand.

In the present invention, the terms "gene", "polynucleotide" and "nucleic acid molecule" have the same meaning, and are not limited at all by the number of their constitutional units such as ribonucleotides, deoxyribonucleotides, nucleotides, and nucleosides. DNA, RNA, mRNA, cDNA, cRNA, probes, oligonucleotides, primers and the like are also included in the scope of the terms. The "nucleic acid molecule" is sometimes abbreviated as a "nucleic acid".

In the present invention, the terms "polypeptide", "peptide" and "protein" have the same meaning.

In the present invention, a peptide that recognizes or binds to a target molecule X (hereinafter, the recognition or binding action thereof is collectively referred to as "X binding activity") can be referred to as an "X binding peptide". Furthermore, a peptide that recognizes or binds to a target molecule X, and inhibits or suppresses one or two or more activities or functions of the target molecule X (hereinafter, the inhibition or suppression action thereof is collectively referred to as "X inhibitory activity") can be referred to as an "X inhibitory peptide".

In the present invention, the term "SPINK2" means Serine Protease Inhibitor Kazal-type 2, which is a 7 kDa protein composed of a Kazal-like domain having three disulfide bonds. Preferable SPINK2 is SPINK2 derived from a human. In the present invention, human SPINK2 (SEQ ID NO: 1, FIG. 7) is simply referred to as "SPINK2", unless otherwise specified.

In the present invention, the "site" to which a peptide binds, in other words, the "site" recognized by the peptide, means a contiguous or intermittent partial amino acid sequence or partial higher order structure on a target molecule to which the peptide binds or recognized by the peptide. In the present invention, such a site can be referred to as an epitope or binding site on the target molecule.

In the present invention, the term "cell" includes various cells derived from an individual animal, a passage cultured cell, a primary cultured cell, a cell line, and a recombinant cell, a yeast, a microorganism, and the like.

In the present invention, the term "SPINK2 variant" is a peptide having an amino acid sequence in which one or two or more amino acids are substituted with an amino acid different from the wild-type, one or two or more amino acids are deleted from the wild-type, or one or two or more non-wild-type amino acids are inserted (hereinafter collectively referred to as "mutation") in an amino acid sequence of the wild-type SPINK2.

In the present invention, the term "several" in "one to several" refers to 3 to 10.

In the present invention, the term "hybridize under stringent conditions" means hybridizing under the conditions of performing hybridization at 65° C. in a solution containing 5×SSC, and then washing in an aqueous solution containing 2×SSC-0.1% SDS at 65° C. for 20 minutes, in an aqueous solution containing 0.5×SSC-0.1% SDS at 65° C. for 20 minutes, and in an aqueous solution containing 0.2×SSC-0.1% SDS at 65° C. for 20 minutes, respectively, or under equivalent conditions thereto. SSC represents an aqueous solution of 150 mM NaCl-15 mM sodium citrate, and n×SSC means n-fold concentration SSC.

The terms "specific" and "specificity" in the present invention are synonymous with "selective" and "selectivity", respectively, and they are interchangeable.

The term "blood kinetics" refers to pharmacokinetics in blood circulation, that is, kinetics in (such as uptake and distribution) and elimination from (such as metabolism and excretion) blood circulation of a drug administered to an individual over time, and is evaluated using a change in blood drug concentration over time (PK), blood exposure amount (AUC), drug elimination half-life ($t_{1/2}$), maximum blood drug concentration ($C_{max}$), time to reach maximum blood concentration ($t_{max}$) or the like as an index.

The term "blood exposure amount" means a numerical value expressing the blood drug concentration for a certain time by means of the area under the blood concentration-time curve.

The term "blood kinetics improvement" means suppression of decrease of blood drug concentration over time, extension of PK, increase of AUC, extension of $t_{1/2}$, increase of $C_{max}$, and/or shortening of $t_{max}$.

2. Peptide 2-1. Amino Acid

The term "amino acid" is an organic compound containing an amino group and a carboxyl group, and it preferably means an α-amino acid included in a protein, more preferably in a native protein, as a constitutional unit. In the present invention, more preferable amino acids are Ala, Arg, Asn, Asp, Cys, Gln, Glu, Gly, His, Ile, Leu, Lys, Met, Phe, Pro, Ser, Thr, Trp, Tyr, and Val. The term "amino acid" means these 20 amino acids in total, unless otherwise specified. Those 20 amino acids in total can be referred to as "natural amino acids".

In the present invention, the term "amino acid residue" is sometimes abbreviated as an "amino acid".

In the present invention, an amino acid is an L-amino acid, a D-amino acid, or a mixture of these (DL-amino acid), but unless otherwise specified, the amino acid means an L-amino acid.

Natural amino acids can be classified based on the nature of their common side chains into, for example, the following groups.

(1) Hydrophobic amino acid group: Met, Ala, Val, Leu, Ile
(2) Neutral hydrophilic amino acid group: Cys, Ser, Thr, Asn, Gln
(3) Acidic amino acid group: Asp, Glu
(4) Basic amino acid group: His, Lys, Arg
(5) Group of amino acids that have an effect on the orientation of the backbone: Gly, Pro
(6) Aromatic amino acid group: Trp, Tyr, Phe However, the classification of natural amino acids is not limited to these.

In the present invention, natural amino acids may undergo conservative amino acid substitutions.

The term "conservative amino acid substitution" means a substitution with a functionally equivalent or similar amino acid. Conservative amino acid substitutions in the peptide result in a static change in the amino acid sequence of the peptide. For example, one or two or more amino acids having similar polarity act functionally equivalently, thus a conservative amino acid substitution results in a static change in the amino acid sequence of the peptide. In general, substitutions with amino acids within a group can be considered conservative in structure and function. However, as will be apparent to those skilled in the art, the role played by a particular amino acid residue may be determined in the three-dimensional structure of a molecule containing the amino acid. For example, cysteine residues can take the oxidized (disulfide) form, which has less polarity compared to the reduced (thiol) form. Long aliphatic moieties of arginine side chains can constitute structurally and functionally important features. Side chains containing aromatic rings (tryptophan, tyrosine, phenylalanine) can also contribute to ion-aromatic interactions or cation-pi interactions. In such cases, even if amino acids having these side chains are substituted with amino acids belonging to acidic or nonpolar groups, they may be structurally and functionally conservative. Residues such as proline, glycine, and cysteine (disulfide form) can have a direct effect on the backbone conformation, thus they often cannot be substituted without structural distortion.

Conservative amino acid substitutions include specific substitutions based on side chain similarity as shown below (L. Lehninger, Biochemistry, revised $2^{nd}$ edition, pp 73-75, Worth Publisher, New York (1975)) and other typical substitutions.

(1) Nonpolar amino acid group: alanine (hereinafter referred to as "Ala" or simply "A"), valine (hereinafter referred to as "Val" or simply "V"), leucine (hereinafter referred to as "Leu" or simply "L"), isoleucine (hereinafter referred to as "Ile" or simply "I"), proline (hereinafter referred to as "Pro" or simply "P"), phenylalanine (hereinafter referred to as "Phe" or simply "F"), Tryptophan (hereinafter referred to as "Trp" or simply "W"), and methionine (hereinafter referred to as "Met" or simply "M");

(2) Uncharged polar amino acid group: glycine (hereinafter referred to as "Gly" or simply "G"), serine (hereinafter referred to as "Ser" or simply "S"), threonine (hereinafter referred to as "Thr" or simply "T"), cysteine (hereinafter referred to as "Cys" or simply "C"), tyrosine (hereinafter referred to as "Tyr" or simply "Y"), asparagine (hereinafter referred to as "Asn" or simply "N"), and glutamine (hereinafter referred to as "Gln" or simply "Q");

(3) Acidic amino acid group: aspartic acid (hereinafter referred to as "Asp" or simply "D"), and glutamic acid (hereinafter referred to as "Glu" or simply "E");

(4) Basic amino acid group: lysine (hereinafter referred to as "Lys" or simply "K"), arginine (hereinafter referred to as "Arg" or simply "R"), and histidine (hereinafter referred to as "His" or simply "H").

In the present invention, the amino acid may be an amino acid other than a natural amino acid. Examples of such an amino acid can include selenocysteine, N-formylmethionine, pyrrolidine, pyroglutamic acid, cystine, hydroxyproline, hydroxylysine, thyroxine, O-phosphoserine, desmosine, β-alanine, sarcosine, ornithine, creatine, γ-aminobutyric acid, opain, theanine, tricolominic acid, kainic acid, domoic acid and achromeic acid found in natural peptides and proteins. Further examples can include N-terminus protected amino acids such as norleucine, Ac-amino acid, Boc-amino acid, Fmoc-amino acid, Trt-amino acid and Z-amino acid; C-terminus protected amino acid such as amino acid t-butyl ester, benzyl ester, cyclohexyl ester, and fluorenyl ester; and other amino acids not found in the natural world including diamine, ω-amino acid, β-amino acid, γ-amino acid, Tic derivative of amino acid, and aminophosphonic acid. Without limiting to these, amino acids other than the 20 "natural amino acids" described above are collectively referred to as "non-natural amino acids" in the present invention, for convenience.

2-2. Peptide

As used herein, a peptide is not particularly limited as long as it is a wild-type, a variant, or a modified version of any peptide, an artificially designed peptide, or the like, but is preferably a peptide that binds to, activates, promotes, suppresses or inhibits the activity of, and/or antagonizes or agonizes, a target molecule. A more preferable peptide is a SPINK2 variant.

In the present invention, the term "target molecule" means an endogenous substance in humans or non-human animal individuals or an exogenous substance that can be incorporated into a living body, to which the peptide of the present invention binds. When the peptide is a SPINK2 variant, the target molecule of the present invention is preferably a molecule other than trypsin and/or acrosin which are endogenous targets of SPINK2, more preferably a molecule other than trypsin, even more preferably a molecule from humans other than trypsin from humans. Still more preferably, it is an endogenous or exogenous enzyme, receptor, ligand of the receptor, liquid factor such as a cytokine, other biomacromolecules, signal transducer, cell, pathogen, or toxin, or a substance derived from any one or more of these, e.g., a fragment, a degradation product, a metabolite, a processed product, or the like, which may be directly or indirectly involved in the development or progression of a disease from which a human individual may suffer, or which is correlated or inversely correlated with such disease (hereinafter referred to as a "disease-related target molecule"). In one embodiment of the present invention, a preferable target molecule is a protease other than trypsin and/or acrosin, more preferably a protease other than trypsin. Such a protease is preferably a disease-related target molecule.

A peptide that binds to and/or activates, promotes or suppresses the activity of, and/or antagonizes or agonizes a target molecule can be identified or concentrated from a peptide library by performing a screening method well known to those skilled in the art (WO2014/024914A1, WO2018/117244A1) using the activity of binding to the target molecule, the activity of activating, promoting, suppressing or inhibiting the target molecule, and/or the activity of antagonizing or agonizing the target molecule (collectively referred to as an "activity against the target molecule") as an index. The amino acid sequence of the identified or concentrated peptide can be determined with sequences known in the art. A peptide in which the amino acid sequence is determined can be prepared by recombination, chemical synthesis, or in vitro translation.

Examples of the disease-related target molecule can include, but are not limited to, chymotrypsin, kallikrein, EGFR, HER2, KLK1, KLK4, KLK5, KLK8, HTRA1, and MMP-9.

Examples of the SPINK2 variant peptide having an activity against the disease-related target molecule can include, but are not limited to, a chymotrypsin binding peptide (WO2014/024914A1); a kallikrein binding peptide, an EGFR binding peptide and a HER2 binding peptide (WO2014/024914A1); K50055 (SEQ ID NO: 4, FIG. 10) and K51028 (SEQ ID NO: 5, FIG. 11), which are peptides that inhibit the protease activity of human KLK5 (hereinafter referred to as "KLK5 inhibitory peptide"); a HTRA1 inhibitory peptide (WO2018/117244A1); a MMP-9 binding peptide (WO2019/017338A1); and a KLK1 inhibitory peptide, a KLK4 inhibitory peptide, and/or a KLK8 inhibitory peptide (WO2019/049933A1).

KLK5 is a protein exhibiting a trypsin-like protease activity, which is composed of an N-terminus propeptide and a protease catalytic domain and has three N-type glycochain additions. KLK5 is preferably human KLK5 (SEQ ID NO: 3, FIG. 9). A KLK5 inhibitor is useful for the treatment and/or prevention of Netherton syndrome, atopic dermatitis, rosacea, skin injury due to ultraviolet radiation, psoriasis, asthma, spinal cord injury, cancer, Barrett esophagus, and the like. It should be noted that K51028 also inhibits the protease activity of human KLK7 (data not shown).

The SPINK2 variant having an activity against a disease-related target molecule has advantages in that it has a smaller molecular weight than other biomacromolecules such as antibodies used in the field as pharmaceuticals and diagnostic agents; its production is relatively easy; it is excellent in terms of physical properties such as storage stability and heat stability; and it has a wide selection of administration routes, administration methods, formulations, or the like when used in a pharmaceutical composition. The molecular weight of the SPINK2 variant peptide is less than 10,000, preferably less than 8,000, more preferably about 7,000 to 7,200. A variable loop portion consisting of Cys15 to Cys31 or a peptide fragment consisting of Cys15 to Cys63 of SEQ ID NO: 2 (FIG. 8) (hereinafter referred to as a "portion containing 6 Cys") is included in the scope of the peptide of the present invention. The molecular weight of the variable loop portion is less than 2,500, preferably about 1,800 to 2,000, and the molecular weight of the portion containing 6 Cys is less than 6,000, preferably about 5,300 to 5,500. It is also possible to adjust the blood half-life of the peptide to be longer when using the peptide in a pharmaceutical composition by increasing the molecular weight of the peptide of the invention by known methods such as by addition of biomacromolecules or polymers.

In the present invention, the term "mutated" means that a substitution, a deletion or an insertion of one or two or more nucleotides or nucleotide residues or amino acids or amino acid residues has been made in a nucleotide sequence or an amino acid sequence compared to a naturally occurring nucleic acid molecule or peptide. The amino acid sequence of the SPINK2 variant of the present invention has one or two or more mutated amino acids or amino acid residues as compared to the amino acid sequence of human SPINK2.

In one embodiment of the present invention, the amino acid sequence of the SPINK2 variant is one in which, in the amino acid sequence of human SPINK2 (SEQ ID NO: 1, FIG. 7),
one, two, three, four, five, six, or seven amino acids of Ser16 to Gly22 are substituted with other amino acids or amino acid residues; and
one, two, three, four, or five amino acids of Pro24 to Asn28 are substituted with other amino acids or amino acid residues; and Cys15, Cys23, Cys31, Cys42, Cys45 and Cys63 are preferably Cys as in the wild-type in order to maintain the natural disulfide bonds, but one, two, three, four, five or six of them can be replaced with other amino acids in order to eliminate natural disulfide bonds or generate unnatural disulfide bonds. In the SPINK2 variants, Cys residues are maintained at the same 6 positions as the natural type, thus the disulfide bonds are maintained. In some more preferable embodiments among such peptides, it is preferable that Cys15-Cys45, Cys23-Cys42, and Cys31-Cys63 form a disulfide bond, respectively, and a conformation composed of a loop structure consisting of Ser16 to Val30, a β sheet composed of a β strand (1) consisting of Cys31 and Gly32 and a β strand (2) consisting of Ile57 to Arg59, an α helix consisting of Glu41 to Gly51, or a loop structure, a β sheet, an α helix, or the like similar to those or at least partially corresponding to those (or to the positions of those), which is contained in the amino acid sequence of the wild-type SPINK2, is maintained to the extent that the activity against the target molecule can be effected.

3. Introduction of Change or Mutation into Peptide

Variants of a peptide (or conjugate: described below) in which one or two or more (e.g., one to several) amino acids are deleted, substituted, added or inserted in the amino acid sequence of the peptide (or conjugate) of the present invention, and variants of a peptide (or a conjugate) having an amino acid sequence that is 80%, 85%, 90%, 95%, 98%, or 99% or more identical to the amino acid sequence of the original peptide (or conjugate) are also included in the scope of the peptide (or conjugate) of the present invention, and preferable peptide (or conjugate) variants maintain some or all of the activity of the original peptide (or conjugate) against a target molecule.

Peptides having one or two or more (e.g., one to several) amino acid substitutions, additions and/or deletions at the amino terminus and/or carboxyl terminus of the peptide of the present invention and maintaining some or all of the activity of the original peptide against a target molecule are also included in the scope of the peptide of the present invention.

In the amino acid sequence of the SPINK2 variant of the present invention, the portions other than $X_1$ to $X_{12}$ of SEQ ID NO: 2 (FIG. 8), i.e., positions of Pro2 to Cys15, Cys23 and Pro29 to Cys63 in the amino acid sequence of the wild-type human SPINK2 (SEQ ID NO: 1, FIG. 7) can include a naturally occurring amino acid or a mutated amino acid or an amino acid sequence. For example, a SPINK2 variant may be mutated at any one or two or more (e.g., one to several) positions as long as the mutation does not completely hinder or interfere with the activity against the target molecule or its folding. Such mutations may be made by using standard methods known to those skilled in the art. Typical mutations in the amino acid sequence can include substitution, deletion, or insertion of one or two or more (e.g., one to several) amino acids, and examples of the substitution can include a conservative substitution. With a conservative substitution, a certain amino acid residue is substituted by another amino acid residue that has similar chemical characteristics not only in bulkiness but also in polarity. Examples of a conservative substitution are described elsewhere in the description. Meanwhile, non-conservative substitutions of one or two or more (e.g., one to several) amino acids may be allowed in the portions other than $X_1$ to $X_{12}$ as long as the substitution does not completely hinder or interfere with the activity against the target molecule or folding.

Accordingly, the amino acid sequence, which the peptide contained in a peptide or conjugate (described below) to which the blood kinetics improvement method of the present invention may be applied has, may be any of the following: (a1) an amino acid sequence consisting of an amino acid sequence consisting of SEQ ID NO: 2 (FIG. 8); (a2) an amino acid sequence having 1 to 20, 1 to 15, 1 to 10, 1 to 8, 1 to 6, 1 to 5, 1 to 4, 1 to 3, 1 to 2, or 1 amino acid substitutions, deletions, additions and/or insertions in the amino acid sequence consisting of SEQ ID NO: 2 (FIG. 8) and contained in a peptide maintaining some or all of the activity of a peptide containing the amino acid sequence described in (a1) against a target molecule; (a3) an amino acid sequence encoded by a nucleotide sequence that hybridizes with a nucleotide sequence complementary to a nucleotide sequence encoding the amino acid sequence consisting of SEQ ID NO: 2 (FIG. 8) under stringent conditions and encodes an amino acid sequence contained in a peptide maintaining some or all of the activity of a peptide containing the amino acid sequence described in (a1) against a target molecule; and (a4) an amino acid sequence that is 60%, 70%, 80%, 85%, 90%, 92%, 94%, 96%, 97%, 98%, or 99% or more identical to the amino acid sequence consisting of SEQ ID NO: 2 (FIG. 8) and contained in a peptide maintaining some or all of the activity of a peptide containing the amino acid sequence described in (a1) against a target molecule, but the amino acid sequence contained in a peptide or conjugate is not limited to these.

Mutations can be introduced into the peptide, in order to improve folding stability, heat stability, storage stability, water solubility, biological activity, pharmacological activity, side effects, or the like. For example, a new reactive group such as Cys can be introduced by mutation to conjugate with polyethylene glycol (PEG), hydroxyethyl starch (HES), biotin, or the like.

4. Conjugate Containing Peptide

In the present invention, the peptide may be fused with, conjugated with or added to another moiety, and the form of such fusion, conjugation or addition is referred to as a "conjugate of a peptide". In the present invention, the "conjugate" means a molecule in which the peptide or a fragment thereof is bound to another moiety. The "conjugate" or "conjugation" include a form in which the peptide is conjugated with or bound to a certain moiety via a chemical substance such as a cross-linking agent, or via an agent suitable for linking to a side chain of an amino acid, or by a synthetic chemical or genetic engineering technique to the N-terminus and/or C-terminus of the peptide. Examples of such a "moiety" for improving blood half-life can include polyalkylene glycol molecules such as polyethylene glycol (PEG); a fatty acid molecule such as hydroxyethyl starch or palmitic acid; an Fc region of immunoglobulin; a CH3 domain of immunoglobulin; a CH4 domain of immunoglobulin; albumin or a fragment thereof; an albumin-binding peptide; an albumin-binding protein such as streptococcal protein G; and transferrin. As another example of the "moiety", such a "moiety" may be linked to the peptide of the present invention via a linker, such as a peptide linker.

In one embodiment of the present invention, the conjugate is a fusion of a SPINK2 variant peptide with an Fc region or a fragment thereof of an antibody. Examples of origins of the antibody can include human and non-human animals such as rodents, e.g., mouse, rat, and rabbit; other mammals, e.g., cow, pig, dog, cynomolgus monkey, and rhesus monkey; and birds, e.g., chicken, and is preferably human. Examples of the antibody can include IgG1, IgG2, IgG3, IgG4, IgM, IgA1, IgA2, IgD, and IgE, and is preferably IgG1. More preferably, the conjugate is a fusion of the peptide of the present invention with an Fc region or a fragment thereof of human IgG1. A fusion of the peptide of the present invention with an Fc region or a fragment thereof of an antibody is sometimes referred to as an "Fc fusion" or "Fc conjugate", and they are synonymous.

Examples of the Fc region of human IgG1 can include, but are not limited to, those containing or consisting of an amino acid sequence represented by SEQ ID NO: 34 (FIG. 40) or a fragment thereof. The Fc region or a fragment thereof of an antibody may be either a wild-type or a variant.

It is possible to modulate the effector function by substituting a portion of amino acid residues in the Fc region of an antibody (see WO88/007089, WO94/28027, WO94/29351). Examples of such IgG1 variants that have attenuated effector function include IgG1 LALA (IgG1-L234A, L235A) and IgG1 LAGA (IgG1-L235A, G237A). Among human IgG subclasses of five types, human IgG2 is very weak in effector function such as CDC activity via complement binding or antibody-dependent cytotoxic activity (Bruggemann et al., J. Exp. Med., 1351-1361, 1987). Among human IgG subclasses of five types, human IgG4 is very weak in effector function such as CDC activity via complement binding or antibody-dependent cytotoxic activity (Bruggemann et al., J. Exp. Med., 1351-1361, 1987). When IgG4 is used, it is possible to suppress IgG4-specific fragmentation and extend the half-life by substituting a portion of amino acid residues in the constant region (Mol. Immunol., 30, 105-108, 1993). Examples of IgG4 variants include IgG4P (IgG4-S241P) and IgG4P FALA (IgG4-S241P, F234A, L235A). Human IgG4P refers to a variant in which the 241st serine residue of human IgG4, which is involved in H2L2 tetramer formation by binding between H chains, is substituted with proline to have a sequence similar to human IgG1 and human IgG2, thereby having suppressed H2L2 tetramer formation and increased stability in blood (Angal et al., Mol. Immunol., 30, 105-108, 1993). IgG4P FALA has further attenuated effector function by substituting two amino acid residues necessary for interaction with FcγRIII present in the CH2 domain with alanine (Parekh et al., MAbs, 310-318, 2012). Artificially modified Fc regions as well as polymorphisms of naturally occurring Fc region sequences are also included in the scope of the "variant".

The conjugate may be a fusion of a peptide other than a SPINK2 variant peptide with an Fc region or a fragment thereof of an antibody. Examples of such conjugates include a conjugate of an extracellular domain protein of human Tumor Necrosis Factor II Receptor (TNFR) with Fc (etanercept); a conjugate of an extracellular domain protein of human Cytotoxic T Lymphocyte-associated Antigen 4 (CTLA4) with Fc (abatacept); a conjugate of an extracellular domain protein of human Vascular Endothelial Growth Factor Receptor (VEGFR) with Fc (aflibercept); a conjugate of human blood coagulation factor VIII with Fc (Efralocto-cog Alfa); a conjugate of human blood coagulation factor VIII with Fc (Eftrenonacog Alfa); a conjugate of human thrombopoietin receptor binding peptide with Fc (romiplostim); and a conjugate of a human Glucagon-Like Peptide-1 (GLP-1) analog with Fc (dulaglutide).

In an embodiment, examples of the peptide contained in the conjugate include, but are not limited to, Atrial Natriuretic Peptide (ANP), Leptin, Interleukin-2 (IL-2), IL-22, Secretin, Beta-endorphin, GLP-1, and Fibroblast Growth Factor-2 (FGF-2).

In an embodiment, the peptide contained in the conjugate may be an antigen-binding fragment of an antibody. In the present invention, an "antigen-binding fragment of an antibody" means a partial fragment of an antibody that maintains a function of recognizing an antigen, and has the same meaning as a "functional fragment of an antibody". Examples of an antigen-binding fragment of an antibody can include, but are not limited to, Fab, F(ab')2, scFv, Fab', and a single-chain immunoglobulin. The functional fragment of such an antibody may be a fragment obtained by treating a full-length molecule of an antibody with an enzyme such as papain or pepsin, or may be a recombinant protein produced in an appropriate host cell using a recombinant gene.

In an Fc conjugate of a peptide such as a SPINK2 variant, the peptide may be located at the amino terminus end of the Fc region or the fragment thereof, or the Fc region may be located at the amino terminus end of the peptide, but the former is preferable. The peptide and the Fc region or the fragment thereof may be directly fused, or may be indirectly fused via a linker or the like. The linker is a peptide and/or a non-peptide. The Fc conjugate of a peptide such as a SPINK2 variant may also include another peptide or non-peptide, in addition to the peptide, the Fc region or the fragment thereof, and an optional intervening moiety (such as a linker) between the two.

The peptide may be conjugated to another drug to exert or enhance pharmacological activity. Techniques and embodiments known to those skilled in the art for antibody-drug conjugates (ADCs) in the field of antibodies can become a part of the present invention by replacing the antibody with the peptide of the present invention.

Furthermore, the peptide may further contain one or two or more moieties that exhibit an activity for another target molecule, or may be conjugated to such a moiety. Examples of such a "moiety" can include an antibody or a fragment thereof, and a protein having a scaffold other than an antibody, such as a SPINK2 variant, or a fragment thereof. Techniques and embodiments known to those skilled in the art for a multi-specific antibody and a bi-specific antibody in the field of antibodies can become a part of the embodiment of the conjugate of the present invention by substituting at least one of two or more "antibodies" included in the aforesaid with the peptide of the present invention.

The peptide or a precursor thereof may contain a signal sequence. A signal sequence present at or added to the N-terminus of a peptide or a precursor thereof is useful to deliver the peptide to a specific compartment of a cell, for example, the periplasm in *E. coli* or the endoplasmic reticulum in a eukaryotic cell. Many signal sequences are known to those of skill in the art and can be selected depending on the host cell. Examples of the signal sequence for secreting a desired peptide into the periplasm of *E. coli* can include OmpA. Conjugates having a form containing a signal sequence are also included in the scope of the present invention.

Furthermore, by adding a tag to the peptide in advance, the peptide can be purified by affinity chromatography. For example, the peptide may have, at the C-terminus, biotin, a Strep-Tag®, a Strep-tag II®, an oligohistidine such as His6, a polyhistidine, an immunoglobulin domain, a maltose binding protein, glutathione-S-transferase (GST), a calmodulin-binding peptide (CBP), a hapten such as digoxigenin or dinitrophenol, an epitope tag such as FLAG®, a myc tag, a HA tag, or the like (hereinafter collectively referred to as an "affinity tag"). Tag adducts may also be included in some embodiments of the conjugate of the present invention. The conjugate of the present invention may be a peptide (polypeptide) as a whole.

The peptide may contain a moiety for labeling. Specifically, a moiety for labeling such as an enzyme label, a radioactive label, a coloring label, a fluorescent label, a chromogenic label, a luminescent label, a hapten, digoxigenin, biotin, a metal complex, a metal, colloidal gold or the like may be conjugated. Those containing a moiety for labeling are also included in the scope of the conjugate of the present invention.

Furthermore, the peptide (or the amino acid sequence thereof) can contain a naturally occurring amino acid and/or an unnaturally occurring amino acid, where the naturally occurring amino acid may be an L-amino acid or a D-amino acid.

The peptide may also be present as a monomer, dimer, trimer or higher oligomer, or as a multimer. The dimer, trimer or higher oligomer and the multimer may be either a homopolymer composed of a single monomer or a heteropolymer composed of two or more different monomers. Monomers may, for example, diffuse rapidly and have excellent penetration into tissues. Dimers, oligomers and multimers may have advantages in some aspects, for example, they may have a slow dissociation rate that is superior locally in an activity against the target molecule. In addition to a spontaneous dimerization, oligomerization or multimerization, an intended dimerization, oligomerization or multimerization can also be conducted by introducing a jun-fos domain, a leucine zipper, or the like into the peptide of the present invention.

Furthermore, the peptide can exert an activity on one or two or more target molecules as a monomer, dimer, trimer or higher oligomer, or a multimer.

The peptide can be in an isolated form (such as a lyophilized preparation or a solution), a conjugate form as described above, or a form bound to another molecule (such as a solid-phase form, a form associated with a different molecule, or a form bound to a target molecule), but is not limited to these, and can take any form suitable for expression, purification, use, storage, or the like.

Examples of the amino acid sequence of the SPINK2 variant contained in the conjugate of the present invention having improved blood kinetics can include the amino acid sequences (a1), (a2), (a3) and (a4) described above. In the amino acid sequences of the SPINK2 variant Fc conjugate of the present invention having improved blood kinetics, the amino acid sequences except for one or two or more, preferably one to several, amino acids added to the amino terminus are not limited when they include the amino acid sequence (a1), (a2), (a3) or (a4) described above as the amino acid sequence of the SPINK2 variant, and an amino acid sequence of an Fc region or a fragment thereof of the various Ig described above as the amino acid sequence of the Fc region of an antibody. Examples of such amino acid sequences can include the following: (b1) an amino acid sequence containing an amino acid sequence consisting of SEQ ID NO: 2 (FIG. 8) and an amino acid sequence of an Fc region of human IgG1 (e.g., SEQ ID NO: 34, FIG. 40); (b2) an amino acid sequence having 1 to 20, 1 to 15, 1 to 10, 1 to 8, 1 to 6, 1 to 5, 1 to 4, 1 to 3, 1 to 2, or 1 amino acid substitutions, deletions, additions and/or insertions in the amino acid sequence described in (b1) and contained in a peptide or conjugate maintaining some or all of the activity of a conjugate containing the amino acid sequence described in (b1) against a target molecule; (b3) an amino acid sequence encoded by a nucleotide sequence that hybridizes with a nucleotide sequence complementary to the nucleotide sequence encoding the amino acid sequence described in (b1) under stringent conditions and encodes an amino acid sequence contained in a peptide or conjugate maintaining some or all of the activity of a conjugate containing the amino acid sequence described in (b1) against a target molecule; and (b4) an amino acid sequence that is 60%, 70%, 80%, 85%, 90%, 92%, 94%, 96%, 97%, 98%, or 99% or more identical to the amino acid sequence described in (b1) and is contained in a peptide or conjugate maintaining some or all of the activity of a conjugate containing the amino acid sequence described in (b1) against a target molecule.

5. Improved Blood Kinetics of Peptide or Conjugate

The present invention provides a method for improving blood kinetics of a peptide or a peptide-containing conjugate. The peptide may be a peptide in which one or two or more, preferably one to several amino acids (which may be amino acids other than natural amino acids) may be further added to the amino terminus end of the first amino acid, i.e., the amino acid at the amino terminus, of the amino acid sequence of the peptide (that includes a peptide contained in a conjugate, and preferably has an activity against a disease-related target molecule) of the present invention. Examples of such an amino acid addition can preferably include those in which one to several acidic amino acids, more preferably Asp and/or Glu, have been added (which may include both of Asp and Glu), even more preferably one to several Asp have been added or one to several Glu have been added. The number of additional amino acids, such as Asp and/or Glu, is preferably 1 to 5, or 1 to 4, more preferably 1 to 3, even more preferably 2 or 3, and most preferably 3.

Such addition of amino acids to the amino terminus may improve blood kinetics of a peptide or conjugate. The improvement in blood kinetics is not particularly limited as long as it is an improvement in an index indicating that kinetics in (such as uptake or distribution) and elimination from (such as metabolism or excretion) blood circulation over time of the peptide or conjugate administered to an individual have improved, but preferably, suppression of blood drug concentration decrease over time (also referred to as "extension of PK"), increase in blood exposure amount (AUC), increase in drug elimination half-life ($t_{1/2}$), increase in maximum blood drug concentration ($C_{max}$), and/or shortening in time to reach maximum blood concentration ($t_{max}$), more preferably suppression of blood drug concentration decrease over time (extension of PK) or increase in blood exposure amount (AUC). To the amino terminus of a conjugate in which the Fc region of the antibody or a fragment thereof is fused to a peptide such as a SPINK2 variant (preferably, the Fc region is located at the carboxyl terminus end of the peptide), one or two or more, one to several, one to five, or one to four, more preferably one to three, even more preferably two or three, and most preferably three amino acids may be added, where preferable amino acids are Asp and/or Glu, more preferably Asp or Glu, even more preferably three Asp or three Glu, most preferably three Asp. Such amino acid-added forms are included in the conjugate of the present invention.

If one or two or more, preferably one to several amino acids, preferably Asp and/or Glu are added to the amino terminus of the peptide or conjugate (preferably, an Fc fusion), although the peptide or conjugate becomes locally negatively charged, this is without significantly affecting the isoelectric point (pI) of the peptide or conjugate, and it is possible to suppress blood concentration decrease of the peptide or conjugate at an early stage after administration, and maintain its blood concentration higher for a longer period of time compared to the original peptide or conjugate. Because the addition of negatively charged amino acids does not significantly affect the pI of the peptide or conjugate, the effect on biological or pharmacological activity, physicochemical properties or the like, not just blood kinetics, can be minimized.

The present invention also provides a peptide and a conjugate having improved blood kinetics. Examples can include a conjugate having one Asp added (D1-K51028-Fc, SEQ ID NO: 7, FIG. 13; D1-K50055-Fc, SEQ ID NO: 14, FIG. 20; D1-K51028-Fc (IgG2), SEQ ID NO: 44, FIG. 50; D1-K51028-Fc (IgG4P); SEQ ID NO: 47, FIG. 53), a conjugate having two Asp added (D2-K51028-Fc, SEQ ID NO: 8, FIG. 14), a conjugate having three Asp added (D3-K51028-Fc, SEQ ID NO: 9, FIG. 15; D3-K51028-Fc (IgG2), SEQ ID NO: 45, FIG. 51; D3-K51028-Fc (IgG4P), SEQ ID NO: 48, FIG. 54); a conjugate having four Asp added (D4-K51028-Fc, SEQ ID NO: 10, FIG. 16); a conjugate having five Asp added (D5-K51028-Fc, SEQ ID NO: 11, FIG. 17); and a conjugate having one Glu added (E1-K51028-Fc, SEQ ID NO: 13, FIG. 19). The conjugates having improved blood kinetics, however, are not limited to these, and by applying the above blood kinetics improvement method to a peptide (preferably an Fc fusion of the peptide) having activity against any target molecule, the blood kinetics of the peptide having the desired pharmacological activity can be improved, and a peptide or conjugate having improved blood kinetics can be obtained.

6. Preparation of Peptide or Conjugate

The present invention also provides a polynucleotide containing a nucleotide sequence encoding an amino acid sequence contained in a peptide or a conjugate containing the peptide (hereinafter referred to as a "coding gene"), a recombinant vector into which the coding gene has been inserted, a cell into which the gene or vector has been introduced (hereinafter referred to as a "coding gene-containing cell"), a cell producing the peptide or conjugate (hereinafter simply referred to as a "producing cell"), and a method for producing a peptide or conjugate, comprising a step of culturing the coding gene-containing cell or producing cell.

To design a nucleotide sequence encoding an amino acid sequence, one or two or more codons corresponding to each amino acid can be used. Thus, the nucleotide sequence encoding a single amino acid sequence possessed by a certain peptide can have a plurality of variations. Upon selecting such codons, the codon can be appropriately selected according to the codon usage of the host cell for expression into which a polynucleotide having the nucleotide sequence or a vector containing the same is introduced, and the frequency or ratio of the use of multiple codons can be adjusted appropriately. For example, when *E. coli* is used as a host cell, a nucleotide sequence may be designed using codons that are frequently used in *E. coli*.

A coding gene may be operably linked to one or two or more regulatory sequences. The term "operably linked" means that it allows the expression of the coding gene linked or allows the expression of the nucleotide sequence contained in the coding gene. The regulatory sequences include sequence elements having information about transcriptional and/or translation regulation. The regulatory sequence varies from species to species, but generally includes a promoter, and includes 5' non-coding sequences involved in transcription and translation initiation, such as prokaryotic −35/−10 boxes and a Shine Dalgarno sequence, and a eukaryotic TATA box, a CAAT sequence, and a 5' capping sequence. Such a sequence may include an enhancer element and/or a repressor element as well as a signal sequence, a leader sequence, or the like, which can be translated, to deliver native or mature peptides to specific compartments inside or outside of the host cell. Furthermore, the regulatory sequence may contain a 3' non-coding sequence, and such a sequence may include elements involved in transcriptional termination, polyadenylation, or the like. However, if the sequence for transcriptional termination does not function sufficiently in a particular host cell, it can be replaced with a sequence suitable for the cell.

Examples of the promoter sequence can include a tet promoter, a lacUV5 promoter, a T7 promoter or the like in prokaryotes, and a SV40 promoter, a CMV promoter or the like in eukaryotic cells.

The coding gene may be, but is not limited to, an isolated form, or a form contained in a vector or other cloning vehicle (hereinafter simply referred to as a "vector", which includes a plasmid, a phagemid, a phage, a baculovirus, a cosmid, or the like) or a form contained in a chromosome. The vector may include, in addition to the above regulatory sequences, a replication sequence and a control sequence suitable for the host cell used for expression, and a selection marker that provides a selectable phenotype to a cell into which a nucleic acid molecule is introduced by transformation or the like.

A coding gene or a vector containing the coding gene can be introduced into a host cell capable of expressing the gene or a peptide that is a translation product thereof by a method known to those skilled in the art such as by transformation. The host cell into which the coding gene or the vector has been introduced may be cultured under conditions suitable for expression of the gene or peptide. The host cell may be either prokaryotic or eukaryotic. Examples of the prokaryote can include *Escherichia coli* and *Bacillus subtilis*, and examples of the eukaryote can include yeasts such as *Saccharomyces cerevisiae* and *Pichia pastoris*, insect cells such as SF9 and High5, and animal cells such as HeLa cells, CHO cells, COS cells and NSO. By using eukaryotic cells or the like as host cells, the expressed peptide of the present invention can be subjected to desired post-translational modifications. Examples of post-translational modifications can include the addition of functional groups such as gly-cochains, the addition of peptides or proteins, and the conversion of chemical properties of amino acids. It is also possible to apply desired modifications to the peptides of the present invention artificially. Such modified peptides are also encompassed within the scope of the peptide or conjugate of the present invention.

The present invention also provides a method for producing a peptide or conjugate. The method includes a step 1 of culturing the coding gene-containing cell or producing cell and/or a step 2 of recovering the peptide or conjugate from the culture obtained in step 1. In step 2, procedures known to those skilled in the art such as fractionation, chromatography and purification can be applied. For example, purification by affinity chromatography using the antibody of the present invention described later can be applied.

The peptide or conjugate of the present invention can also be produced by other methods known to those skilled in the art, such as solid phase peptide synthesis methods including Merrifield synthesis or other methods, chemical synthesis methods such as organic synthetic chemical peptide synthesis methods using t-butoxycarbonyl (Boc) and 9-fluorenyl-methoxycarbonyl (Fmoc), and in vitro translation.

7. Pharmaceutical Composition

The present invention also provides a pharmaceutical composition comprising the peptide or conjugate.

The pharmaceutical composition of the present invention is useful for the treatment and/or prevention of various diseases which are elicited or exacerbated by a disease-related target molecule, and in which the inhibition or suppression of expression or function of the target molecule can result in suppression of elicitation or exacerbation, cure, retention or improvement of symptoms, avoidance of secondary diseases, or the like. The pharmaceutical composition preferably contains a peptide or conjugate in which the blood kinetics of the original peptide or conjugate having an activity against a disease-related target molecule have been improved.

The pharmaceutical composition of the present invention can contain a therapeutically and a prophylactically effective amount of the peptide or conjugate having an activity against a disease-related target molecule, and a pharmaceutically acceptable diluent, carrier, solubilizer, emulsifier, preservative and/or adjuvant.

The term "therapeutically and prophylactically effective amount" means an amount that exerts a therapeutic or prophylactic effect per particular disease, administration form and administration route, and has the same meaning as a "pharmacologically effective amount".

The pharmaceutical composition of the present invention can contain a substance for altering, maintaining or retaining pH, osmotic pressure, viscosity, transparency, color, isotonicity, sterility, or stability, solubility, sustained release, absorptivity, permeability, dosage form, strength, property, shape, or the like of the composition or peptide, conjugate or the like contained therein (hereinafter referred to as a "substance for formulation"). The substance for formulation is not particularly limited as long as it is pharmacologically acceptable. For example, non-toxicity or low toxicity is a property that the substance for formulation preferably has.

Examples of the substance for formulation can include, but are not limited to, amino acids such as glycine, alanine, glutamine, asparagine, histidine, arginine or lysine; antibacterial agents; antioxidants such as ascorbic acid, sodium sulfate or sodium bisulfite; buffers such as phosphoric acid, citric acid, boric acid buffer, sodium hydrogen carbonate, and Tris-HCl solution; fillers such as mannitol and glycine; chelating agents such as ethylenediaminetetraacetic acid (EDTA); complexing agents such as caffeine, polyvinylpyr-rolidine, β-cyclodextrin and hydroxypropyl-β-cyclodextrin; bulking agents such as glucose, mannose or dextrin; mono-saccharides, disaccharides and other carbohydrates such as glucose, mannose and dextrin; coloring agents; flavoring agents; diluents; emulsifying agents; and hydrophilic polymers such as polyvinylpyrrolidine; low molecular weight polypeptides; salt-forming counterions; preservatives such as benzalkonium chloride, benzoic acid, salicylic acid, thimerosal, phenethyl alcohol, methylparaben, propylpara-ben, chlorexidine, sorbic acid or hydrogen peroxide; solvents such as glycerin, propylene glycol or polyethylene glycol (PEG), sugar alcohols such as mannitol or sorbitol, suspending agents, sorbitan esters; polysorbates such as polysorbate 20 and polysorbate 80; surfactants such as triton, tromethamine, lecithin or cholesterol; stabilization enhancers such as sucrose and sorbitol; elastic enhancers such as sodium chloride, potassium chloride, mannitol and sorbitol; transport agents; diluents; excipients; and/or pharmaceutical adjuvants. The pharmaceutical composition containing the peptide or conjugate in a liposome and the pharmaceutical composition containing a modified product of the peptide or conjugate linked to a liposome are also included in the present invention.

The excipient and carrier are usually liquid or solid, and are not particularly limited as long as they are substances used in formulations for oral or parenteral administration such as water used for injection, physiological saline, artificial cerebrospinal fluid, and like others. Examples of physiological saline can include neutral saline and saline containing serum albumin.

Examples of the buffer can include a Tris buffer prepared so that the final pH of the pharmaceutical composition is to be 7.0 to 8.5, an acetate buffer prepared in the same way to be 4.0 to 5.5, a citrate buffer prepared in the same way to be 5.0 to 8.0, and a histidine buffer prepared in the same way to be 5.0 to 8.0.

The pharmaceutical composition of the present invention is a solid, a liquid, a suspension, or the like. Other examples of the pharmaceutical composition of the present invention can include a lyophilized formulation. Excipients such as sucrose can be used to form a lyophilized formulation.

The administration route of the pharmaceutical composition of the present invention may be any of eye dropping, enteral administration, topical administration, and parenteral administration, and examples can include eye dropping on the conjunctiva, intravitreal administration, intravenous administration, intraarterial administration, intramuscular administration, intradermal administration, subcutaneous administration, intraperitoneal administration, transdermal administration, intraosseous administration, and intraarticular administration.

The composition of such a pharmaceutical composition can be determined according to the administration method, the activity against or the binding affinity to the target, and the like. As the activity against the target is stronger, the effect may be exerted at a lower dosage.

The dose of the peptide or conjugate of the present invention is not limited as long as it is a pharmacologically effective amount, and it can be appropriately determined according to factors such as species of the individual, type of the disease, symptoms, sex, age, chronic disease, inhibitory activity against the target of the peptide, binding affinity, and like other factors. However, usually, 0.01 to 1000 mg/kg, preferably 0.1 to 100 mg/kg of the peptide or conjugate may be administered once or twice or three or more times a day for 1 to 180 days.

Examples of the form of the pharmaceutical composition can include injections (including lyophilized formulations and drops), suppositories, nasal absorption formulations, transdermal absorption formulations, sublingual formulations, capsules, tablets, ointments, granules, aerosols, pills, powders, suspensions, emulsions, eye drops, and bioimplant formulations.

The peptide, conjugate, or pharmaceutical composition containing the same can be administered simultaneously or separately with an additional pharmaceutical. For example, a pharmaceutical composition containing the peptide or conjugate as an active ingredient is administered after the additional pharmaceutical is administered, or the pharmaceutical composition is administered before the additional pharmaceutical is administered, or the pharmaceutical composition and the additional pharmaceutical may be administered simultaneously. When administered simultaneously, the peptide or conjugate and the additional pharmaceutical may be formulated in either a single formulation or separate formulations (multiple formulations).

One, or two, or three or more additional pharmaceuticals may be administered or formulated. These are collectively referred to as the "combination use with an additional pharmaceutical" or "combination with an additional pharmaceutical". The pharmaceutical composition of the present invention containing an additional pharmaceutical in addition to the peptide or conjugate of the present invention, or used in combination with other therapy is also included in the present invention as an embodiment of the "combination use with an additional pharmaceutical" or "combination with an additional pharmaceutical".

EXAMPLES

In the following examples, some embodiments of the present invention are further described in detail, but the present invention is not limited thereto.

It should be noted that, in the Examples below, each procedure related to genetic manipulation was performed in accordance with the methods described in "Molecular Cloning" (Sambrook, J., Fritsch, E. F. and Maniatis, T., published in 1982 or 1989 from Cold Spring Harbor Laboratory Press) and the methods described in other experimental textbooks used by those skilled in the art, or in accordance with the instructions of commercial products when using commercial reagents or kits.

Example 1. Preparation of KLK5 Inhibitory SPINK2-Fc Fusion (1-1) Construction of Expression Vector of KLK5 Inhibitory SPINK2-Fc Fusion Using the sequences (sequence listing) of each inhibitory SPINK2 as templates, inhibitor fragments (D0-D5, E1) were amplified by a PCR method ((94° C., 15 seconds; 60° C., 30 seconds; 68° C., 20 seconds)×30 cycles) with the following primers and KOD-plus-(TOYOBO CO., LTD.).

```
Primer for inhibitor fragment (D0)
Primer 1:
                                    (SEQ ID NO: 15: FIG. 21)
5'-AGATGGGTGTTGTCTGGCCCTCAGTTCGGCCTGTTC-3'

Primer 2:
                                    (SEQ ID NO: 16: FIG. 22)
5'-GCAGGGGCCATTCCGGAT-3'

Primer for inhibitor fragment (D1)
Primer 3:
                                    (SEQ ID NO: 17: FIG. 23)
5'-AGATGGGTGTTGTCTGACGGCCCTCAGTTCGGCCTGTTC-3'

Primer 2
                                    (SEQ ID NO: 16, FIG. 22)

Primer for inhibitor fragment (E1)
Primer 4:
                                    (SEQ ID NO: 18: FIG. 24)
5'-AGATGGGTGTTGTCTGAAGGCCCTCAGTTCGGCCTGTTC-3'

Primer 2
                                    (SEQ ID NO: 16, FIG. 22)

Primer for inhibitor fragment (D2)
Primer 5:
                                    (SEQ ID NO: 19: FIG. 25)
5'-AGATGGGTGTTGTCTGACGACGGCCCTCAGTTCGGCCTGTTC-3'
```

27

28

-continued

```
Primer 2
                                (SEQ ID NO: 16, FIG. 22)

Primer for inhibitor fragment (D3)
Primer 6:
                                (SEQ ID NO: 20: FIG. 26)
5'-AGATGGGTGTTGTCTGATGACGACGGCCCTCAGTTCGGCCTGTTC-3'

Primer 2
                                (SEQ ID NO: 16, FIG. 22)

Primer for inhibitor fragment (D4)
Primer 7:
                                (SEQ ID NO: 21: FIG. 27)
5'-AGATGGGTGTTGTCTGATGATGACGACGGCCCTCAGTTCGGCCTGTTC-3'

Primer 2
                                (SEQ ID NO: 16, FIG. 22)

Primer for inhibitor fragment (D5)
Primer 8:
                                (SEQ ID NO: 22: FIG. 28)
5'-AGATGGGTGTTGTCTGACGATGATGACGACGGCCCTCAGTTCGGCCTGTTC-3'

Primer 2
                                (SEQ ID NO: 16, FIG. 22)
```

Fragment A was amplified by a PCR method ((94° C., 15 seconds; 60° C., 30 seconds; 68° C., 10 seconds)×30 cycles) with the following primers and KOD-plus-(TOYOBO CO., LTD.).

```
Primer 9:
                                (SEQ ID NO: 23: FIG. 29)
5'-AAAATCTAGAGCCGCCACCATGAAGCACCTGTGGTTCTTTCTGCTG
CT-3'

Primer 10:
                                (SEQ ID NO: 24: FIG. 30)
5'-AGACAACACCCATCTAGGAGCGGCCACCAGCAGCAGAAAGAAC
C-3'
```

Using the Fc region of human IgG1 (SEQ ID NO: 34, FIG. 40) as a template, fragment B containing the Fc region of human IgG1 was amplified by a PCR method ((94° C., 15 seconds; 60° C., 30 seconds; 68° C., 30 seconds)×30 cycles) with the following primers and KOD-plus-(TOYOBO CO., LTD.).

```
Primer 11:
                                (SEQ ID NO: 25: FIG. 31)
5'-ATCCGGAATGGCCCCTGCGAACCCAAGAGCTGCGAC-3'

Primer 12:
                                (SEQ ID NO: 26: FIG. 32)
5'-AAAAGTTTAAACTCATTTGCCGGGGCTCAG-3'
```

The desired DNA fragments were amplified by an overlap PCR method using the above amplified inhibitor fragments and fragment A, fragment B, primer 9 (SEQ ID NO: 23, FIG. 29), primer 12 (SEQ ID NO: 26, FIG. 32) and KOD-plus-(TOYOBO CO., LTD.).

Figure 1:
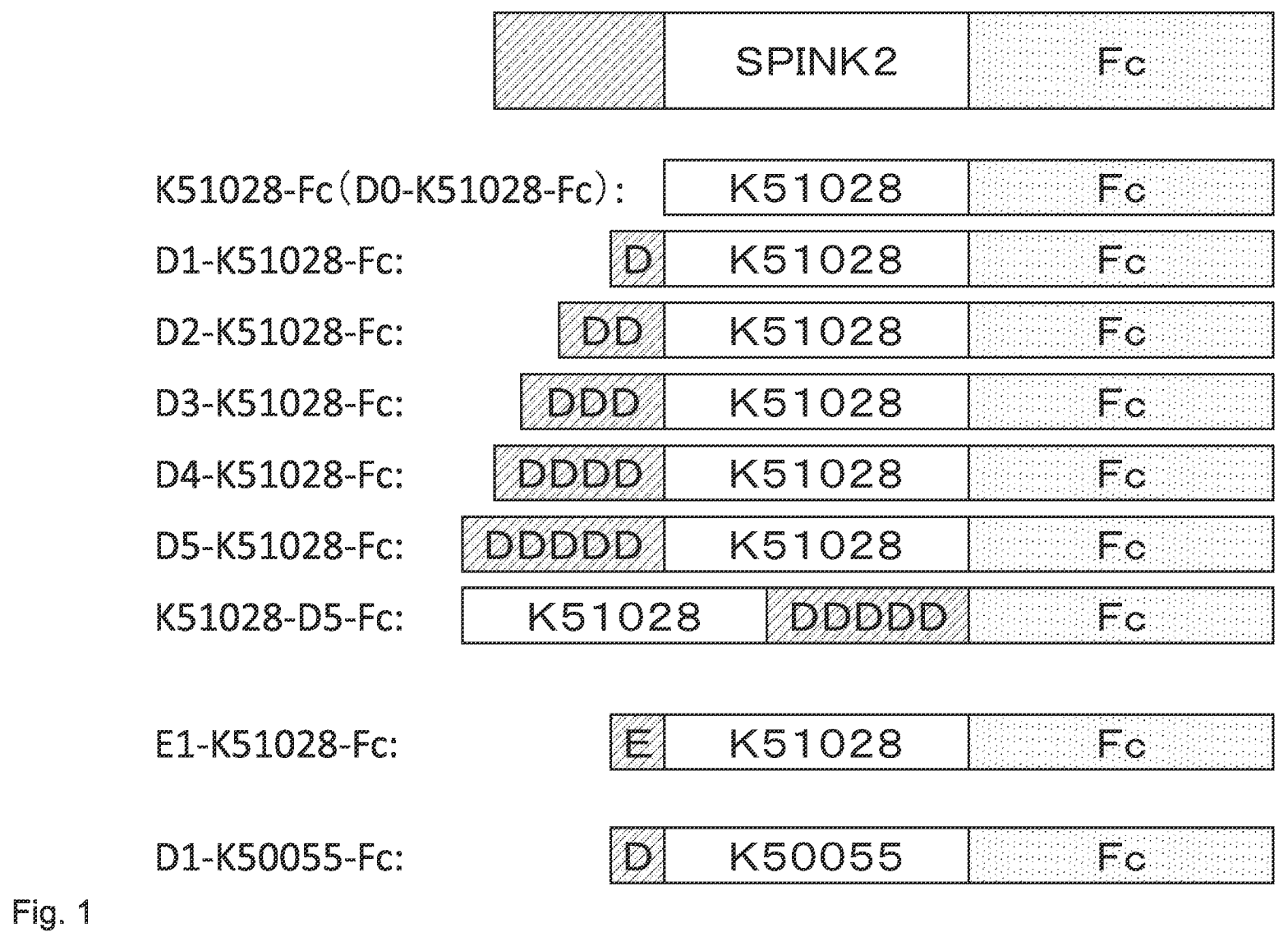

The amplified fragments were subjected to agarose gel electrophoresis, then the desired DNA fragments were excised and the DNA was prepared with a QIAquick Gel Extraction Kit (QIAGEN). The prepared DNA fragments and a mammalian cell expression vector pCMA were treated with restriction enzymes XbaI (NEB) and PmeI (NEB) at 37° C. for 1 hour or more. After agarose gel electrophoresis, the desired DNA fragments were excised, and purified with a QIAquick PCR Purification Kit (QIAGEN). The purified fragments each were allowed to react at room temperature for 10 minutes using LigaFast Rapid DNA Ligation System (Promega Corporation) to carry out a ligation reaction. The ligation solution was added to E. coli JM109 (TOYOBO CO., LTD.) and the cells were allowed to stand on ice for 30 minutes, then subjected to a heat treatment of 42° C. for 45 seconds, then allowed to stand on ice for 5 minutes, then seeded on a 2YT plate containing 0.1 mg/mL ampicillin, and then subjected to a static culture at 37° C. overnight to transform E. coli. The next day, the transformed E. coli was inoculated into a Terrific broth medium (Invitrogen) containing 0.1 mg/mL ampicillin, and cultured at 37° C. overnight. The plasmid DNA was then recovered with a QIAprep 96 Turbo Miniprep Kit (Qiagen) (hereinafter referred to as "miniprep treatment"), and sequence analysis was performed to construct a mammalian cell expression vector pCMA_KLK5 inhibitory SPINK2-Fc fusion (ID of each clone is described in FIG. 1).

Furthermore, using KLK5 inhibitory SPINK2 clone pCMA_K51028-Fc as a template, a fragment inserted with five Asp between KLK5 inhibitory SPINK2 and the Fc region of human IgG1 was amplified, and self-cyclized with the following primers and a KOD-Plus-Mutagenesis Kit (TOYOBO CO., LTD.). Transformation and sequence analysis of E. coli were performed according to the methods described above to construct a mammalian cell expression vector pCMA_K51028-D5-Fc.

```
Primer 13:
                                (SEQ ID NO: 27: FIG. 33)
5'-GATGACGACGAACCCAAGAGCTGC-3'

Primer 14:
                                (SEQ ID NO: 28: FIG. 34)
5'-ATCGTCGCAGGGGCCATTCCG-3'
```

(1-2) Expression and Purification of KLK5 Inhibitory SPINK2-Fc Fusion

The expression vectors constructed in (1-1) were transfected into Expi293F cells (Thermo Fisher Scientific) using PEI MAX 40000 (Polysciences, Inc.), and after culturing for six days, the culture supernatant was recovered. The desired Fc fusion was recovered from the culture supernatant using MabSelect SuRe (GE Healthcare), and the buffer was exchanged with PBS using Amicon Ultra NMWL 10,000 (Merck Millipore) to prepare KLK5 inhibitory SPINK2-Fc fusions (FIG. 1).

Example 2. Evaluation of KLK5 Inhibitory Activity of KLK5 Inhibitory SPINK2-Fc Fusions (2-1) Preparation of KLK5

Fragment C was amplified by a PCR method ((94° C., 15 seconds; 60° C., 30 seconds; 68° C., 10 seconds)×30 cycles) with the following primers and KOD-plus-(TOYOBO CO., LTD.).

```
Primer 15:
                           (SEQ ID NO: 29: FIG. 35)
5'-GGCGATTATAAAGATGACGATGATAAACACCATCACCACCATC-3'

Primer 16:
                           (SEQ ID NO: 30: FIG. 36)
5'-GTTTAAACTCAATGATGGTGGTGATGGTGTTTATCATCGTCAT-3'
```

Next, using nucleotide sequences encoding human pro-KLK5 (Uniprot: Q9Y337) each as a template, fragments were amplified by a PCR method ((94° C., 15 seconds; 60° C., 30 seconds; 68° C., 60 seconds)×30 cycles) with the following primers and KOD-plus-(TOYOBO CO., LTD.).

```
Primer 17:
                           (SEQ ID NO: 31: FIG. 37)
5'-AAAATCTAGAGCCGCCACCATGGCCACAGCTAGACCCCCT-3'

Primer 18:
                           (SEQ ID NO: 32: FIG. 38)
5'-CGTCATCTTTATAATCGCCGCTGTTGGCCTGGATGGTTTCCTG-3'
```

The desired DNA fragments were amplified by an overlap PCR method with the above-amplified fragments and fragment C, the following primers, and KOD-plus-(TOYOBO CO., LTD.).

```
    Primer 17
                           (SEQ ID NO: 31, FIG. 37)

Primer 19:
                           (SEQ ID NO: 33: FIG. 39)
    5'-AAAAGTTTAAACTCAATGATGGTGGTGATGGTGT-3'
```

In addition, cloning with restriction enzymes XbaI (NEB) and PmeI (NEB) was performed to construct mammalian cell expression vectors pCMA pro-KLK5 in which a Flag tag and a His tag were added to the C-terminus of each gene.

(2-2) Expression and Purification of KLK5

The expression vectors constructed in (2-1) were transfected into Expi293F cells (Thermo Fisher Scientific) using PEI MAX 40000 (Polysciences, Inc.), and after culturing for three days, the culture supernatant was recovered. The desired His tag fusion protein was recovered from the culture supernatant using HisTrap excel (GE Healthcare), and the buffer was exchanged with PBS using Amicon Ultra NMWL 10,000 (Merck Millipore) to purify KLK5.

(2-3) Evaluation of KLK5 Inhibitory Activity of KLK5 Inhibitory SPINK2-Fc Fusions The substrate peptide was dissolved in DMSO to 10 mM, then diluted with an assay buffer (50 mM Tris-HCl, 150 mM NaCl, pH 8.0) and used at the final concentration of 100 μM. The KLK5 and KLK5 inhibitory SPINK2-Fc fusion with the assay buffer were mixed at 25 μL each, and reacted at 37° C. for 20 minutes. Then, 50 μL of the substrate diluted with the assay buffer was added, and fluorescence signal was measured with Enspire (PerkinElmer). The combinations of each enzyme and substrate were used as follows. Each inhibitory peptide Fc fusion was at a final concentration of 0.022 to 1,300 nM. A Proteosave® SS96F black plate (Sumitomo Bakelite Co., Ltd.) was used for the reaction and measurement.

Human KLK5 inhibitory activity evaluation; KLK5 at final concentration of 20 nM, substrate peptide Boc-Val-Pro-Arg-AMC (R&D Systems; ES011) at final concentration of 100 μM, fluorescent signal excitation 380 nm/emission 460 nm.

The substrate peptide degradation rate of each SPINK2-Fc fusion at each concentration was calculated, and regressed to a 4-parameter logistic sigmoid curve using GraphPad Prism (version 5.0; GraphPad Software Inc.) by setting the degradation rate at the inhibitor concentration of 0 nM as 100%. All SPINK2-Fc fusions inhibited KLK5 enzyme activity at low concentrations, and no difference in KLK5 inhibitory activity was observed between the designs (FIG. 2).

Example 3. Mouse PK Test of SPINK2-Fc Fusions (3-1) Animal Test

The KLK5 inhibitory SPINK2-Fc fusion produced in Example 1 was prepared with PBS to 0.75 mg/mL and used as an administration solution. Male C57BL/6J mice (CHARLES RIVER LABORATORIES JAPAN, INC.) aged 4.5 weeks to 8 weeks which were domesticated for 4 to 8 days after arrival were subjected to intravenous administration at a dose of 5 mg/kg. The intravenous administration was performed by intravenous administration either to the jugular vein or to the tail vein. The intravenous administration to the jugular vein was performed as follows. Mice were subjected to inhalation anesthesia with isoflurane, and the neck hair was shaved with hair clippers, then the skin was incised to expose the jugular vein. The needle tip of a syringe with a needle for subcutaneous insulin administration (29G) filled with the administration solution was used to puncture through the muscle below the exposed jugular vein, and after visually confirming that the needle tip had entered the jugular vein, the plunger was pressed to administer the drug. The intravenous administration to the tail vein was performed as follows. Mice were subjected to inhalation anesthesia with isoflurane, the tail was warmed with a cloth wet with warm water or wiped with alcoholic cotton to vasodilate the vein, then the needle tip of the syringe with a needle for subcutaneous insulin administration filled with the administration solution was inserted into the tail vein. The plunger was slightly pulled to confirm venous blood reflux into the syringe, then the plunger was pressed to perform the administration. A syringe with a needle for subcutaneous insulin administration was aspirated with sodium heparin injection solution once, and then ejected to use the syringe as a blood collection syringe. At 5 minutes, 1 hour, 3 hours, 6 hours, and 24 hours after administration, about 0.05 mL of blood was collected from the non-administered side jugular vein using the blood collection syringe under inhalation anesthesia with isoflurane. The blood was transferred to a 1.5 mL volumetric polypropylene tube and centrifuged at centrifugal force of 21,600×g for 3 minutes under cooling to obtain a supernatant (plasma).

(3-2) Measurement

Concentration measurements of KLK5 inhibitory SPINK2-Fc fusion in plasma were performed using a fully automated immunoassay platform Gyrolab xP Workstation (GYROS PROTEIN Technologies). The KLK5 inhibitory SPINK2-Fc fusion was diluted with 1% blank mouse plasma-containing Rexxip AN (GYROS PROTEIN Technologies) to 8 serial dilutions at a 2-fold common ratio from 2,000 ng/mL to prepare calibration curve samples. The plasma obtained in the experiment was diluted 100-fold with Rexxip AN to prepare a measurement sample. A biotin-labeled anti-SPINK2 antibody (Atlas Antibodies) was prepared with 0.1% Tween 20®-containing PBS to 350 nM and used as a capture antibody. In-house anti-SPINK2 antibody 6D8 labeled with DyLight650 was prepared with a Rexxip F buffer to 20 nM and used as a detection antibody. The calibration curve sample, the measurement sample, the capture antibody, the detection antibody, and a wash buffer (0.1% Tween 20®-containing PBS) were placed into 96-well PCR plates and set in the Gyrolab xP workstation with Gyrolab Bioaffy 200 to measure with 3-StepC-A-D (wizard method). The calibration curve was regressed with a 4-parameter logistic model (weighting; response) using Gyrolab Evaluator Software. A non-compartmental analysis was performed using Phoenix WinNonlin 6.3 (Certara L.P.) to calculate the area under the plasma concentration-time curve from 0 to 24 hours after administration ($AUC_{0\text{-}24\,h}$) (Calculation Method; Linear Up-Log Down).

(3-3) PK of SPINK2-Fc Fusion

Figure 3:
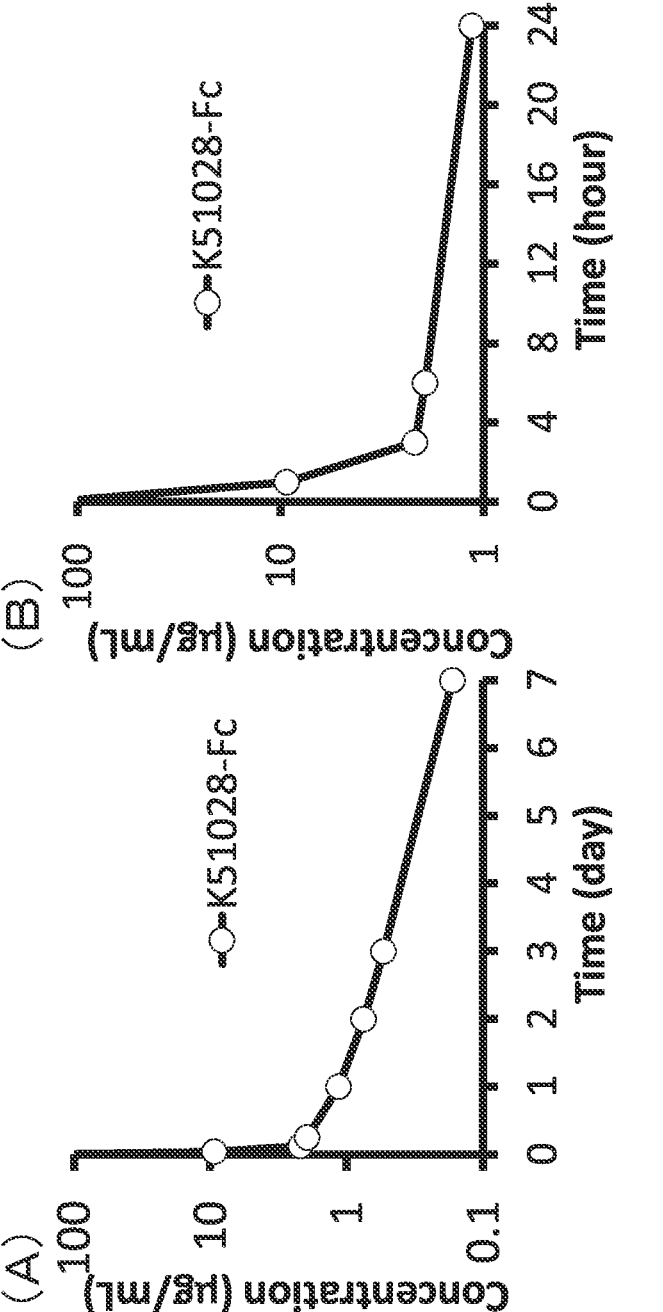
FIG. 3 is a graph of K51028-Fc concentration measurements in plasma over time following intravenous administration of 5 mg/kg K51028-Fc to C57BL/6J mice. K51028-Fc concentration in plasma was measured with a biotin-labeled anti-SPINK2 antibody (Atlas Antibodies), a DyLight650-labeled anti-SPINK2 antibody 6D8 (DAIICHI SANKYO COMPANY, LIMITED) and a Gyrolab xP Workstation (GYROS PROTEIN Technologies) until (A) 1 week after administration or (B) 24 hours after administration.
Figure 4:
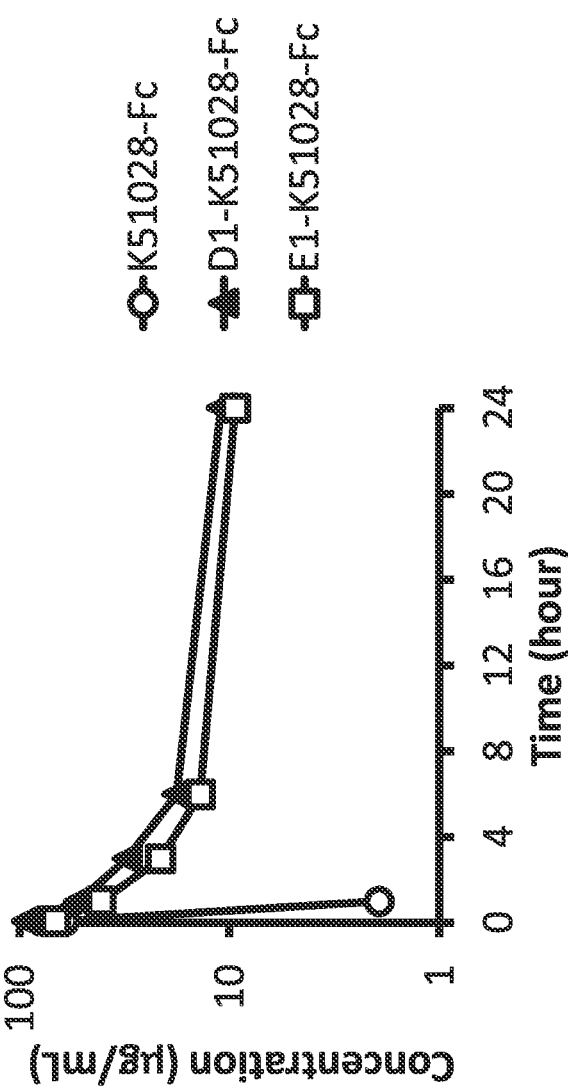
FIG. 4 shows that addition of Asp or Glu to K51028-Fc resulted in an improvement in blood kinetics of SPINK2-Fc fusion. 5 mg/kg of test substance was intravenously administered to C57BL/6J mice, and concentration of the test substance in plasma was measured until 24 hours after administration. The test substance was K51028-Fc, D1-K51028-Fc, or E1-K51028-Fc. In measurement of the test substance concentration, a biotin-labeled anti-SPINK2 antibody, a DyLight650-labeled anti-SPINK2 antibody 6D8, and a Gyrolab xP Workstation were used.
Figure 5:
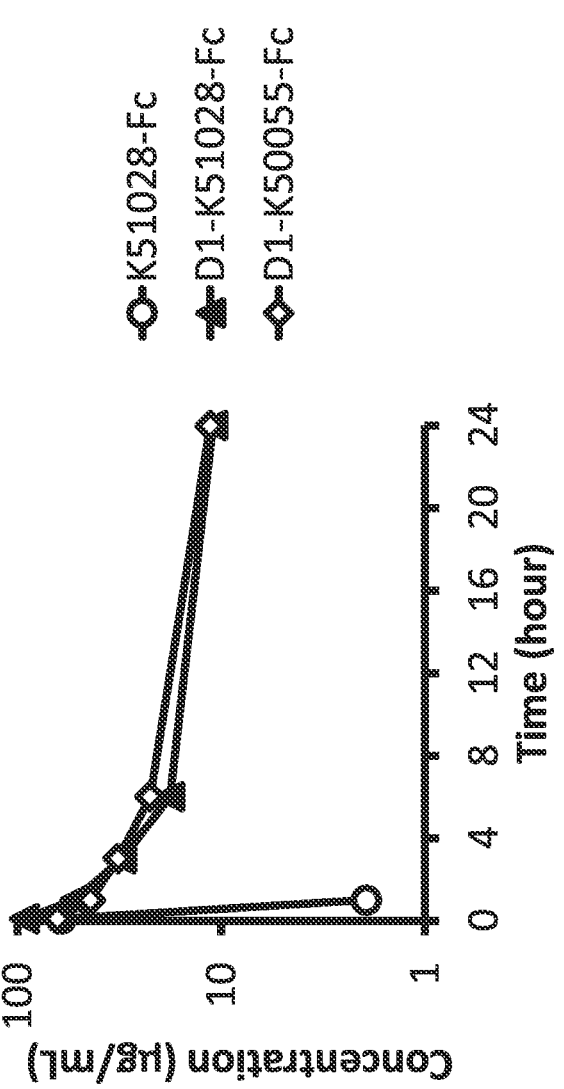
FIG. 5 shows that addition of Asp to K50055-Fc improved blood kinetics of the SPINK2-Fc fusion, as with K51028-Fc.
Figure 6:
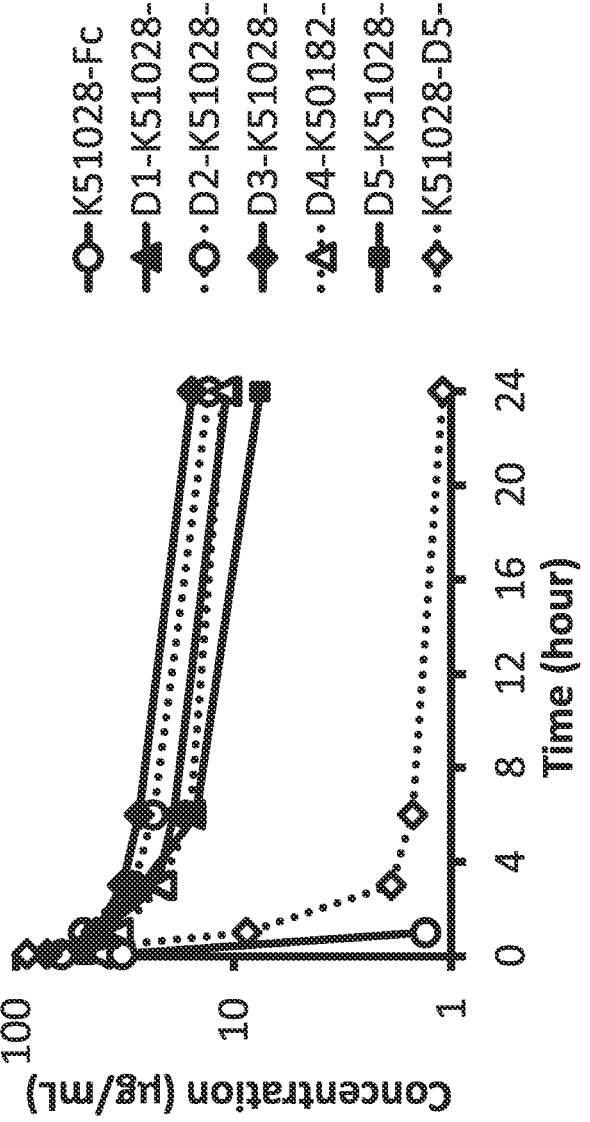
FIG. 6 shows optimization of Asp addition number effective for improvement in the blood kinetics of the SPINK2-Fc fusion based on K51028-Fc. The Asp addition number of 1 to 5 all exhibited improved effects, and the Asp addition number of 3 exhibited the highest effect.

KLK5 inhibitory SPINK2-Fc fusion K51028-Fc exhibited blood kinetics shown in FIG. 3(A) at 7 days after administration to a mouse, and a significant decrease in blood concentration by 3 hours after administration was observed (FIG. 3(B)). Addition of 1 residue of Asp or Glu to the N-terminus of K51028-Fc suppressed the significant decrease in blood concentration of the administered specimen observed up to 3 hours after administration (FIG. 4). This effect was sequence-independent, and a similar effect was observed in both sequences of D1-K51028-Fc and D1-K50055-Fc (FIG. 5). Furthermore, any design of additions of 1 to 5 residues of Asp to the N-terminus of K51028-Fc suppressed the significant decrease in blood concentration of the administered specimen observed up to 3 hours after administration (FIG. 6). Furthermore, due to the improvement of the significant decrease in blood concentration up to 3 hours after administration, a significant increase of blood exposure up to 24 hours after administration was also observed (Table 1). The enhancement effect of the blood exposure amount was the highest in the Asp addition number of 3 (D3), followed by the Asp addition number of 2 (D2) and the Asp addition number of 1 (D1) in this order. However, K51028-D5-Fc, in which five Asp were placed between SPINK2 and the Fc region, did not lead to either suppression of the significant decrease in blood concentration of the administered specimen observed up to 3 hours after administration nor increase in blood exposure up to 24 hours after administration. From the above results, the insertion of one to five Asp or Glu into the N-terminus portion of a SPINK2-Fc suppressed the decrease in blood concentration observed at an early stage after administration and achieved a significant increase in blood exposure.

Coordinating negatively charged amino acids in the N-terminus portion of the Fc fusion has no significant effect on pI of the Fc fusion and permits a local negative charge, thus there is no effect on activity, physical properties, or the like. This design successfully achieved suppression of blood concentration decrease of a SPINK2 variant peptide Fc fusion at an early stage after administration and retention of the Fc fusion after administration at high concentrations, without significantly affecting the activity and physical properties of the SPINK2 variant peptide.

TABLE 1

| Area under the plasma concentration-time curve from 0 to 24 hours after administration ($AUC_{0\text{-}24\,h}$) | |
| --- | --- |
| ID | $AUC_{0\text{-}24\,h}$ ($\mu g \cdot h/mL$) |
| K51028-Fc | 13 |
| D1-K51028-Fc | 440 |
| D2-K51028-Fc | 530 |
| D3-K51028-Fc | 598 |
| D4-K51028-Fc | 390 |
| D5-K51028-Fc | 370 |
| K51028-D5-Fc | 77 |

Example 4. Preparation and Evaluation of KLK5 Inhibitory SPINK2-Fc (IgG2, IgG4P) Fusions (4-1) Construction of Expression Vector of KLK5 Inhibitory SPINK2-Fc (IgG2, IgG4P) Fusions Using the mammalian cell expression vectors pCMA_K51028-Fc, pCMA_D1-K51028-Fc or pCMA_D3-K51028-Fc constructed in (1-1) as a template, inhibitor fragments (D0-K51028, D1-K51028, D3-K51028) were amplified by a PCR method ((94° C., 15 seconds; 60° C., 30 seconds; 68° C., 75 seconds)×30 cycles) with the following primers and KOD-plus-(TOYOBO CO., LTD.).

```
Primers for inhibitor fragments D0-K51028,
D1-K51028, D3-K51028)
Primer 20:
                          (SEQ ID NO: 35: FIG. 41)
5'-TGAGTTTAAACTTTTAAACGGGGG-3'

Primer 21:
                          (SEQ ID NO: 36: FIG. 42)
5'-GCAGGGGCCATTCCGGATGATCTT-3'
```

Using the Fc region of human IgG2 (SEQ ID NO: 37, FIG. 43) as a template, fragment D containing the Fc region of human IgG2 was amplified by a PCR method ((94° C., 15 seconds; 60° C., 30 seconds; 68° C., 30 seconds)×30 cycles) with the following primers and KOD-plus-(TOYOBO CO., LTD.).

```
Primer 22:
                          (SEQ ID NO: 38: FIG. 44)
5'-CGGAATGGCCCCTGCGAGCGTAAGTGTTGTGTGGAGTGT-3'

Primer 23:
                          (SEQ ID NO: 39: FIG. 45)
5'-CCCCGTTTAAACTCACTTTCCAGGGCTCAGGGAAAGGCT-3'
```

Using the Fc region of human IgG4P (SEQ ID NO: 40, FIG. 46) as a template, fragment E containing the Fc region of human IgG4P was amplified by a PCR method ((94° C., 15 seconds; 60° C., 30 seconds; 68° C., 30 seconds)×30 cycles) with the following primers and KOD-plus-(TOYOBO CO., LTD.).

```
Primer 24:
                          (SEQ ID NO: 41: FIG. 47)
5'-CGGAATGGCCCCTGCGAATCTAAGTACGGCCCTCCCTGC-3'

Primer 25:
                          (SEQ ID NO: 42: FIG. 48)
5'-CCCCGTTTAAACTCATTTGCCCAGGCTCAGAGACAGGGA-3'
```

The amplified fragments were subjected to agarose gel electrophoresis, then the desired DNA fragment was excised and the DNA was prepared by a QIAquick Gel Extraction Kit (QIAGEN). To each inhibitor fragment prepared, fragment D or fragment E was added. The mixture was reacted at 50° C. for 15 minutes with an In-Fusion HD Cloning Kit (TAKARA BIO) to ligate the fragments. The ligated fragment was added to *E. coli* JM109 (TOYOBO CO., LTD.) and the cells were allowed to stand on ice for 30 minutes, then subjected to a heat treatment of 42° C. for 45 seconds, and allowed to stand on ice for 5 minutes, then seeded on a 2YT plate containing 0.1 mg/mL ampicillin, and then subjected to static culture at 37° C. overnight to transform *E. coli*. The next day, the transformed *E. coli* was inoculated into a Terrific Broth medium (Invitrogen) containing 0.1 mg/mL ampicillin, and cultured at 37° C. overnight. The plasmid DNA was then recovered with a QIAprep 96 Turbo Miniprep Kit (Qiagen) (hereinafter referred to as "miniprep treatment"), and sequence analysis was performed to construct a mammalian cell expression vector pCMA_KLK5 inhibitory SPINK2-Fc (IgG2, IgG4P) fusion.

(4-2) Expression and purification of KLK5 inhibitory SPINK2-Fc (IgG2, IgG4P) fusions The expression vectors constructed in (4-1) were transfected into Expi293F cells (Thermo Fisher Scientific) using PEI MAX 40000 (Polysciences, Inc.), and after culture for six days, the culture supernatant was recovered. The desired Fc fusion was recovered from the culture supernatant using MabSelect SuRe (GE healthcare), and the buffer was exchanged with PBS using Amicon Ultra NMWL 10,000 (Merck Millipore) to prepare KLK5 inhibitory SPINK2-Fc (IgG2, IgG4P) fusions.

(4-3) Evaluation of KLK5 Inhibitory Activity of KLK5 Inhibitory SPINK2-Fc (IgG2, IgG4P) Fusions The substrate peptide was dissolved in DMSO to 10 mM, then diluted with an assay buffer (50 mM Tris-HCl, 150 mM NaCl, pH 8.0) and used at the final concentration of 100 μM. The KLK5 and KLK5 inhibitory SPINK2-Fc (IgG2, IgG4P) fusion diluted with the assay buffer were mixed at 25 μL each, and reacted at 37° C. for 20 minutes. Then, 50 μL of the substrate diluted with the assay buffer was added, and fluorescence signal was measured with Enspire (PerkinElmer). The combinations of each enzyme and substrate were used as follows. Each KLK5 inhibitory SPINK2-Fc (IgG2, IgG4P) fusion was at a final concentration of 1.6 to 100 nM. A Proteosave® SS96F black plate (Sumitomo Bakelite Co., Ltd.) was used for the reaction and measurement.

Human KLK5 inhibitory activity evaluation; KLK5 at final concentration of 20 nM, substrate peptide Boc-Val-Pro-Arg-AMC (R&D Systems; ES011) at final concentration of 100 μM, fluorescent signal excitation 380 nm/emission 460 nm.

Figure 55:
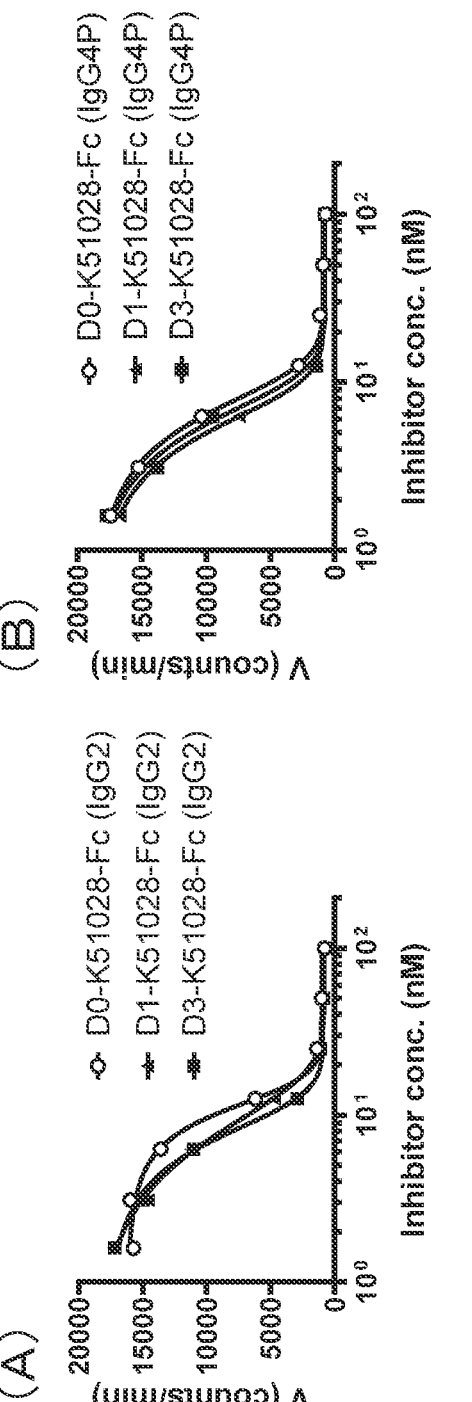
FIG. 55 shows KLK5 inhibitory activities (50% inhibitory concentration: IC50) of KLK5 inhibitory peptide Fc (IgG2, IgG4P) fusions using the degradation rate of a peptide substrate as an index. For evaluating the KLK5 inhibitory activities, KLK5 at a final concentration of 20 nM and a substrate peptide Boc-Val-Pro-Arg-AMC (R&D Systems; ES011) at a final concentration of 100 μM were used. There was no change in KLK5 inhibitory activity even when (A) one or three Asp were added based on D0-K51028-Fc (IgG2), or (B) one or three Asp were added based on D0-K51028-Fc (IgG4P).

The substrate peptide degradation rate of each KLK5-inhibitory SPINK2-Fc (IgG2, IgG4P) fusion at each concentration was calculated, and regressed to a 4-parameter logistic sigmoid curve using GraphPad Prism (version 5.0; GraphPad Software Inc.) by setting the degradation rate at the inhibitor concentration of 0 nM as 100%. All KLK5 inhibitory SPINK2-Fc (IgG2, IgG4P) fusions inhibited KLK5 enzyme activity at low concentrations, and no difference in KLK5 inhibitory activity was observed between the designs (FIG. 55).

Example 5. Mouse PK Test of KLK5 Inhibitory SPINK2-Fc (IgG2, IgG4P) Fusions (5-1) Animal Test The KLK5 inhibitory SPINK2-Fc (IgG2, IgG4P) fusion produced in (4-2) was prepared with PBS to 1 mg/mL and used as an administration solution. Male C57BL/6J mice (CHARLES RIVER LABORATORIES JAPAN, INC.) aged 6 weeks which were domesticated for 7 days after arrival were subjected to intrajugular administration at a dose of 5 mg/kg as follows. Mice were subjected to inhalation anesthesia with isoflurane, and the neck hair was shaved with hair clippers, then the skin was incised to expose the jugular vein. The needle tip of a syringe with a needle for subcutaneous insulin administration (29G) filled with the administration solution was used to puncture through the muscle below the exposed jugular vein, and after visually confirming that the needle tip had entered the jugular vein, the plunger was pressed to administer the drug. A syringe with a needle for subcutaneous insulin administration was aspirated with sodium heparin injection solution once, and then ejected to use the syringe as a blood collection syringe. At 5 minutes, 1 hour, 3 hours, 6 hours, and 24 hours after administration, about 0.03 mL of blood was collected from the non-administered side jugular vein using the blood collection syringe under inhalation anesthesia with isoflurane. The blood was transferred to a 1.5 mL volumetric polypropylene tube and centrifuged at centrifugal force of 21,600×g for 3 minutes under cooling to obtain a supernatant (plasma).

(5-2) Measurement

The concentration measurement of KLK5 inhibitory SPINK2-Fc (IgG2, IgG4P) fusion in plasma was performed using a fully automated immunoassay platform Gyrolab xP Workstation (GYROS PROTEIN Technologies). The KLK5 inhibitory SPINK2-Fc (IgG2, IgG4P) fusion was diluted with 1% blank mouse plasma-containing Rexxip AN (GYROS PROTEIN Technologies) to 7 serial dilutions at a 2.7-fold common ratio from 1,000 ng/mL to prepare calibration curve samples. The plasma obtained in the experiment was diluted 100-fold with Rexxip AN to prepare a measurement sample. A biotin-labeled anti-SPINK2 antibody (Atlas Antibodies) was prepared with 0.1% Tween 20®-containing PBS to 350 nM and used as a capture antibody. In-house anti-SPINK2 antibody 6D8 labeled with DyLight650 was prepared with a Rexxip F buffer to 20 nM and used as a detection antibody. The calibration curve sample, the measurement sample, the capture antibody, the detection antibody, and a wash buffer (0.1% Tween 20®-containing PBS) were placed into 96-well PCR plates and set in the Gyrolab xP workstation with Gyrolab Bioaffy 200 to measure with 3-StepC-A-D (wizard method). The calibration curve was regressed with a 4-parameter logistic model (weighting; response) using Gyrolab Evaluator Software. A non-compartmental analysis was performed using Phoenix WinNonlin 6.3 (Certara L.P.) to calculate the area under the plasma concentration-time curve from 0 to 24 hours after administration ($AUC_{0\text{-}24\,h}$) (Calculation Method; Linear Up-Log Down).

(5-3) PK of KLK5 Inhibitory SPINK2-Fc (IgG2, IgG4P) Fusions

Figure 56:
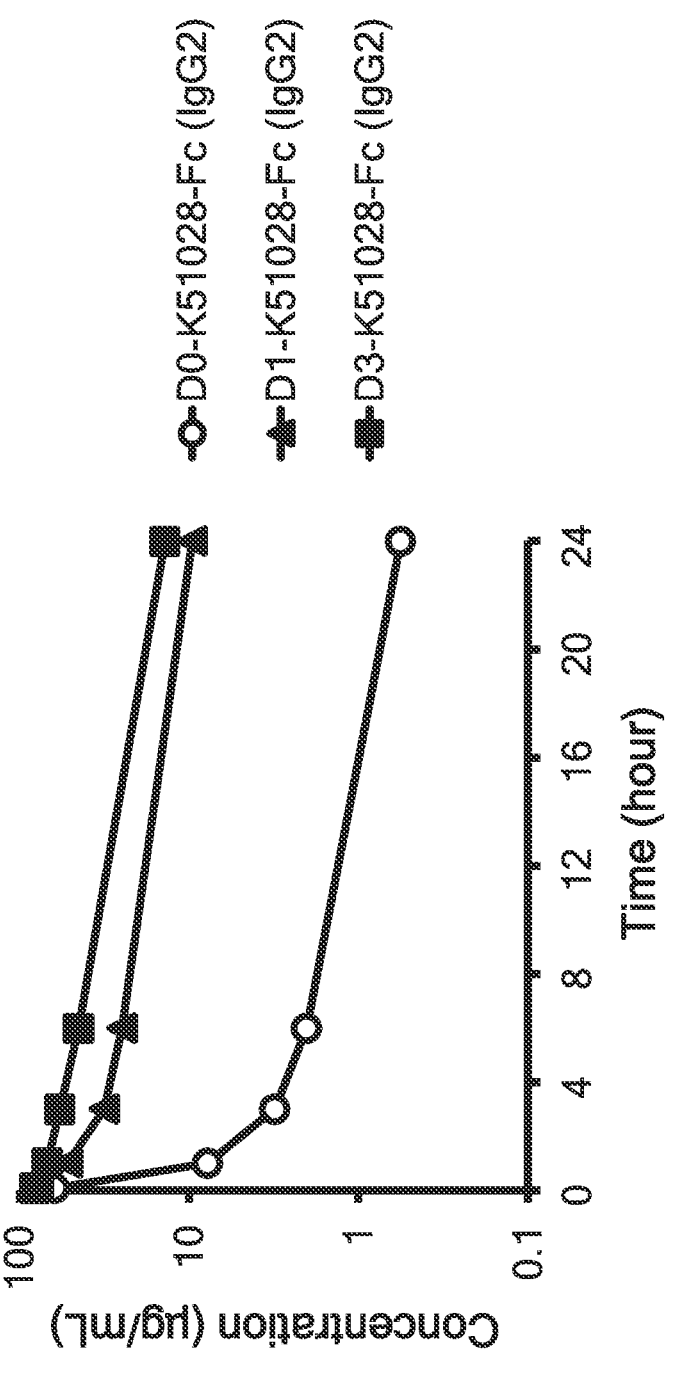
FIG. 56 shows that addition of one or more Asp to D0-K51028-Fc (IgG2) improved blood kinetics of SPINK2-Fc (IgG2) fusions. 5 mg/kg of D0-K51028-Fc (IgG2), D1-K51028-Fc (IgG2) or D3-K51028-Fc (IgG2) was intravenously administered to C57BL/6J mice, and the concentration of D0-K51028-Fc (IgG2), D1-K51028-Fc (IgG2) or D3-K51028-Fc (IgG2) in plasma was measured until 24 hours after administration. In measuring the concentration, a biotin-labeled anti-SPINK2 antibody, a DyLight650-labeled anti-SPINK2 antibody 6D8, and a Gyrolab xP Workstation were used.
Figure 57:
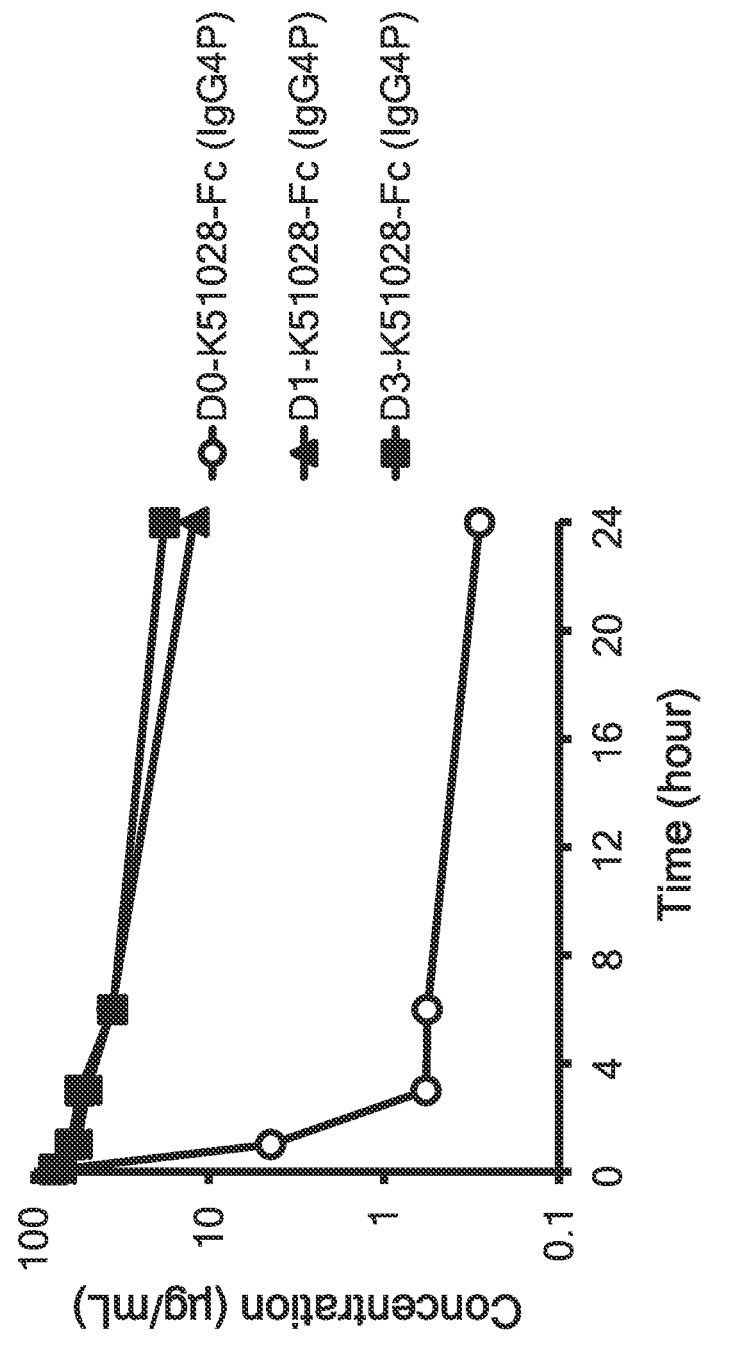
FIG. 57 shows that addition of Asp to D0-K51028-Fc (IgG4P) also improved blood kinetics of SPINK2-Fc (IgG4P) fusions, as with D0-K51028-Fc (IgG2).

KLK5 inhibitory SPINK2-Fc (IgG2) fusion D0-K51028-Fc (IgG2) exhibited blood kinetics shown in FIG. 56 at 24 hours after administration to a mouse, and a significant decrease in blood concentration by 3 hours after administration was observed. Addition of one Asp residue to the N-terminus of D0-K51028-Fc (IgG2) suppressed the significant decrease in blood concentration observed by 3 hours after administration (FIG. 56). Even when the addition number of Asp residues at the N-terminus was 3, the significant decrease in blood concentration observed by 3 hours after administration was suppressed (FIG. 56). This effect was also observed with IgG4P, independently of the Fc sequence (FIG. 57). Furthermore, due to the improvement of the significant decrease in blood concentration up to 3 hours after administration, a significant increase of blood exposure up to 24 hours after administration was also observed (Table 2). From the above results, the addition of one residue of Asp to the N-terminus portion of a SPINK2-Fc fusion improved the decrease in blood concentration observed at an early stage after administration of the SPINK2-Fc fusion and the low blood exposure associated therewith, and the same effect was exerted when fused with the Fc sequence of a different isotype of IgG.

Coordinating negatively charged amino acids on the N-terminus portion of the Fc fusion does not have a significant effect on pI of the Fc fusion, and permits a local negative charge, even when IgG2 or IgG4P with very weak effector function is employed as the Fc sequence of the Fc fusion; thus there is no effect on activity, physical properties, or the like. This design successfully achieved suppression of blood concentration decrease of SPINK2 variant peptide Fc fusions at an early stage after administration and retention of the Fc fusion after administration at high concentrations, without significantly affecting the activity and physical properties of the SPINK2 variant peptide.

TABLE 2

| Area under the plasma concentration-time curve from 0 to 24 hours after administration ($AUC_{0-24\ h}$) | |
| --- | --- |
| ID | $AUC_{0-24\ h}$ (µg · h/mL) |
| D0-K51028-Fc(IgG2) | 67.8 |
| D1-K51028-Fc(IgG2) | 519 |
| D3-K51028-Fc(IgG2) | 829 |
| D0-K51028-Fc(IgG4P) | 41.7 |
| D1-K51028-Fc(IgG4P) | 694 |
| D3-K51028-Fc(IgG4P) | 782 |

INDUSTRIAL APPLICABILITY

The blood kinetics improvement method provided by the present invention brings extension of blood half-life, increase of blood exposure amount, and the like of a peptide or a conjugate containing the peptide. Pharmaceuticals containing the peptide or the conjugate can be suitably used for treating or preventing various diseases.

FREE TEXT OF SEQUENCE LISTING

SEQ ID NO: 1—Amino acid sequence of human SPINK2 (FIG. 7)
SEQ ID NO: 2—General formula of SPINK2 variant peptide (FIG. 8)
SEQ ID NO: 3—Amino acid sequence of human KLK5 (FIG. 9)
SEQ ID NO: 4—Amino acid sequence of KLK5 inhibitory peptide K50055 (FIG. 10)
SEQ ID NO: 5—Amino acid sequence of KLK5 inhibitory peptide K51028 (FIG. 11)
SEQ ID NO: 6—Amino acid sequence of KLK5 inhibitory peptide Fc fusion D0-K51028-Fc (FIG. 12)
SEQ ID NO: 7—Amino acid sequence of KLK5 inhibitory peptide Fc fusion D1-K51028-Fc (FIG. 13)
SEQ ID NO: 8—Amino acid sequence of KLK5 inhibitory peptide Fc fusion D2-K51028-Fc (FIG. 14)
SEQ ID NO: 9—Amino acid sequence of KLK5 inhibitory peptide Fc fusion D3-K51028-Fc (FIG. 15)
SEQ ID NO: 10—Amino acid sequence of KLK5 inhibitory peptide Fc fusion D4-K51028-Fc (FIG. 16)

SEQ ID NO: 11—Amino acid sequence of KLK5 inhibitory peptide Fc fusion D5-K51028-Fc (FIG. 17)
SEQ ID NO: 12—Amino acid sequence of KLK5 inhibitory peptide Fc fusion K51028-D5-Fc (FIG. 18)
SEQ ID NO: 13—Amino acid sequence of KLK5 inhibitory peptide Fc fusion E1-K51028-Fc (FIG. 19)
SEQ ID NO: 14—Amino acid sequence of KLK5 inhibitory peptide Fc fusion D1-K50055-Fc (FIG. 20)
SEQ ID NO: 15—Nucleotide sequence of primer 1 (FIG. 21)
SEQ ID NO: 16—Nucleotide sequence of primer 2 (FIG. 22)
SEQ ID NO: 17—Nucleotide sequence of primer 3 (FIG. 23)
SEQ ID NO: 18—Nucleotide sequence of primer 4 (FIG. 24)
SEQ ID NO: 19—Nucleotide sequence of primer 5 (FIG. 25)
SEQ ID NO: 20—Nucleotide sequence of primer 6 (FIG. 26)
SEQ ID NO: 21—Nucleotide sequence of primer 7 (FIG. 27)
SEQ ID NO: 22—Nucleotide sequence of primer 8 (FIG. 28)
SEQ ID NO: 23—Nucleotide sequence of primer 9 (FIG. 29)
SEQ ID NO: 24—Nucleotide sequence of primer 10 (FIG. 30)
SEQ ID NO: 25—Nucleotide sequence of primer 11 (FIG. 31)
SEQ ID NO: 26—Nucleotide sequence of primer 12 (FIG. 32)
SEQ ID NO: 27—Nucleotide sequence of primer 13 (FIG. 33)
SEQ ID NO: 28—Nucleotide sequence of primer 14 (FIG. 34)
SEQ ID NO: 29—Nucleotide sequence of primer 15 (FIG. 35)
SEQ ID NO: 30—Nucleotide sequence of primer 16 (FIG. 36)
SEQ ID NO: 31—Nucleotide sequence of primer 17 (FIG. 37)
SEQ ID NO: 32—Nucleotide sequence of primer 18 (FIG. 38)
SEQ ID NO: 33—Nucleotide sequence of primer 19 (FIG. 39)
SEQ ID NO: 34—Amino acid sequence of Fc region of human IgG1 (FIG. 40)
SEQ ID NO: 35—Nucleotide sequence of primer 20 (FIG. 41)
SEQ ID NO: 36—Nucleotide sequence of primer 21 (FIG. 42)
SEQ ID NO: 37—Amino acid sequence of Fc region of human IgG2 (FIG. 43)
SEQ ID NO: 38—Nucleotide sequence of primer 22 (FIG. 44)
SEQ ID NO: 39—Nucleotide sequence of primer 23 (FIG. 45)
SEQ ID NO: 40—Amino acid sequence of Fc region of human IgG4P (FIG. 46)
SEQ ID NO: 41—Nucleotide sequence of primer 24 (FIG. 47)
SEQ ID NO: 42—Nucleotide sequence of primer 25 (FIG. 48)
SEQ ID NO: 43—Amino acid sequence of KLK5 inhibitory peptide Fc fusion D0-K51028-Fc (IgG2) (FIG. 49)

SEQ ID NO: 44—Amino acid sequence of KLK5 inhibitory peptide Fc fusion D1-K51028-Fc (IgG2) (FIG. 50)
SEQ ID NO: 45—Amino acid sequence of KLK5 inhibitory peptide Fc fusion D3-K51028-Fc (IgG2) (FIG. 51)
SEQ ID NO: 46—Amino acid sequence of KLK5 inhibitory peptide Fc fusion D0-K51028-Fc (IgG4P) (FIG. 52)

SEQ ID NO: 47—Amino acid sequence of KLK5 inhibitory peptide Fc fusion D1-K51028-Fc (IgG4P) (FIG. 53)
SEQ ID NO: 48—Amino acid sequence of KLK5 inhibitory peptide Fc fusion D3-K51028-Fc (IgG4P) (FIG. 54)

The invention claimed is:

1. A conjugate of a peptide comprising, from the amino terminus to the carboxyl terminus, two or three aspartic acids and/or glutamic acids, the amino acid sequence of a SPINK2 variant peptide set forth in SEQ ID NO: 2, and an amino acid sequence comprising an Fc region of human IgG1, IgG2, or IgG4P, in this order, wherein the Fc region is represented by any one of the amino acid sequences set forth in SEQ ID NO: 34, 37, or 40, and wherein the conjugate has a suppressed blood concentration decrease over time or an increased blood exposure amount compared to a conjugate lacking the two or three aspartic acids and/or glutamic acids at the amino terminus.

2. The conjugate according to claim 1, wherein the amino acid sequence of the SPINK2 variant peptide is attached via a linker sequence to the amino acid sequence comprising the Fc region.

3. The conjugate according to claim 1, wherein the amino acid sequence of the SPINK2 variant peptide is directly attached to the amino acid sequence comprising the Fc region.

4. The conjugate according to claim 1, wherein the two or three aspartic acids and/or glutamic acids are attached via a linker sequence to the amino acid sequence of the SPINK2 variant peptide.

5. The conjugate according to claim 1, wherein the two or three aspartic acids and/or glutamic acids are directly attached to the amino acid sequence of the SPINK2 variant peptide.

6. The conjugate according to claim 1, wherein the SPINK2 variant peptide binds to a human disease-related target molecule.

7. A composition comprising the conjugate according to claim 1.

8. The conjugate according to claim 1, wherein the SPINK2 variant peptide suppresses, inhibits, agonizes or activates an activity of a human disease-related target molecule.

9. A pharmaceutical composition comprising the conjugate according to claim 8.

10. A method for producing the conjugate according to claim 1, comprising step (i) or (ii):

(i) adding the two or three aspartic acids and/or glutamic acids to the amino terminus end of a fusion containing the SPINK2 variant peptide and the Fc region; or (ii) introducing, into a cell, a polynucleotide encoding an amino acid sequence (c) containing an amino acid sequence (a) contained in the fusion and an amino acid sequence (b) consisting of the two or three aspartic acids and/or glutamic acids, wherein the amino acid sequence (b) is located at the amino terminus end of the amino acid sequence (a), culturing the cell, and recovering a conjugate containing the fusion from the culture.

11. The method according to claim 10, wherein the Fc region is fused via a linker to the SPINK2 variant peptide, or an amino acid sequence contained in the SPINK2 variant peptide is attached via a linker sequence to an amino acid sequence contained in the Fc region.

12. The method according to claim 10, wherein the two or three aspartic acids and/or glutamic acids are attached via a linker to the amino terminus end of the fusion.

13. The method according to claim 10, wherein the two or three aspartic acids and/or glutamic acids are directly attached to the amino terminus end of the fusion.

\* \* \* \* \*

SEQUENCE LISTING

```
<160> NUMBER OF SEQ ID NOS: 48

<210> SEQ ID NO 1
<211> LENGTH: 63
<212> TYPE: PRT
<213> ORGANISM: Homo sapiens

<400> SEQUENCE: 1

Asp Pro Gln Phe Gly Leu Phe Ser Lys Tyr Arg Thr Pro Asn Cys Ser
1               5                   10                  15

Gln Tyr Arg Leu Pro Gly Cys Pro Arg His Phe Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 2
<211> LENGTH: 63
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (16)..(22)
<223> OTHER INFORMATION: X is any amino acid
<220> FEATURE:
<221> NAME/KEY: DOMAIN
<222> LOCATION: (24)..(28)
<223> OTHER INFORMATION: X is any amino acid

<400> SEQUENCE: 2

Gly Pro Gln Phe Gly Leu Phe Ser Lys Tyr Arg Thr Pro Asn Cys Xaa
1               5                   10                  15

Xaa Xaa Xaa Xaa Xaa Xaa Cys Xaa Xaa Xaa Xaa Xaa Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 3
<211> LENGTH: 227
<212> TYPE: PRT
<213> ORGANISM: Homo sapiens

<400> SEQUENCE: 3

Ile Ile Asn Gly Ser Asp Cys Asp Met His Thr Gln Pro Trp Gln Ala
1               5                   10                  15

Ala Leu Leu Leu Arg Pro Asn Gln Leu Tyr Cys Gly Ala Val Leu Val
            20                  25                  30

His Pro Gln Trp Leu Leu Thr Ala Ala His Cys Arg Lys Lys Val Phe
        35                  40                  45

Arg Val Arg Leu Gly His Tyr Ser Leu Ser Pro Val Tyr Glu Ser Gly
```

-continued

```
        50                  55                  60

Gln Gln Met Phe Gln Gly Val Lys Ser Ile Pro His Pro Gly Tyr Ser
65                  70                  75                  80

His Pro Gly His Ser Asn Asp Leu Met Leu Ile Lys Leu Asn Arg Arg
                85                  90                  95

Ile Arg Pro Thr Lys Asp Val Arg Pro Ile Asn Val Ser Ser His Cys
            100                 105                 110

Pro Ser Ala Gly Thr Lys Cys Leu Val Ser Gly Trp Gly Thr Thr Lys
        115                 120                 125

Ser Pro Gln Val His Phe Pro Lys Val Leu Gln Cys Leu Asn Ile Ser
        130                 135                 140

Val Leu Ser Gln Lys Arg Cys Glu Asp Ala Tyr Pro Arg Gln Ile Asp
145                 150                 155                 160

Asp Thr Met Phe Cys Ala Gly Asp Lys Ala Gly Arg Asp Ser Cys Gln
                165                 170                 175

Gly Asp Ser Gly Gly Pro Val Val Cys Asn Gly Ser Leu Gln Gly Leu
            180                 185                 190

Val Ser Trp Gly Asp Tyr Pro Cys Ala Arg Pro Asn Arg Pro Gly Val
            195                 200                 205

Tyr Thr Asn Leu Cys Lys Phe Thr Lys Trp Ile Gln Glu Thr Ile Gln
    210                 215                 220

Ala Asn Ser
225

<210> SEQ ID NO 4
<211> LENGTH: 65
<212> TYPE: PRT
<213> ORGANISM: Artificial Sequence
<220> FEATURE:
<223> OTHER INFORMATION: synthetic

<400> SEQUENCE: 4

Gly Pro Gln Phe Gly Leu Phe Ser Lys Tyr Arg Thr Pro Asn Cys Ala
1                   5                   10                  15

Asn Thr Met Lys Gln Asp Cys Thr Arg Glu Tyr Asp Pro Val Cys Gly
                20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 5
<211> LENGTH: 65
<212> TYPE: PRT
<213> ORGANISM: Artificial Sequence
<220> FEATURE:
<223> OTHER INFORMATION: synthetic

<400> SEQUENCE: 5

Gly Pro Gln Phe Gly Leu Phe Ser Lys Tyr Arg Thr Pro Asn Cys Tyr
1                   5                   10                  15

Gln Tyr Arg Ser Lys Gly Cys Thr His Glu Tyr Asp Pro Val Cys Gly
                20                  25                  30

Ser Asp Met Ser Thr Tyr Ala Asn Glu Cys Thr Leu Cys Met Lys Ile
        35                  40                  45
```

-continued

```
Arg Glu Gly Gly His Asn Ile Lys Ile Ile Arg Asn Gly Pro Cys Gly
    50                  55                  60

Gly
65

<210> SEQ ID NO 6
<211> LENGTH: 295
<212> TYPE: PRT
<213> ORGANISM: Artificial Sequence
<220> FEATURE:
<223> OTHER INFORMATION: synthetic

<400> SEQUENCE: 6

Gly Pro Gln Phe Gly Leu Phe Ser Lys Tyr Arg Thr Pro Asn Cys Tyr
1               5                   10                  15

Gln Tyr Arg Ser Lys Gly Cys Thr His Glu Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Glu
    50                  55                  60

Pro Lys Ser Cys Asp Lys Thr His Thr Cys Pro Pro Cys Pro Ala Pro
65                  70                  75                  80

Glu Leu Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
        115                 120                 125

Gly Val Glu Val His Asn Ala Lys Thr Lys Pro Arg Glu Glu Gln Tyr
    130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Glu Glu Met Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295

<210> SEQ ID NO 7
<211> LENGTH: 296
<212> TYPE: PRT
<213> ORGANISM: Artificial Sequence
<220> FEATURE:
```

-continued

```
<223> OTHER INFORMATION: synthetic

<400> SEQUENCE: 7

Asp Gly Pro Gln Phe Gly Leu Phe Ser Lys Tyr Arg Thr Pro Asn Cys
1               5                   10                  15

Tyr Gln Tyr Arg Ser Lys Gly Cys Thr His Glu Tyr Asp Pro Val Cys
            20                  25                  30

Gly Ser Asp Met Ser Thr Tyr Ala Asn Glu Cys Thr Leu Cys Met Lys
        35                  40                  45

Ile Arg Glu Gly Gly His Asn Ile Lys Ile Ile Arg Asn Gly Pro Cys
    50                  55                  60

Glu Pro Lys Ser Cys Asp Lys Thr His Thr Cys Pro Pro Cys Pro Ala
65                  70                  75                  80

Pro Glu Leu Leu Gly Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Ser His Glu Asp Pro Glu Val Lys Phe Asn Trp Tyr Val
        115                 120                 125

Asp Gly Val Glu Val His Asn Ala Lys Thr Lys Pro Arg Glu Glu Gln
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Glu Met Thr
        195                 200                 205

Lys Asn Gln Val Ser Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 8
<211> LENGTH: 297
<212> TYPE: PRT
<213> ORGANISM: Artificial Sequence
<220> FEATURE:
<223> OTHER INFORMATION: synthetic

<400> SEQUENCE: 8

Asp Asp Gly Pro Gln Phe Gly Leu Phe Ser Lys Tyr Arg Thr Pro Asn
1               5                   10                  15

Cys Tyr Gln Tyr Arg Ser Lys Gly Cys Thr His Glu Tyr Asp Pro Val
            20                  25                  30

Cys Gly Ser Asp Met Ser Thr Tyr Ala Asn Glu Cys Thr Leu Cys Met
        35                  40                  45
```

-continued

```
Lys Ile Arg Glu Gly Gly His Asn Ile Lys Ile Ile Arg Asn Gly Pro
    50                  55                  60

Cys Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
            115                 120                 125

Val Asp Gly Val Glu Val His Asn Ala Lys Thr Lys Pro Arg Glu Glu
        130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
                180                 185                 190

Pro Arg Glu Pro Gln Val Tyr Thr Leu Pro Pro Ser Arg Glu Glu Met
            195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
            275                 280                 285

Lys Ser Leu Ser Leu Ser Pro Gly Lys
    290                 295
```

```
<210> SEQ ID NO 9
<211> LENGTH: 298
<212> TYPE: PRT
<213> ORGANISM: Artificial Sequence
<220> FEATURE:
<223> OTHER INFORMATION: synthetic

<400> SEQUENCE: 9
```

```
Asp Asp Asp Gly Pro Gln Phe Gly Leu Phe Ser Lys Tyr Arg Thr Pro
1               5                   10                  15

Asn Cys Tyr Gln Tyr Arg Ser Lys Gly Cys Thr His Glu Tyr Asp Pro
            20                  25                  30

Val Cys Gly Ser Asp Met Ser Thr Tyr Ala Asn Glu Cys Thr Leu Cys
            35                  40                  45

Met Lys Ile Arg Glu Gly Gly His Asn Ile Lys Ile Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110
```

```
Val Val Val Asp Val Ser His Glu Asp Pro Glu Val Lys Phe Asn Trp
        115             120             125

Tyr Val Asp Gly Val Glu Val His Asn Ala Lys Thr Lys Pro Arg Glu
        130             135             140

Glu Gln Tyr Asn Ser Thr Tyr Arg Val Val Ser Val Leu Thr Val Leu
145             150             155             160

His Gln Asp Trp Leu Asn Gly Lys Glu Tyr Lys Cys Lys Val Ser Asn
            165             170             175

Lys Ala Leu Pro Ala Pro Ile Glu Lys Thr Ile Ser Lys Ala Lys Gly
            180             185             190

Gln Pro Arg Glu Pro Gln Val Tyr Thr Leu Pro Pro Ser Arg Glu Glu
            195             200             205

Met Thr Lys Asn Gln Val Ser Leu Thr Cys Leu Val Lys Gly Phe Tyr
        210             215             220

Pro Ser Asp Ile Ala Val Glu Trp Glu Ser Asn Gly Gln Pro Glu Asn
225             230             235             240

Asn Tyr Lys Thr Thr Pro Pro Val Leu Asp Ser Asp Gly Ser Phe Phe
            245             250             255

Leu Tyr Ser Lys Leu Thr Val Asp Lys Ser Arg Trp Gln Gln Gly Asn
            260             265             270

Val Phe Ser Cys Ser Val Met His Glu Ala Leu His Asn His Tyr Thr
            275             280             285

Gln Lys Ser Leu Ser Leu Ser Pro Gly Lys
        290             295

<210> SEQ ID NO 10
<211> LENGTH: 299
<212> TYPE: PRT
<213> ORGANISM: Artificial Sequence
<220> FEATURE:
<223> OTHER INFORMATION: synthetic

<400> SEQUENCE: 10

Asp Asp Asp Asp Gly Pro Gln Phe Gly Leu Phe Ser Lys Tyr Arg Thr
1               5               10              15

Pro Asn Cys Tyr Gln Tyr Arg Ser Lys Gly Cys Thr His Glu Tyr Asp
            20              25              30

Pro Val Cys Gly Ser Asp Met Ser Thr Tyr Ala Asn Glu Cys Thr Leu
        35              40              45

Cys Met Lys Ile Arg Glu Gly Gly His Asn Ile Lys Ile Ile Arg Asn
    50              55              60

Gly Pro Cys Glu Pro Lys Ser Cys Asp Lys Thr His Thr Cys Pro Pro
65              70              75              80

Cys Pro Ala Pro Glu Leu Leu Gly Gly Pro Ser Val Phe Leu Phe Pro
            85              90              95

Pro Lys Pro Lys Asp Thr Leu Met Ile Ser Arg Thr Pro Glu Val Thr
        100             105             110

Cys Val Val Val Asp Val Ser His Glu Asp Pro Glu Val Lys Phe Asn
        115             120             125

Trp Tyr Val Asp Gly Val Glu Val His Asn Ala Lys Thr Lys Pro Arg
        130             135             140

Glu Glu Gln Tyr Asn Ser Thr Tyr Arg Val Val Ser Val Leu Thr Val
145             150             155             160

Leu His Gln Asp Trp Leu Asn Gly Lys Glu Tyr Lys Cys Lys Val Ser
            165             170             175
```

-continued

```
Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
            195                 200                 205

Glu Met Thr Lys Asn Gln Val Ser Leu Thr Cys Leu Val Lys Gly Phe
        210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
            275                 280                 285

Thr Gln Lys Ser Leu Ser Leu Ser Pro Gly Lys
        290                 295

<210> SEQ ID NO 11
<211> LENGTH: 300
<212> TYPE: PRT
<213> ORGANISM: Artificial Sequence
<220> FEATURE:
<223> OTHER INFORMATION: synthetic

<400> SEQUENCE: 11

Asp Asp Asp Asp Asp Gly Pro Gln Phe Gly Leu Phe Ser Lys Tyr Arg
1               5                   10                  15

Thr Pro Asn Cys Tyr Gln Tyr Arg Ser Lys Gly Cys Thr His Glu Tyr
            20                  25                  30

Asp Pro Val Cys Gly Ser Asp Met Ser Thr Tyr Ala Asn Glu Cys Thr
            35                  40                  45

Leu Cys Met Lys Ile Arg Glu Gly Gly His Asn Ile Lys Ile Ile Arg
        50                  55                  60

Asn Gly Pro Cys Glu Pro Lys Ser Cys Asp Lys Thr His Thr Cys Pro
65                  70                  75                  80

Pro Cys Pro Ala Pro Glu Leu Leu Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
            115                 120                 125

Asn Trp Tyr Val Asp Gly Val Glu Val His Asn Ala Lys Thr Lys Pro
        130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
            195                 200                 205

Glu Glu Met Thr Lys Asn Gln Val Ser Leu Thr Cys Leu Val Lys Gly
        210                 215                 220

Phe Tyr Pro Ser Asp Ile Ala Val Glu Trp Glu Ser Asn Gly Gln Pro
225                 230                 235                 240
```

-continued

```
Glu Asn Asn Tyr Lys Thr Thr Pro Pro Val Leu Asp Ser Asp Gly Ser
            245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
            275                 280                 285

Tyr Thr Gln Lys Ser Leu Ser Leu Ser Pro Gly Lys
    290                 295                 300

<210> SEQ ID NO 12
<211> LENGTH: 299
<212> TYPE: PRT
<213> ORGANISM: Artificial Sequence
<220> FEATURE:
<223> OTHER INFORMATION: synthetic

<400> SEQUENCE: 12

Gly Pro Gln Phe Gly Leu Phe Ser Lys Tyr Arg Thr Pro Asn Cys Tyr
1               5                   10                  15

Gln Tyr Arg Ser Lys Gly Cys Thr His Glu Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Asp
    50                  55                  60

Asp Asp Asp Asp Glu Pro Lys Ser Cys Asp Lys Thr His Thr Cys Pro
65                  70                  75                  80

Pro Cys Pro Ala Pro Glu Leu Leu Gly Gly Pro Ser Val Phe Leu Phe
            85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
            115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
            165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
            195                 200                 205

Glu Glu Met Thr Lys Asn Gln Val Ser Leu Thr Cys Leu Val Lys Gly
            210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
            245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
            275                 280                 285

Tyr Thr Gln Lys Ser Leu Ser Leu Ser Pro Gly
    290                 295
```

```
<210> SEQ ID NO 13
<211> LENGTH: 296
<212> TYPE: PRT
<213> ORGANISM: Artificial Sequence
<220> FEATURE:
<223> OTHER INFORMATION: synthetic

<400> SEQUENCE: 13

Glu Gly Pro Gln Phe Gly Leu Phe Ser Lys Tyr Arg Thr Pro Asn Cys
1               5                   10                  15

Tyr Gln Tyr Arg Ser Lys Gly Cys Thr His Glu Tyr Asp Pro Val Cys
            20                  25                  30

Gly Ser Asp Met Ser Thr Tyr Ala Asn Glu Cys Thr Leu Cys Met Lys
        35                  40                  45

Ile Arg Glu Gly Gly His Asn Ile Lys Ile Ile Arg Asn Gly Pro Cys
        50                  55                  60

Glu Pro Lys Ser Cys Asp Lys Thr His Thr Cys Pro Pro Cys Pro Ala
65                  70                  75                  80

Pro Glu Leu Leu Gly Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Ser His Glu Asp Pro Glu Val Lys Phe Asn Trp Tyr Val
            115                 120                 125

Asp Gly Val Glu Val His Asn Ala Lys Thr Lys Pro Arg Glu Glu Gln
        130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
                180                 185                 190

Arg Glu Pro Gln Val Tyr Thr Leu Pro Pro Ser Arg Glu Glu Met Thr
            195                 200                 205

Lys Asn Gln Val Ser Leu Thr Cys Leu Val Lys Gly Phe Tyr Pro Ser
        210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
                260                 265                 270

Ser Cys Ser Val Met His Glu Ala Leu His Asn His Tyr Thr Gln Lys
            275                 280                 285

Ser Leu Ser Leu Ser Pro Gly Lys
        290                 295

<210> SEQ ID NO 14
<211> LENGTH: 296
<212> TYPE: PRT
<213> ORGANISM: Artificial Sequence
<220> FEATURE:
<223> OTHER INFORMATION: synthetic

<400> SEQUENCE: 14

Asp Gly Pro Gln Phe Gly Leu Phe Ser Lys Tyr Arg Thr Pro Asn Cys
```

```
1               5                   10                  15

Ala Asn Thr Met Lys Gln Asp Cys Thr Arg Glu Tyr Asp Pro Val Cys
            20                  25                  30

Gly Ser Asp Met Ser Thr Tyr Ala Asn Glu Cys Thr Leu Cys Met Lys
            35                  40                  45

Ile Arg Glu Gly Gly His Asn Ile Lys Ile Ile Arg Asn Gly Pro Cys
        50                  55                  60

Glu Pro Lys Ser Cys Asp Lys Thr His Thr Cys Pro Pro Cys Pro Ala
65                  70                  75                  80

Pro Glu Leu Leu Gly Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Ser His Glu Asp Pro Glu Val Lys Phe Asn Trp Tyr Val
            115                 120                 125

Asp Gly Val Glu Val His Asn Ala Lys Thr Lys Pro Arg Glu Glu Gln
        130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
                180                 185                 190

Arg Glu Pro Gln Val Tyr Thr Leu Pro Pro Ser Arg Glu Glu Met Thr
                195                 200                 205

Lys Asn Gln Val Ser Leu Thr Cys Leu Val Lys Gly Phe Tyr Pro Ser
            210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
                260                 265                 270

Ser Cys Ser Val Met His Glu Ala Leu His Asn His Tyr Thr Gln Lys
                275                 280                 285

Ser Leu Ser Leu Ser Pro Gly Lys
    290                 295
```

<210> SEQ ID NO 15
<211> LENGTH: 36
<212> TYPE: DNA
<213> ORGANISM: Artificial Sequence
<220> FEATURE:
<223> OTHER INFORMATION: synthetic

<400> SEQUENCE: 15
agatgggtgt tgtctggccc tcagttcggc ctgttc            36

<210> SEQ ID NO 16
<211> LENGTH: 18
<212> TYPE: DNA
<213> ORGANISM: Artificial Sequence
<220> FEATURE:
<223> OTHER INFORMATION: synthetic

<400> SEQUENCE: 16
gcaggggcca ttccggat            18

<210> SEQ ID NO 17
<211> LENGTH: 39
<212> TYPE: DNA
<213> ORGANISM: Artificial Sequence
<220> FEATURE:
<223> OTHER INFORMATION: synthetic

<400> SEQUENCE: 17
agatgggtgt tgtctgacgg ccctcagttc ggcctgttc                          39

<210> SEQ ID NO 18
<211> LENGTH: 39
<212> TYPE: DNA
<213> ORGANISM: Artificial Sequence
<220> FEATURE:
<223> OTHER INFORMATION: synthetic

<400> SEQUENCE: 18
agatgggtgt tgtctgaagg ccctcagttc ggcctgttc                          39

<210> SEQ ID NO 19
<211> LENGTH: 42
<212> TYPE: DNA
<213> ORGANISM: Artificial Sequence
<220> FEATURE:
<223> OTHER INFORMATION: synthetic

<400> SEQUENCE: 19
agatgggtgt tgtctgacga cggccctcag ttcggcctgt tc                      42

<210> SEQ ID NO 20
<211> LENGTH: 45
<212> TYPE: DNA
<213> ORGANISM: Artificial Sequence
<220> FEATURE:
<223> OTHER INFORMATION: synthetic

<400> SEQUENCE: 20
agatgggtgt tgtctgatga cgacggccct cagttcggcc tgttc                   45

<210> SEQ ID NO 21
<211> LENGTH: 48
<212> TYPE: DNA
<213> ORGANISM: Artificial Sequence
<220> FEATURE:
<223> OTHER INFORMATION: synthetic

<400> SEQUENCE: 21
agatgggtgt tgtctgatga tgacgacggc cctcagttcg gcctgttc                48

<210> SEQ ID NO 22
<211> LENGTH: 51
<212> TYPE: DNA
<213> ORGANISM: Artificial Sequence
<220> FEATURE:
<223> OTHER INFORMATION: synthetic

<400> SEQUENCE: 22
agatgggtgt tgtctgacga tgatgacgac ggccctcagt tcggcctgtt c            51

<210> SEQ ID NO 23
<211> LENGTH: 48
<212> TYPE: DNA
<213> ORGANISM: Artificial Sequence
<220> FEATURE:

-continued

<223> OTHER INFORMATION: synthetic

<400> SEQUENCE: 23
aaaatctaga gccgccacca tgaagcacct gtggttcttt ctgctgct                48

<210> SEQ ID NO 24
<211> LENGTH: 44
<212> TYPE: DNA
<213> ORGANISM: Artificial Sequence
<220> FEATURE:
<223> OTHER INFORMATION: synthetic

<400> SEQUENCE: 24
agacaacacc catctaggag cggccaccag cagcagaaag aacc                44

<210> SEQ ID NO 25
<211> LENGTH: 36
<212> TYPE: DNA
<213> ORGANISM: Artificial Sequence
<220> FEATURE:
<223> OTHER INFORMATION: synthetic

<400> SEQUENCE: 25
atccggaatg gccctgcga acccaagagc tgcgac                36

<210> SEQ ID NO 26
<211> LENGTH: 30
<212> TYPE: DNA
<213> ORGANISM: Artificial Sequence
<220> FEATURE:
<223> OTHER INFORMATION: synthetic

<400> SEQUENCE: 26
aaaagtttaa actcatttgc cggggctcag                30

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
gatgacgacg aacccaagag ctgc                24

<210> SEQ ID NO 28
<211> LENGTH: 21
<212> TYPE: DNA
<213> ORGANISM: Artificial Sequence
<220> FEATURE:
<223> OTHER INFORMATION: synthetic

<400> SEQUENCE: 28
atcgtcgcag gggccattcc g                21

<210> SEQ ID NO 29
<211> LENGTH: 43
<212> TYPE: DNA
<213> ORGANISM: Artificial Sequence
<220> FEATURE:
<223> OTHER INFORMATION: synthetic

<400> SEQUENCE: 29
ggcgattata aagatgacga tgataaacac catcaccacc atc                43

```
<210> SEQ ID NO 30
<211> LENGTH: 43
<212> TYPE: DNA
<213> ORGANISM: Artificial Sequence
<220> FEATURE:
<223> OTHER INFORMATION: synthetic

<400> SEQUENCE: 30
gtttaaactc aatgatggtg gtgatggtgt ttatcatcgt cat                        43

<210> SEQ ID NO 31
<211> LENGTH: 40
<212> TYPE: DNA
<213> ORGANISM: Artificial Sequence
<220> FEATURE:
<223> OTHER INFORMATION: synthetic

<400> SEQUENCE: 31
aaaatctaga gccgccacca tggccacagc tagaccccct                            40

<210> SEQ ID NO 32
<211> LENGTH: 43
<212> TYPE: DNA
<213> ORGANISM: Artificial Sequence
<220> FEATURE:
<223> OTHER INFORMATION: synthetic

<400> SEQUENCE: 32
cgtcatcttt ataatcgccg ctgttggcct ggatggtttc ctg                        43

<210> SEQ ID NO 33
<211> LENGTH: 34
<212> TYPE: DNA
<213> ORGANISM: Artificial Sequence
<220> FEATURE:
<223> OTHER INFORMATION: synthetic

<400> SEQUENCE: 33
aaaagtttaa actcaatgat ggtggtgatg gtgt                                  34

<210> SEQ ID NO 34
<211> LENGTH: 232
<212> TYPE: PRT
<213> ORGANISM: Homo sapiens

<400> SEQUENCE: 34

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125
```

-continued

```
Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

```
<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
tgagtttaaa cttttaaacg gggg                                          24
```

```
<210> SEQ ID NO 36
<211> LENGTH: 24
<212> TYPE: DNA
<213> ORGANISM: Artificial Sequence
<220> FEATURE:
<223> OTHER INFORMATION: synthetic

<400> SEQUENCE: 36
gcaggggcca ttccggatga tctt                                          24
```

```
<210> SEQ ID NO 37
<211> LENGTH: 228
<212> TYPE: PRT
<213> ORGANISM: Homo sapiens

<400> SEQUENCE: 37

Glu Arg Lys Cys Cys Val Glu Cys Pro Pro Cys Pro Ala Pro Pro Val
1                   5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
    130                 135                 140
```

-continued

```
Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 38
<211> LENGTH: 39
<212> TYPE: DNA
<213> ORGANISM: Artificial Sequence
<220> FEATURE:
<223> OTHER INFORMATION: synthetic

<400> SEQUENCE: 38
cggaatggcc cctgcgagcg taagtgttgt gtggagtgt                                           39

<210> SEQ ID NO 39
<211> LENGTH: 39
<212> TYPE: DNA
<213> ORGANISM: Artificial Sequence
<220> FEATURE:
<223> OTHER INFORMATION: synthetic

<400> SEQUENCE: 39
ccccgtttaa actcactttc cagggctcag ggaaaggct                                           39

<210> SEQ ID NO 40
<211> LENGTH: 229
<212> TYPE: PRT
<213> ORGANISM: Homo sapiens

<400> SEQUENCE: 40

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
```

-continued

```
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 41
<211> LENGTH: 39
<212> TYPE: DNA
<213> ORGANISM: Artificial Sequence
<220> FEATURE:
<223> OTHER INFORMATION: synthetic

<400> SEQUENCE: 41
cggaatggcc cctgcgaatc taagtacggc cctccctgc                            39

<210> SEQ ID NO 42
<211> LENGTH: 39
<212> TYPE: DNA
<213> ORGANISM: Artificial Sequence
<220> FEATURE:
<223> OTHER INFORMATION: synthetic

<400> SEQUENCE: 42
ccccgtttaa actcatttgc ccaggctcag agacaggga                            39

<210> SEQ ID NO 43
<211> LENGTH: 291
<212> TYPE: PRT
<213> ORGANISM: Artificial Sequence
<220> FEATURE:
<223> OTHER INFORMATION: synthetic

<400> SEQUENCE: 43

Gly Pro Gln Phe Gly Leu Phe Ser Lys Tyr Arg Thr Pro Asn Cys Tyr
1               5                   10                  15

Gln Tyr Arg Ser Lys Gly Cys Thr His Glu Tyr Asp Pro Val Cys Gly
                20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys Glu
        50                  55                  60

Arg Lys Cys Cys Val Glu Cys Pro Pro Cys Pro Ala Pro Pro Val Ala
65                  70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser His
            100                 105                 110

Glu Asp Pro Glu Val Gln Phe Asn Trp Tyr Val Asp Gly Val Glu Val
        115                 120                 125

His Asn Ala Lys Thr Lys Pro Arg Glu Glu Gln Phe Asn Ser Thr Phe
    130                 135                 140

Arg Val Val Ser Val Leu Thr Val Val His Gln Asp Trp Leu Asn Gly
```

-continued

```
145                 150                 155                 160

Lys Glu Tyr Lys Cys Lys Val Ser Asn Lys Gly Leu Pro Ala Pro Ile
                165                 170                 175

Glu Lys Thr Ile Ser Lys Thr Lys Gly Gln Pro Arg Glu Pro Gln Val
                180                 185                 190

Tyr Thr Leu Pro Pro Ser Arg Glu Glu Met Thr Lys Asn Gln Val Ser
                195                 200                 205

Leu Thr Cys Leu Val Lys Gly Phe Tyr Pro Ser Asp Ile Ala Val Glu
        210                 215                 220

Trp Glu Ser Asn Gly Gln Pro Glu Asn Asn Tyr Lys Thr Thr Pro Pro
225                 230                 235                 240

Met Leu Asp Ser Asp Gly Ser Phe Phe Leu Tyr Ser Lys Leu Thr Val
                245                 250                 255

Asp Lys Ser Arg Trp Gln Gln Gly Asn Val Phe Ser Cys Ser Val Met
                260                 265                 270

His Glu Ala Leu His Asn His Tyr Thr Gln Lys Ser Leu Ser Leu Ser
                275                 280                 285

Pro Gly Lys
        290

<210> SEQ ID NO 44
<211> LENGTH: 292
<212> TYPE: PRT
<213> ORGANISM: Artificial Sequence
<220> FEATURE:
<223> OTHER INFORMATION: synthetic

<400> SEQUENCE: 44

Asp Gly Pro Gln Phe Gly Leu Phe Ser Lys Tyr Arg Thr Pro Asn Cys
1               5                   10                  15

Tyr Gln Tyr Arg Ser Lys Gly Cys Thr His Glu Tyr Asp Pro Val Cys
                20                  25                  30

Gly Ser Asp Met Ser Thr Tyr Ala Asn Glu Cys Thr Leu Cys Met Lys
                35                  40                  45

Ile Arg Glu Gly Gly His Asn Ile Lys Ile Ile Arg Asn Gly Pro Cys
        50                  55                  60

Glu Arg Lys Cys Cys Val Glu Cys Pro Pro Cys Pro Ala Pro Pro Val
65                  70                  75                  80

Ala Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
                100                 105                 110

His Glu Asp Pro Glu Val Gln Phe Asn Trp Tyr Val Asp Gly Val Glu
        115                 120                 125

Val His Asn Ala Lys Thr Lys Pro Arg Glu Glu Gln Phe Asn Ser Thr
        130                 135                 140

Phe Arg Val Val Ser Val Leu Thr Val Val His Gln Asp Trp Leu Asn
145                 150                 155                 160

Gly Lys Glu Tyr Lys Cys Lys Val Ser Asn Lys Gly Leu Pro Ala Pro
                165                 170                 175

Ile Glu Lys Thr Ile Ser Lys Thr Lys Gly Gln Pro Arg Glu Pro Gln
                180                 185                 190

Val Tyr Thr Leu Pro Pro Ser Arg Glu Glu Met Thr Lys Asn Gln Val
                195                 200                 205

Ser Leu Thr Cys Leu Val Lys Gly Phe Tyr Pro Ser Asp Ile Ala Val
```

```
       210                 215                 220

Glu Trp Glu Ser Asn Gly Gln Pro Glu Asn Asn Tyr Lys Thr Thr Pro
225                 230                 235                 240

Pro Met Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
                260                 265                 270

Met His Glu Ala Leu His Asn His Tyr Thr Gln Lys Ser Leu Ser Leu
            275                 280                 285

Ser Pro Gly Lys
        290

<210> SEQ ID NO 45
<211> LENGTH: 294
<212> TYPE: PRT
<213> ORGANISM: Artificial Sequence
<220> FEATURE:
<223> OTHER INFORMATION: synthetic

<400> SEQUENCE: 45

Asp Asp Asp Gly Pro Gln Phe Gly Leu Phe Ser Lys Tyr Arg Thr Pro
1               5                   10                  15

Asn Cys Tyr Gln Tyr Arg Ser Lys Gly Cys Thr His Glu Tyr Asp Pro
                20                  25                  30

Val Cys Gly Ser Asp Met Ser Thr Tyr Ala Asn Glu Cys Thr Leu Cys
            35                  40                  45

Met Lys Ile Arg Glu Gly Gly His Asn Ile Lys Ile Ile Arg Asn Gly
        50                  55                  60

Pro Cys Glu Arg Lys Cys Cys Val Glu Cys Pro Pro Cys Pro Ala Pro
65                  70                  75                  80

Pro Val Ala Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
                100                 105                 110

Val Ser His Glu Asp Pro Glu Val Gln Phe Asn Trp Tyr Val Asp Gly
            115                 120                 125

Val Glu Val His Asn Ala Lys Thr Lys Pro Arg Glu Glu Gln Phe Asn
        130                 135                 140

Ser Thr Phe Arg Val Val Ser Val Leu Thr Val Val His Gln Asp Trp
145                 150                 155                 160

Leu Asn Gly Lys Glu Tyr Lys Cys Lys Val Ser Asn Lys Gly Leu Pro
                165                 170                 175

Ala Pro Ile Glu Lys Thr Ile Ser Lys Thr Lys Gly Gln Pro Arg Glu
                180                 185                 190

Pro Gln Val Tyr Thr Leu Pro Pro Ser Arg Glu Glu Met Thr Lys Asn
            195                 200                 205

Gln Val Ser Leu Thr Cys Leu Val Lys Gly Phe Tyr Pro Ser Asp Ile
        210                 215                 220

Ala Val Glu Trp Glu Ser Asn Gly Gln Pro Glu Asn Asn Tyr Lys Thr
225                 230                 235                 240

Thr Pro Pro Met Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
```

-continued

```
        275             280             285

Ser Leu Ser Pro Gly Lys
    290

<210> SEQ ID NO 46
<211> LENGTH: 292
<212> TYPE: PRT
<213> ORGANISM: Artificial Sequence
<220> FEATURE:
<223> OTHER INFORMATION: synthetic

<400> SEQUENCE: 46

Gly Pro Gln Phe Gly Leu Phe Ser Lys Tyr Arg Thr Pro Asn Cys Tyr
1               5                   10                  15

Gln Tyr Arg Ser Lys Gly Cys Thr His Glu Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Glu
    50                  55                  60

Ser Lys Tyr Gly Pro Pro Cys Pro Pro Cys Pro Ala Pro Glu Phe Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

Gln Glu Asp Pro Glu Val Gln Phe Asn Trp Tyr Val Asp Gly Val Glu
        115                 120                 125

Val His Asn Ala Lys Thr Lys Pro Arg Glu Glu Gln Phe Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Gly Leu Pro Ser Ser
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Gln Glu Glu Met Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Arg Leu Thr
                245                 250                 255

Val Asp Lys Ser Arg Trp Gln Glu Gly Asn Val Phe Ser Cys Ser Val
            260                 265                 270

Met His Glu Ala Leu His Asn His Tyr Thr Gln Lys Ser Leu Ser Leu
        275                 280                 285

Ser Leu Gly Lys
    290

<210> SEQ ID NO 47
<211> LENGTH: 293
<212> TYPE: PRT
<213> ORGANISM: Artificial Sequence
<220> FEATURE:
<223> OTHER INFORMATION: synthetic
```

<400> SEQUENCE: 47

```
Asp Gly Pro Gln Phe Gly Leu Phe Ser Lys Tyr Arg Thr Pro Asn Cys
1               5                   10                  15

Tyr Gln Tyr Arg Ser Lys Gly Cys Thr His Glu Tyr Asp Pro Val Cys
                20                  25                  30

Gly Ser Asp Met Ser Thr Tyr Ala Asn Glu Cys Thr Leu Cys Met Lys
            35                  40                  45

Ile Arg Glu Gly Gly His Asn Ile Lys Ile Ile Arg Asn Gly Pro Cys
            50                  55                  60

Glu Ser Lys Tyr Gly Pro Pro Cys Pro Pro Cys Pro Ala Pro Glu Phe
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
                100                 105                 110

Ser Gln Glu Asp Pro Glu Val Gln Phe Asn Trp Tyr Val Asp Gly Val
            115                 120                 125

Glu Val His Asn Ala Lys Thr Lys Pro Arg Glu Glu Gln Phe Asn Ser
    130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Gly Leu Pro Ser
                165                 170                 175

Ser Ile Glu Lys Thr Ile Ser Lys Ala Lys Gly Gln Pro Arg Glu Pro
            180                 185                 190

Gln Val Tyr Thr Leu Pro Pro Ser Gln Glu Glu Met Thr Lys Asn Gln
            195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Arg Leu
                245                 250                 255

Thr Val Asp Lys Ser Arg Trp Gln Glu Gly Asn Val Phe Ser Cys Ser
                260                 265                 270

Val Met His Glu Ala Leu His Asn His Tyr Thr Gln Lys Ser Leu Ser
                275                 280                 285

Leu Ser Leu Gly Lys
        290
```

<210> SEQ ID NO 48
<211> LENGTH: 295
<212> TYPE: PRT
<213> ORGANISM: Artificial Sequence
<220> FEATURE:
<223> OTHER INFORMATION: synthetic

<400> SEQUENCE: 48

```
Asp Asp Asp Gly Pro Gln Phe Gly Leu Phe Ser Lys Tyr Arg Thr Pro
1               5                   10                  15

Asn Cys Tyr Gln Tyr Arg Ser Lys Gly Cys Thr His Glu Tyr Asp Pro
                20                  25                  30

Val Cys Gly Ser Asp Met Ser Thr Tyr Ala Asn Glu Cys Thr Leu Cys
            35                  40                  45
```

-continued

```
Met Lys Ile Arg Glu Gly Gly His Asn Ile Lys Ile Ile Arg Asn Gly
    50              55                  60

Pro Cys Glu Ser Lys Tyr Gly Pro Pro Cys Pro Pro Cys Pro Ala Pro
65              70              75                  80

Glu Phe Leu Gly Gly Pro Ser Val Phe Leu Phe Pro Pro Lys Pro Lys
            85                  90                  95

Asp Thr Leu Met Ile Ser Arg Thr Pro Glu Val Thr Cys Val Val Val
            100             105             110

Asp Val Ser Gln Glu Asp Pro Glu Val Gln Phe Asn Trp Tyr Val Asp
        115             120                 125

Gly Val Glu Val His Asn Ala Lys Thr Lys Pro Arg Glu Glu Gln Phe
    130             135             140

Asn Ser Thr Tyr Arg Val Val Ser Val Leu Thr Val Leu His Gln Asp
145             150             155             160

Trp Leu Asn Gly Lys Glu Tyr Lys Cys Lys Val Ser Asn Lys Gly Leu
            165             170             175

Pro Ser Ser Ile Glu Lys Thr Ile Ser Lys Ala Lys Gly Gln Pro Arg
            180             185             190

Glu Pro Gln Val Tyr Thr Leu Pro Pro Ser Gln Glu Glu Met Thr Lys
        195             200             205

Asn Gln Val Ser Leu Thr Cys Leu Val Lys Gly Phe Tyr Pro Ser Asp
    210             215             220

Ile Ala Val Glu Trp Glu Ser Asn Gly Gln Pro Glu Asn Asn Tyr Lys
225             230             235             240

Thr Thr Pro Pro Val Leu Asp Ser Asp Gly Ser Phe Phe Leu Tyr Ser
            245             250             255

Arg Leu Thr Val Asp Lys Ser Arg Trp Gln Glu Gly Asn Val Phe Ser
            260             265             270

Cys Ser Val Met His Glu Ala Leu His Asn His Tyr Thr Gln Lys Ser
            275             280             285

Leu Ser Leu Ser Leu Gly Lys
290             295
```